United States Patent
Gee et al.

(10) Patent No.: US 10,941,435 B2
(45) Date of Patent: Mar. 9, 2021

(54) METHODS AND COMPOSITIONS FOR DETECTING OR MEASURING CASPASES OR APOPTOSIS

(71) Applicant: Life Technologies Corporation, Carlsbad, CA (US)

(72) Inventors: Kyle Gee, Springfield, OR (US); Wenjun Zhou, Eugene, OR (US); Shih-Jung Huang, Eugene, OR (US); Monica Tomaszewski, Pittsburgh, PA (US)

(73) Assignee: Life Technologies Corporation, Carlsbad, CA (US)

( * ) Notice: Subject to any disclaimer, the term of this patent is extended or adjusted under 35 U.S.C. 154(b) by 76 days.

(21) Appl. No.: 16/306,609

(22) PCT Filed: Jun. 21, 2017

(86) PCT No.: PCT/US2017/038444
§ 371 (c)(1),
(2) Date: Dec. 3, 2018

(87) PCT Pub. No.: WO2017/223147
PCT Pub. Date: Dec. 28, 2017

(65) Prior Publication Data
US 2019/0309341 A1 Oct. 10, 2019

Related U.S. Application Data

(60) Provisional application No. 62/353,892, filed on Jun. 23, 2016.

(51) Int. Cl.
| | |
|---|---|
| *C12Q 1/37* | (2006.01) |
| *C07K 5/103* | (2006.01) |
| *C07K 5/113* | (2006.01) |
| *G01N 21/64* | (2006.01) |
| *G01N 33/58* | (2006.01) |
| *C12Q 1/48* | (2006.01) |

(52) U.S. Cl.
CPC .............. *C12Q 1/37* (2013.01); *C07K 5/101* (2013.01); *C07K 5/1021* (2013.01); *C12Q 1/48* (2013.01); *G01N 21/6428* (2013.01); *G01N 21/6486* (2013.01); *G01N 33/582* (2013.01); *G01N 2021/6439* (2013.01); *G01N 2333/96466* (2013.01); *G01N 2510/00* (2013.01)

(58) Field of Classification Search
CPC combination set(s) only.
See application file for complete search history.

(56) References Cited

U.S. PATENT DOCUMENTS

| | | |
|---|---|---|
| 6,335,429 B1 | 1/2002 | Cai et al. |
| 2006/0166223 A1 | 7/2006 | Reed et al. |
| 2012/0252063 A1 | 10/2012 | Mao et al. |

FOREIGN PATENT DOCUMENTS

WO  WO-2007100392 A2 * 9/2007 ............... C12N 9/96

OTHER PUBLICATIONS

Telford, W. et al., Cytometry 1992, vol. 13, pp. 137-143.*
International Search Report and Written Opinion for Application No. PCT/US2017/038444, dated Dec. 13, 2017, 16 pages.
International Preliminary report on patentability for Application No. PCT/US2017/038444, dated Jan. 3, 2019, pp. 10.
William G. Telford et al., "Comparative evaluation of several DNA binding dyes in the detection of apoptosisassociated chromatin degradation by flow cytometry", Cytometry, val. 13, No. 2, Jan. 1, 1992 (Jan. 1, 1992 ), pp. 137-143, XP055411284,US ISSN: 0196-4763.

* cited by examiner

*Primary Examiner* — Heidi Reese

(57) ABSTRACT

Provided herein are compounds, enzyme substrates, compositions, kits, uses, and methods for detecting the presence or absence of a caspase enzyme, measuring the activity of a caspase enzyme, or detecting the presence or absence of apoptosis. The detection or measurement can occur through intracellular cleavage of a compound or enzyme substrate, which can lead to an increase in fluorescence, e.g., in the violet or red channel, through liberation of a nucleic acid binding dye from a peptide, such as liberation of a DNA-binding dye from a negatively charged peptide comprising a sequence recognized and cleaved by a caspase.

10 Claims, 14 Drawing Sheets
Specification includes a Sequence Listing.

DMSO Control            Staurosporine

DMSO Control            Staurosporine

DMSO Control

Staurosporine

METHODS AND COMPOSITIONS FOR DETECTING OR MEASURING CASPASES OR APOPTOSIS

CROSS-REFERENCE

This application is a 371 National Stage of PCT/US2017/038444 filed Jun. 21, 2017, which claims the benefit under 35 U.S.C. § 119(e) of U.S. Provisional Application No. 62/353,892, filed Jun. 23, 2016. The entire contents of the aforementioned applications are incorporated by reference herein.

SEQUENCE LISTING

This application hereby incorporates by reference the material of the electronic Sequence Listing filed concurrently herewith. The material in the electronic Sequence Listing is submitted as a text (.txt) file in ASCII format entitled "LT01158PCT_SL.txt" created on Jun. 9, 2017 which has a file size of 12,432 bytes, and is herein incorporated by reference in its entirety.

FIELD OF THE INVENTION

The present invention relates to methods and compositions for detecting or measuring caspases or apoptosis, including fluorogenic enzyme substrates.

BRIEF SUMMARY OF THE INVENTION

The present disclosure provides compositions and methods for intracellular assay, detection, and quantitation of apoptotic events. In some embodiments, new fluorogenic probes for detecting or measuring caspase enzyme activity or apoptosis are provided, which can facilitate detection of caspase activity or apoptosis in the violet or red channels of fluorescence detection equipment such as flow cytometer, plate reader, or fluorescence microscope. The new fluorogenic probes can free up other channels (e.g., orange, yellow, green, and cyan) for other uses, allowing for greater experimental throughput or flexibility in experimental design, or at least provide the public with a useful choice.

In some embodiments, the fluorogenic probes comprise nucleic acid binding dyes attached either directly or indirectly to a peptide substrate moiety. In certain embodiments, the enzyme substrate moiety, when conjugated to the dye, reduces or eliminates the functionality of the dye. In certain embodiments, the substrate moiety may serve as a steric block such that, when attached to the dye, the substrate moiety interferes with the functionality of the dye. In another embodiment, the substrate moiety may carry a net positive or net negative charge so that upon conjugation to the dye, the substrate moiety alters the amount and/or nature of the charge on the dye that is associated with the functionality of the dye.

In some embodiments, new fluorogenic probes for detecting or measuring caspase enzyme activity or apoptosis are provided, which have an extra aspartic acid compared to a standard peptide substrate, e.g., a standard substrate for one or more of caspases 1, 8, or 9. The addition of the aspartic acid can increase the negative charge of the substrate moiety without interfering with substrate recognition and decreases the binding capacity of reagent to DNA while maintaining the binding capacity of the liberated dye after enzymatic cleavage. Further advantages of the extra aspartic acid include, lower background signal and increased impermeability to cross the nuclear membrane before cleavage resulting in localization of the reagent in the cytoplasm.

Certain embodiments provide a method for detecting the presence or absence of a caspase enzyme in a cell or mixture of cells, measuring the activity of a caspase enzyme in a cell or mixture of cells, or detecting the presence or absence of apoptosis in a cell or mixture of cells, the method comprising the steps of:

a) incubating the cell or mixture of cells with a compound of structural formula (I):

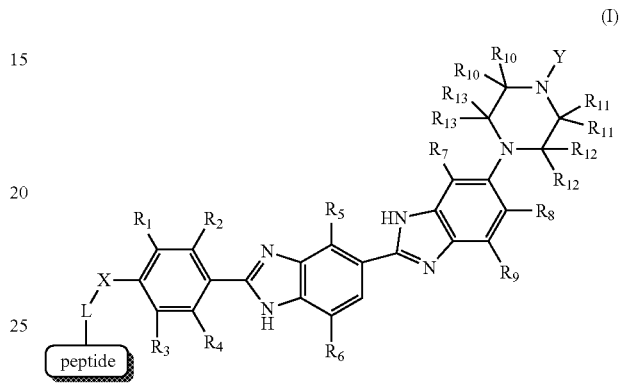

wherein

Y is alkyl or substituted alkyl;

X is —CH$_2$—, —O—, or —N(R)—, wherein R is H, halogen, alkyl or substituted alkyl;

L is a linker; and each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, halogen, alkyl or substituted alkyl; and b) providing a stimulus to the cell or mixture of cells to elicit a fluorescent signal; and c) measuring the fluorescent signal, whereby the presence or absence of the caspase enzyme is detected, the activity of the caspase enzyme is measured, or the presence or absence of apoptosis is detected.

In certain embodiments of the methods provided herein, a) each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, halogen, or alkyl; b) each $R_1$, $R_2$, $R_3$, $R_4$, $R_5$, $R_6$, $R_7$, $R_9$, $R_{10}$, $R_{11}$, $R_{12}$ and $R_{13}$ is independently H, alkyl, or substituted alkyl; c) each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H or alkyl; d) at least one, two, three, four, five, six, seven, eight, nine, ten, eleven, or twelve of $R_1$, $R_2$, $R_3$, $R_4$, $R_5$, $R_6$, $R_7$, $R_8$, $R_9$, $R_{10}$, $R_{11}$, $R_{12}$ and $R_{13}$ are H; or e) each $R_1$, $R_2$, $R_3$, $R_4$, $R_5$, $R_6$, $R_7$, $R_8$, $R_9$, $R_{10}$, $R_{11}$, $R_{12}$ and $R_{11}$ is H.

In certain embodiments of the methods provided herein, a) X is —N(R)— wherein R is H, halogen, alkyl, or substituted alkyl; b) X is —N(R)— wherein R is alkyl or substituted alkyl; c) X is —N(R)— wherein R is alkyl; d) X is —N(R)— wherein R is methyl, ethyl, propyl, or isopropyl; e) X is —N(R)— wherein R is methyl or ethyl; or f) X is —N(CH$_3$)—.

In certain embodiments of the methods provided herein, a) Y is alkyl; b) Y is methyl, ethyl, propyl, or isopropyl; c) Y is methyl or ethyl; or d) Y is methyl.

In certain embodiments of the methods provided herein, the compound is selected from the group consisting of:

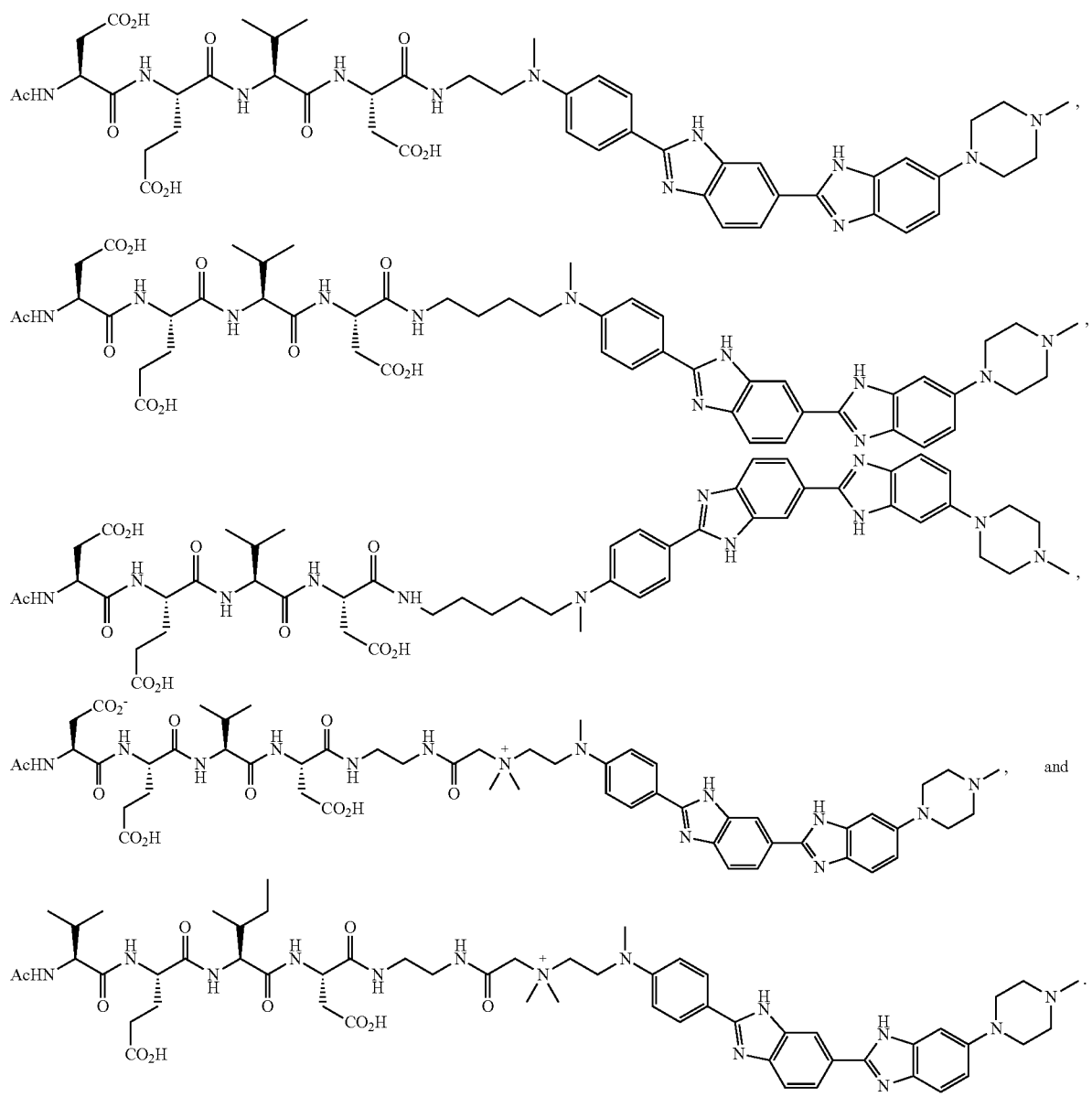

Certain embodiments provide a method for detecting the presence or absence of a caspase enzyme in a cell or mixture of cells, measuring the activity of a caspase enzyme in a cell or mixture of cells, or detecting the presence or absence of apoptosis in a cell or mixture of cells, the method comprising the steps of:

a) incubating the cell or mixture of cells with a compound of structural formula (II):

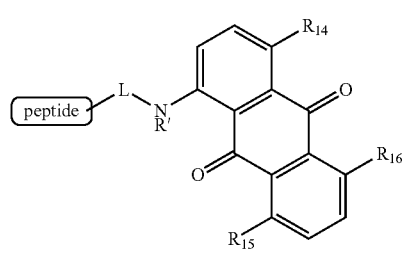

(II)

wherein $R_{14}$, $R_{15}$, and $R_{16}$ are each independently —OH or —NH$_2$;

R' is H, alkyl or substituted alkyl; and

L is a linker; and b) providing a stimulus to the cell or mixture of cells to elicit a fluorescent signal; and c) measuring the fluorescent signal, whereby the presence or absence of the caspase enzyme is detected, the activity of the caspase enzyme is measured, or the presence or absence of apoptosis is detected.

In certain embodiments of the methods provided herein, a) $R_{14}$ is —OH; b) $R_{15}$ is —OH; c) $R_{16}$ is —NH$_2$; d) $R_{14}$ is —OH and $R_{15}$ is —OH; e) $R_{14}$ is —OH and $R_{16}$ is —NH$_2$; f) $R_{15}$ is —OH and $R_{16}$ is —NH$_2$; or g) $R_{14}$ is —OH, $R_{15}$ is —OH, and $R_{16}$ is —NH$_2$.

In certain embodiments of the methods provided herein, a) R' is H or alkyl; b) R' is H or methyl, ethyl, propyl, or isopropyl; or c) R' is H.

In certain embodiments of the methods provided herein, the compound is selected from the group consisting of:

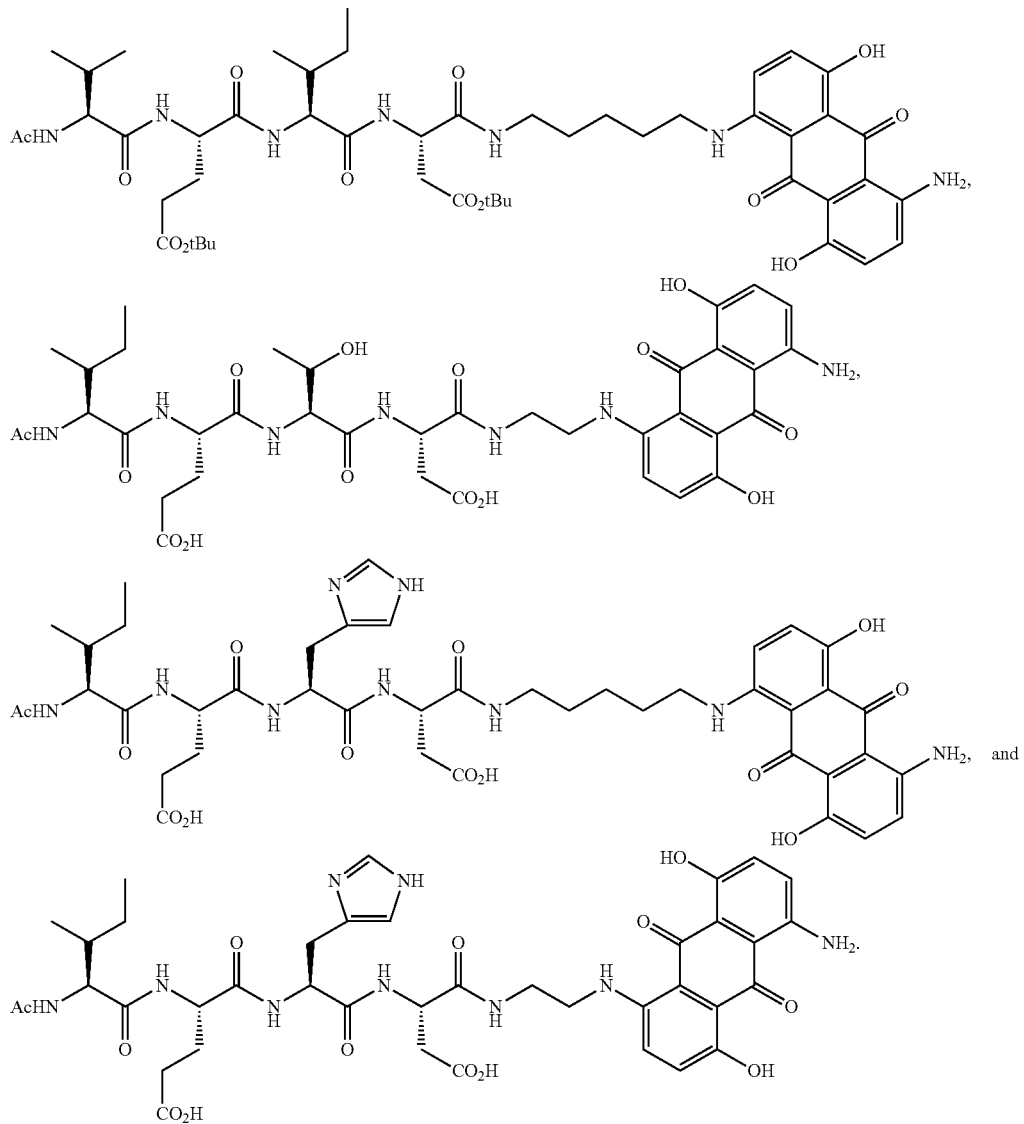

Certain embodiments provide a method for detecting the presence or absence of a caspase enzyme in a cell or mixture of cells, measuring the activity of a caspase enzyme in a cell or mixture of cells, or detecting the presence or absence of apoptosis in a cell or mixture of cells, the method comprising the steps of:

a) incubating the cell or mixture of cells with a compound comprising a peptide and a fluorogenic dye and having structural formula (III):

peptide-L-dye (III);

wherein:
the peptide comprises a sequence of $DX_2EX_1D$ (SEQ ID NO. 8) or $DX_2VX_1D$ (SEQ ID NO. 20), wherein $X_2$ is W, Y, I, L, or V, and $X_1$ is any amino acid;
L is a linker; and
dye is the fluorogenic dye, wherein the fluorogenic dye is able to associate with a nucleic acid when not linked to the peptide, and is able to emit a fluorescent signal upon excitation when associated with a nucleic acid;

b) providing a stimulus to the cell or mixture of cells to elicit a fluorescent signal; and c) measuring the fluorescent signal, whereby the presence or absence of the caspase enzyme is detected, the activity of the caspase enzyme is measured, or the presence or absence of apoptosis is detected.

In certain embodiments of the methods provided herein, the fluorogenic dye is a rhodamine, dibenzorhodamine, thiazole, thiazole orange, coumarin, or cresyl violet; optionally wherein the fluorogenic dye is NUCVIEW™488 (Biotium. Inc., Hayward, Calif.) or a rhodamine 110 (R110) or rhodamine 600 (R600), the R600 optionally comprising a silicon, germanium, or tin atom at the 10 position of its xanthene ring system; further optionally wherein the R110 is N-octyloxycarbonyl-R110, N'-morpholinecarbonyl-R110, or the R600 is SiR600 or 2-Me SiR600.

In certain embodiments of the methods provided herein, the fluorogenic dye is a compound having structural formula (IV):

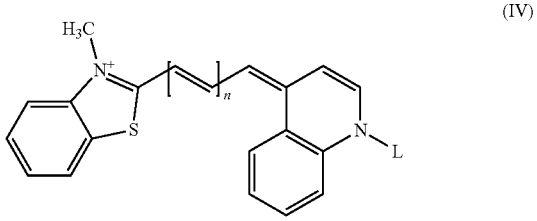

(IV)

wherein:
n=0 or 1; and
L is a linker; and
the peptide is DX$_2$EX$_1$D (SEQ ID NO. 8), wherein X$_2$ is W, Y, I, L, or V, and X$_1$ is any amino acid.

In certain embodiments of any of the methods provided herein, the activity of the caspase enzyme is measured.

In certain embodiments of any of the methods provided herein, the presence or absence of apoptosis is detected.

In certain embodiments of any of the methods provided herein, the presence or absence of the caspase enzyme is detected.

In certain embodiments of any of the methods provided herein, the methods further comprise measuring a fluorescent signal before delivering the compound to the cell or mixture of cells.

In certain embodiments of any of the methods provided herein, the compound is cleaved by a caspase enzyme. In certain embodiments, the caspase enzyme is caspase-1, caspase-3, caspase-6, caspase-7, caspase-8 or caspase-9.

In certain embodiments of any of the methods provided herein, the methods further comprise the step of incubating the cell or mixture of cells with an apoptosis inducer.

In certain embodiments of any of the methods provided herein, the methods further comprise the step of incubating the cell or mixture of cells with a caspase inhibitor.

In certain embodiments of any of the methods provided herein, the fluorescent signal is detected by flow cytometry. In certain embodiments, the fluorescent signal is detected by fluorescence microscopy.

In certain embodiments of any of the methods provided herein, the peptide comprises an amino acid sequence of:

a) X$_2$EX$_1$D (SEQ ID NO. 5), wherein X$_2$ is W, Y, I, L, D, or V, and X$_1$ is any amino acid;
b) X$_3$DEX$_1$D (SEQ ID NO. 6), wherein X$_3$ is V or L and X$_1$ is any amino acid;
c) DX$_1$VD (SEQ ID NO. 7), wherein X$_1$ is any amino acid;
d) DX$_2$EX$_1$D (SEQ ID NO. 8), wherein X$_2$ is W, Y, I, L, or V, and X$_1$ is any amino acid; or
e) DX$_2$VX$_1$D (SEQ ID NO. 20), wherein X$_2$ is W, Y, I, L, or V, and X$_1$ is any amino acid; optionally wherein the amino acid sequence of a), b), c), d), or e) is the entire amino acid sequence of the peptide or the C-terminal amino acid sequence of the peptide.

In certain embodiments of any of the methods provided herein, the peptide comprises an amino acid sequence of WEHD (SEQ ID NO. 9), YVAD (SEQ ID NO. 10), YVHD (SEQ ID NO. 11), VDVAD (SEQ ID NO. 12), LEHD (SEQ ID NO. 2), IETD (SEQ ID NO. 13), VEID (SEQ ID NO. 14), DEVD (SEQ ID NO. 1), LEVD (SEQ ID NO. 15), or AEVD (SEQ ID NO. 16), optionally wherein the amino acid sequence is the entire amino acid sequence of the peptide or the C-terminal amino acid sequence of the peptide.

In certain embodiments of any of the methods provided herein, the peptide is a substrate for cleavage by at least one caspase, has a length of 5 or more amino acids, and comprises an aspartic acid in the P$_5$ position.

In certain embodiments of any of the methods provided herein, the peptide comprises an amino acid sequence of DIETD (SEQ ID NO. 17), DLEHD (SEQ ID NO. 18), or DYVAD (SEQ ID NO. 19), optionally wherein the amino acid sequence is the entire amino acid sequence of the peptide or the C-terminal amino acid sequence of the peptide.

In certain embodiments of any of the methods provided herein, the peptide:

a) further comprises one or more additional amino acid residues C-terminally;
b) further comprises one or more additional amino acid residues N-terminally;
c) further comprises one or more additional amino acid residues both C-terminally and N-terminally;
d) further comprises 1 to 100, 1 to 50, 1 to 20, 1 to 10, 1 to 5, 5, 4, 3, 2, or 1 additional amino acid residues C-terminally;
e) further comprises 1 to 100, 1 to 50, 1 to 20, 1 to 10, 1 to 5, 5, 4, 3, 2, or 1 additional amino acid residues N-terminally; or
f) further comprises 1 to 100, 1 to 50, 1 to 20, 1 to 10, 1 to 5, 5, 4, 3, 2, or 1 additional amino acid residues both C-terminally and N-terminally.

In certain embodiments of any of the methods provided herein, the peptide has a sequence with a total length of 4 to 200 amino acid residues, 4 to 100 amino acid residues, 4 to 50 amino acid residues, 5 to 200 amino acid residues, 5 to 100 amino acid residues, 5 to 50 amino acid residues, 20 to 50 amino acid residues, or 4, 5, 6, 7, 8, 9, 10, 11, 12, 13, 14, 15, 16, 17, 18, 19, or 20 amino acid residues.

In certain embodiments of any of the methods provided herein, the peptide comprises an N-terminal acyl. In certain embodiments, the N-terminal acyl is an acetyl or carboxybenzyl.

In certain embodiments of any of the methods provided herein, L is:

a) —N(R$_{N1}$)—[CH$_2$]$_n$—, wherein n ranges from 1 to 10 and R$_{N1}$ is H or optionally substituted C$_{1-6}$ alkyl;
b) —N(R$_{N1}$)-L$_a$-, wherein L$_a$ is a C$_{2-10}$ alkylene optionally interrupted by one or both of —N(R$_{N1}$)—C(O)— or —N$^+$(R$_{N2}$)$_2$—, wherein each R$_{N1}$ is independently H or optionally substituted C$_{1-6}$ alkyl and each R$_{N2}$ is independently an optionally substituted C$_{1-6}$ alkyl;
c) —C(O)—[CH$_2$]$_n$—, wherein n ranges from 1 to 10;
d) —N(R$_{N1}$)—[CH$_2$]$_n$—C(O)—, wherein n ranges from 1 to 10 and R$_{N1}$ is H or optionally substituted C$_{1-6}$ alkyl;
e) —C(O)—[CH$_2$]$_n$—C(O)—, wherein n ranges from 1 to 10;
f) —[CH$_2$]—N$^+$(R$_{N2}$)$_2$—[CH$_2$]—, wherein each R$_{N2}$ is independently an optionally substituted C$_{1-6}$ alkyl;
g) —NH—[CH$_2$]$_2$—;
h) —NH—[CH$_2$]$_4$—;
i) —NH—[CH$_2$]$_5$—; or
j) —NH—[CH$_2$]$_2$—NH—C(O)—CH$_2$—N(CH$_3$)$_2$—[CH$_2$]$_2$—.

In certain embodiments of any of the methods provided herein, the methods further comprise incubating the cell or mixture of cells with at least one, two, three, or four additional fluorescent molecules, wherein the at least one, two, three, or four additional fluorescent molecules are spectrally distinguishable from at least one of the compound of structural formula (I) or the compound of structural formula (II), and measuring fluorescent signals from the at least one, two, three, or four additional fluorescent molecules.

In certain embodiments, (i) the cell or mixture of cells is incubated with a compound of structural formula (I) and the at least one, two, three, or four additional fluorescent molecules have near infrared, red, orange, yellow, green, or cyan emission maxima; or (ii) the cell or mixture of cells is incubated with a compound of structural formula (II) and the at least one, two, three, or four additional fluorescent molecules have near infrared, yellow, green, cyan, blue, or violet emission maxima.

In certain embodiments, the cell or mixture of cells expresses or comprises a construct encoding at least one, two, three, or four fluorescent proteins, optionally wherein at least one, two, three, or four of the fluorescent proteins are fusion proteins, and the at least one, two, three, or four fluorescent proteins are spectrally distinguishable from at least one of the compound of structural formula (I) or the compound of structural formula (II).

In certain embodiments, (i) the cell or mixture of cells is incubated with a compound of structural formula (I) and the at least one, two, three, or four fluorescent proteins have near infrared, red, orange, yellow, green, or cyan emission maxima; or (ii) the cell or mixture of cells is incubated with a compound of structural formula (II) and the at least one, two, three, or four additional fluorescent proteins have near infrared, yellow, green, cyan, or blue emission maxima.

Certain embodiments provide compounds selected from the group consisting of:

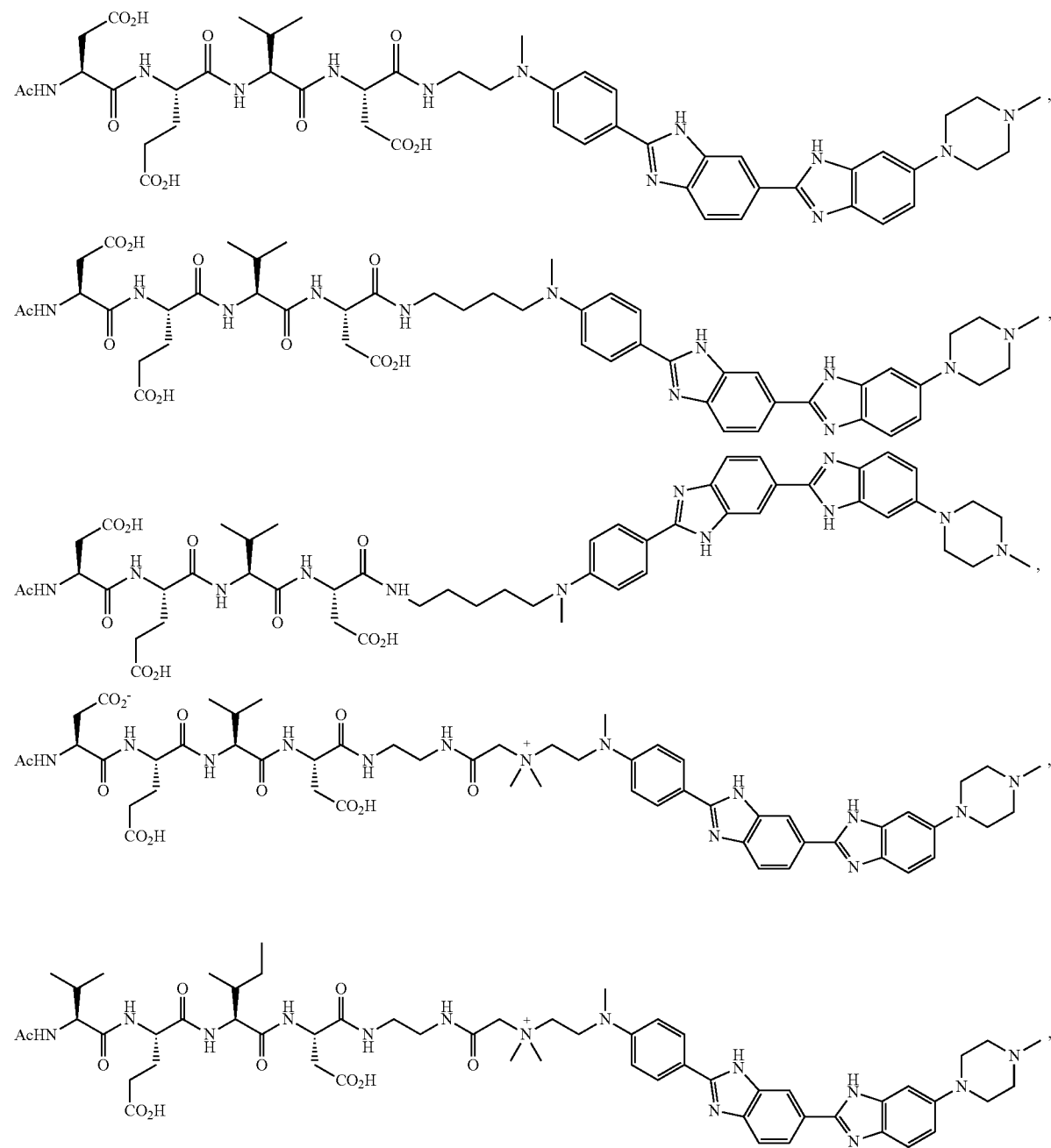

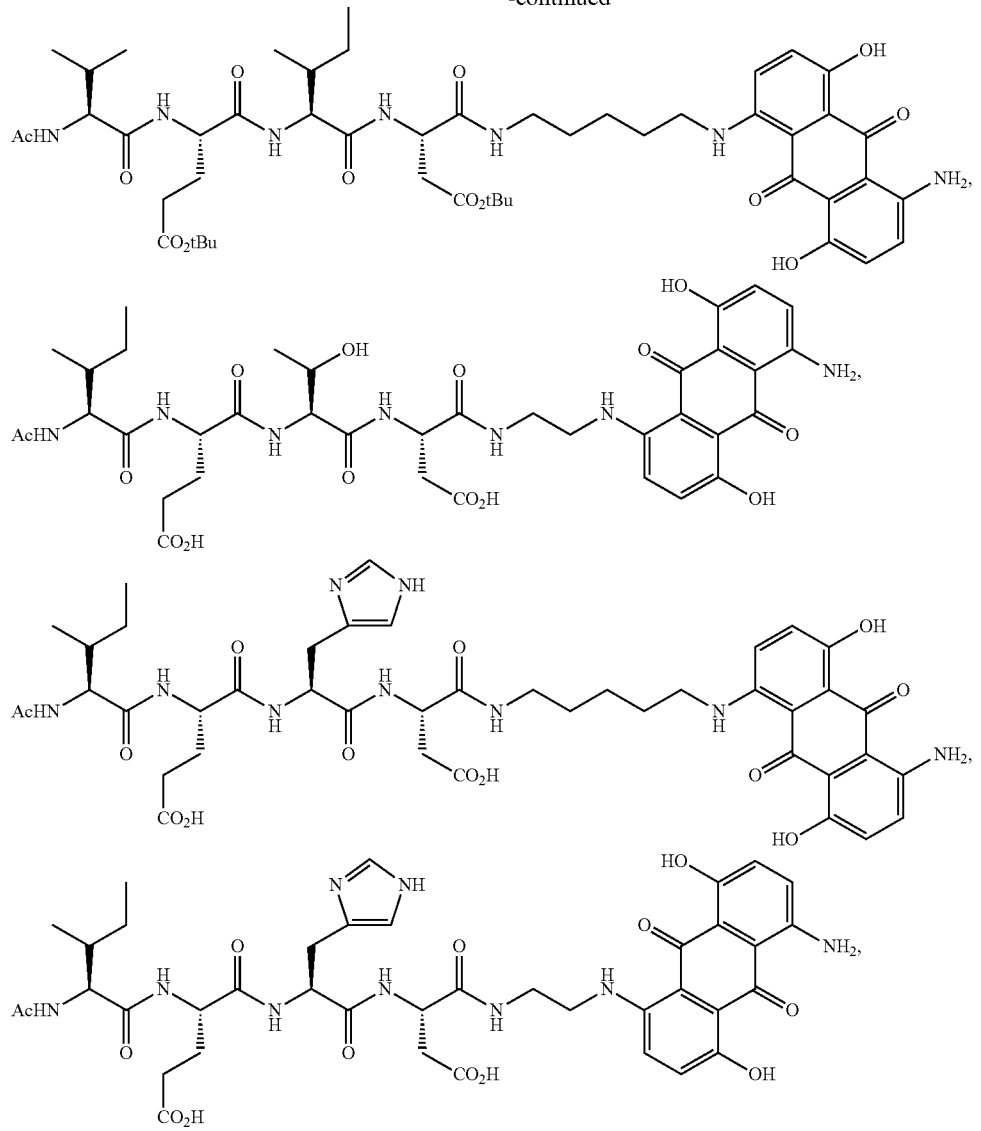

or a pharmaceutically acceptable salt thereof.

Certain embodiments provide enzyme substrates comprising:

a) a fluorogenic dye moiety of structural formula (I):

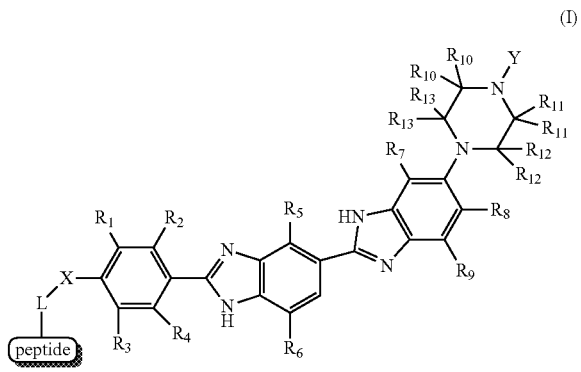

(I)

wherein

Y is alkyl or substituted alkyl,

X is —$CH_2$—, —O—, or —N(R)—, wherein R is H, halogen, alkyl or substituted alkyl L is a linker; and each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, halogen, alkyl or substituted alkyl; and b) a peptide covalently attached to the fluorogenic dye moiety through the linker L.

In certain embodiments, a) each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, halogen, or alkyl; b) each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, alkyl, or substituted alkyl; c) each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H or alkyl; d) at least one, two, three, four, five, six, seven, eight, nine, ten, eleven, or twelve of $R_1$, $R_2$, $R_3$, $R_4$, $R_5$, $R_6$, $R_7$, $R_8$, $R_9$, $R_{10}$, $R_{11}$, $R_{12}$ and $R_{13}$ are H; or e) each $R_1$, $R_2$, $R_3$, $R_4$, $R_5$, $R_6$, $R_7$, $R_8$, $R_9$, $R_{10}$, $R_{11}$, $R_{12}$ and $R_{13}$ is H.

In certain embodiments, a) X is —N(R)— wherein R is H, halogen, alkyl, or substituted alkyl; b) X is —N(R)— wherein R is alkyl or substituted alkyl; c) X is —N(R)— wherein R is alkyl; d) X is —N(R)— wherein R is methyl, ethyl, propyl, or isopropyl; e) X is —N(R)— wherein R is methyl or ethyl; or f) X is —N(CH$_3$)—.

In certain embodiments, a) Y is alkyl; b) Y is methyl, ethyl, propyl, or isopropyl; c) Y is methyl or ethyl; or d) Y is methyl.

Certain embodiments provide enzyme substrates comprising:

a) a fluorogenic dye moiety of structural formula (II):

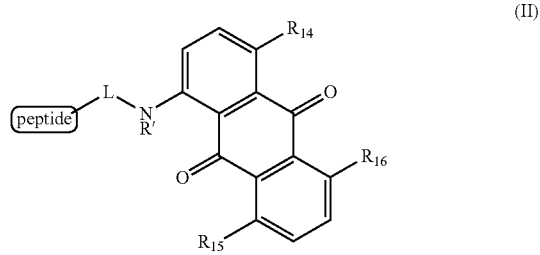

(II)

wherein
R$_{14}$, R$_{15}$, and R$_{16}$ are each independently —OH or —NH$_2$;
R' is H, alkyl or substituted alkyl; and
L is a linker; and
b) a peptide covalently attached to the fluorogenic dye moiety through the linker L.

In certain embodiments, a) R$_{14}$ is —OH; b) R$_{15}$ is —OH; c) R$_{16}$ is —NH$_2$; d) R$_{14}$ is —OH and R$_{15}$ is —OH; e) R$_{14}$ is —OH and R$_{16}$ is —NH$_2$; f) R$_{15}$ is —OH and R$_{16}$ is —NH$_2$; or g) R$_{14}$ is —OH, R$_{15}$ is —OH, and R$_{16}$ is —NH$_2$.

In certain embodiments, a) R' is H or alkyl; b) R' is H or methyl, ethyl, propyl, or isopropyl; or c) R' is H.

In certain embodiments of any of the enzyme substrates provided herein, the peptide comprises an amino acid sequence of:
a) X$_2$EX$_1$D (SEQ ID NO. 5), wherein X$_2$ is W, Y, I, L, D, or V, and X$_1$ is any amino acid;
b) X$_3$DEX$_1$D (SEQ ID NO. 6), wherein X$_3$ is V or L and X$_1$ is any amino acid;
c) DX$_1$VD (SEQ ID NO. 7), wherein X$_1$ is any amino acid;
d) DX$_2$EX$_1$D (SEQ ID NO. 8), wherein X$_2$ is W, Y, I, L, or V, and X$_1$ is any amino acid; or
e) DX$_2$VX$_1$D (SEQ ID NO. 20), wherein X$_2$ is W, Y, I, L, or V, and X$_1$ is any amino acid; optionally wherein the amino acid sequence of a), b), c), d), or e) is the entire amino acid sequence of the peptide or the C-terminal amino acid sequence of the peptide.

In certain embodiments of any of the enzyme substrates provided herein, the peptide comprises or is attached to a caspase cleavage site.

In certain embodiments of any of the enzyme substrates provided herein, the peptide comprises the amino acid sequence WEHD (SEQ ID NO. 9), YVAD (SEQ ID NO. 10), YVHD (SEQ ID NO. 11), VDVAD (SEQ ID NO. 12), LEHD (SEQ ID NO. 2), IETD (SEQ ID NO. 13), VEID (SEQ ID NO. 14), DEVD (SEQ ID NO. 1), LEVD (SEQ ID NO. 15), or AEVD (SEQ ID NO. 16), optionally wherein the amino acid sequence is the entire amino acid sequence of the peptide or the C-terminal amino acid sequence of the peptide.

In certain embodiments of any of the enzyme substrates provided herein, the peptide is a substrate for cleavage by at least one caspase, has a length of 5 or more amino acids, and comprises an aspartic acid in the P$_5$ position.

Certain embodiments provide enzyme substrates comprising a peptide and a fluorogenic dye and having structural formula (III):

peptide-L-dye (III):

wherein:
the peptide comprises a sequence of DX$_2$EX$_1$D (SEQ ID NO. 8) or DX$_2$VX$_1$D (SEQ ID NO. 20), wherein X$_2$ is W, Y, I, L, or V, and X$_1$ is any amino acid;
L is a linker; and
dye is the fluorogenic dye, wherein the fluorogenic dye is able to emit a fluorescent signal upon excitation when free from the peptide.

In certain embodiments, the fluorogenic dye is a rhodamine, dibenzorhodamine, thiazole, thiazole orange, coumarin, or cresyl violet; optionally wherein the fluorogenic dye is NUCVIEW$^H$488 (Biotium, Inc., Hayward, Calif.) or a rhodamine 110 (R110) or rhodamine 600 (R600), the R600 optionally comprising a silicon, germanium, or tin atom at the 10 position of its xanthene ring system; further optionally wherein the R110 is N-octyloxycarbonyl-R110, N'-morpholinecarbonyl-R110, or the R600 is SiR600 or 2-Me SiR600.

In certain embodiments, the fluorogenic dye is a compound having structural formula (IV):

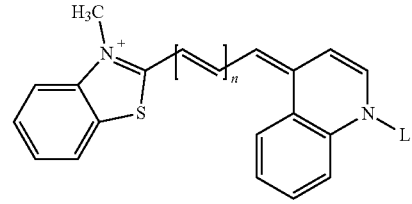

(IV)

wherein:
n=0 or 1; and
L is a linker; and
the peptide is DX$_2$EX$_1$D (SEQ ID NO. 8), wherein X$_2$ is W, Y, I, L, or V, and X$_1$ is any amino acid.

In certain embodiments of any of the enzyme substrates provided herein, the peptide comprises the amino acid sequence of DIETD (SEQ ID NO. 17), DLEHD (SEQ ID NO. 18), or DYVAD (SEQ ID NO. 19), optionally wherein the amino acid sequence is the entire amino acid sequence of the peptide or the C-terminal amino acid sequence of the peptide.

In certain embodiments of any of the enzyme substrates provided herein, the peptide:
a) further comprises one or more additional amino acid residues C-terminally;
b) further comprises one or more additional amino acid residues N-terminally;
c) further comprises one or more additional amino acid residues both C-terminally and N-terminally;
d) further comprises 1 to 100, 1 to 50, 1 to 20, 1 to 10, 1 to 5, 5, 4, 3, 2, or 1 additional amino acid residues C-terminally;
e) further comprises 1 to 100, 1 to 50, 1 to 20, 1 to 10, 1 to 5, 5, 4, 3, 2, or 1 additional amino acid residues N-terminally; or f) further comprises 1 to 100, 1 to 50, 1 to 20, 1 to 10, 1 to 5, 5, 4, 3, 2, or 1 additional amino acid residues both C-terminally and N-terminally.

In certain embodiments of any of the enzyme substrates provided herein, the peptide has a sequence with a total length of 4 to 200 amino acid residues, 4 to 100 amino acid residues, 4 to 50 amino acid residues, 5 to 200 amino acid residues, 5 to 100 amino acid residues, 5 to 50 amino acid residues, 20 to 50 amino acid residues, or 4, 5, 6, 7, 8, 9, 10, 11, 12, 13, 14, 15, 16, 17, 18, 19, or 20 amino acid residues.

In certain embodiments of any of the enzyme substrates provided herein, the peptide comprises a protected amino acid side-chain.

In certain embodiments of any of the enzyme substrates provided herein, the linker is attached to the peptide at a side-chain of an amino acid, an amino terminus of an amino acid or a carboxy terminus of an amino acid.

In certain embodiments of any of the enzyme substrates provided herein, L is:

a) —N($R_{N1}$)—[$CH_2$]$_n$—, wherein n ranges from 1 to 10 and $R_{N1}$ is H or optionally substituted $C_{1-6}$ alkyl;

b) —N($R_{N1}$)-$L_a$-, wherein La is a $C_{2-10}$ alkylene optionally interrupted by one or both of —N($R_{N1}$)—C(O)— or —N$^+$($R_{N2}$)$_2$—, wherein each $R_{N1}$ is independently H or optionally substituted $C_{1-6}$ alkyl and each $R_{N2}$ is independently an optionally substituted $C_{1-6}$ alkyl;

c) —C(O)—[$CH_2$]$_n$—, wherein n ranges from 1 to 10;

d) —N($R_{N1}$)—[$CH_2$]—C(O)—, wherein n ranges from 1 to 10 and $R_{N1}$ is H or optionally substituted $C_{1-6}$ alkyl;

e) —C(O)—[$CH_2$]$_n$—C(O)—, wherein n ranges from 1 to 10;

f) —[$CH_2$]n-$N^{+(R}$$_{N2}$)$_2$—[$CH_2$]$_n$—, wherein each $R_{N2}$ is independently an optionally substituted $C_{1-6}$ alkyl;

g) —NH—[$CH_2$]$_2$—;

h) —NH—[$CH_2$]$_4$—;

i) —NH—[$CH_2$]$_5$—; or j) —NH—[$CH_2$]$_2$—NH—C(O)—$CH_2$—N($CH_3$)$_2$—[$CH_2$]$_2$—.

In certain embodiments of any of the enzyme substrates provided herein, the enzyme substrate is covalently attached to a solid support.

Certain embodiments provide kits for detecting the presence or absence of a caspase enzyme in a cell or mixture of cells, measuring activity of a caspase enzyme within a cell or a mixture of cells, or detecting the presence or absence of apoptosis, the kit comprising:

a) any one of the compounds or enzyme substrates provided herein;

b) at least one of an organic solvent;

c) a desiccant; and d) optionally, instructions for use according to any one of the methods provided herein.

In certain embodiments of the kits provided herein, the compound or enzyme substrate is of structural formula (I):

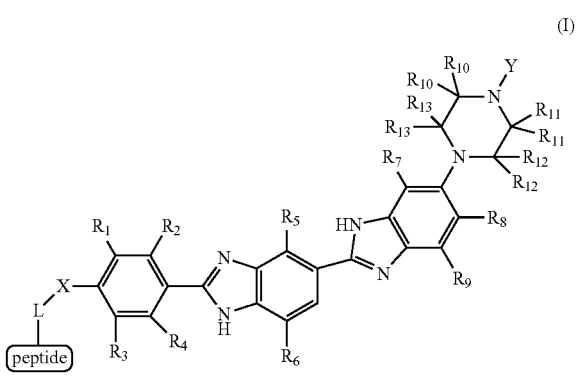

wherein

Y is alkyl or substituted alkyl;

X is —$CH_2$—, —O—, or —N(R)—, wherein R is H, halogen, alkyl or substituted alkyl;

L is a linker; and each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, halogen, alkyl or substituted alkyl.

In certain embodiments of the kits provided herein, the compound is selected from the group consisting of:

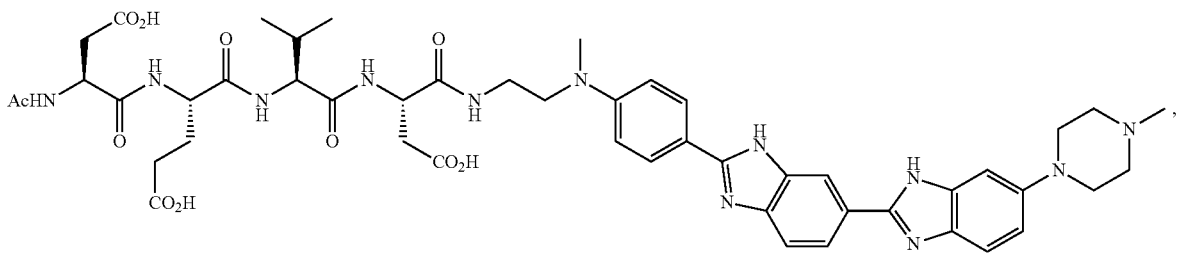

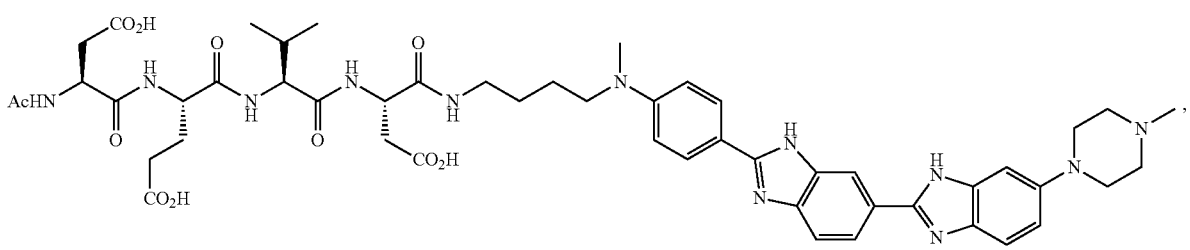

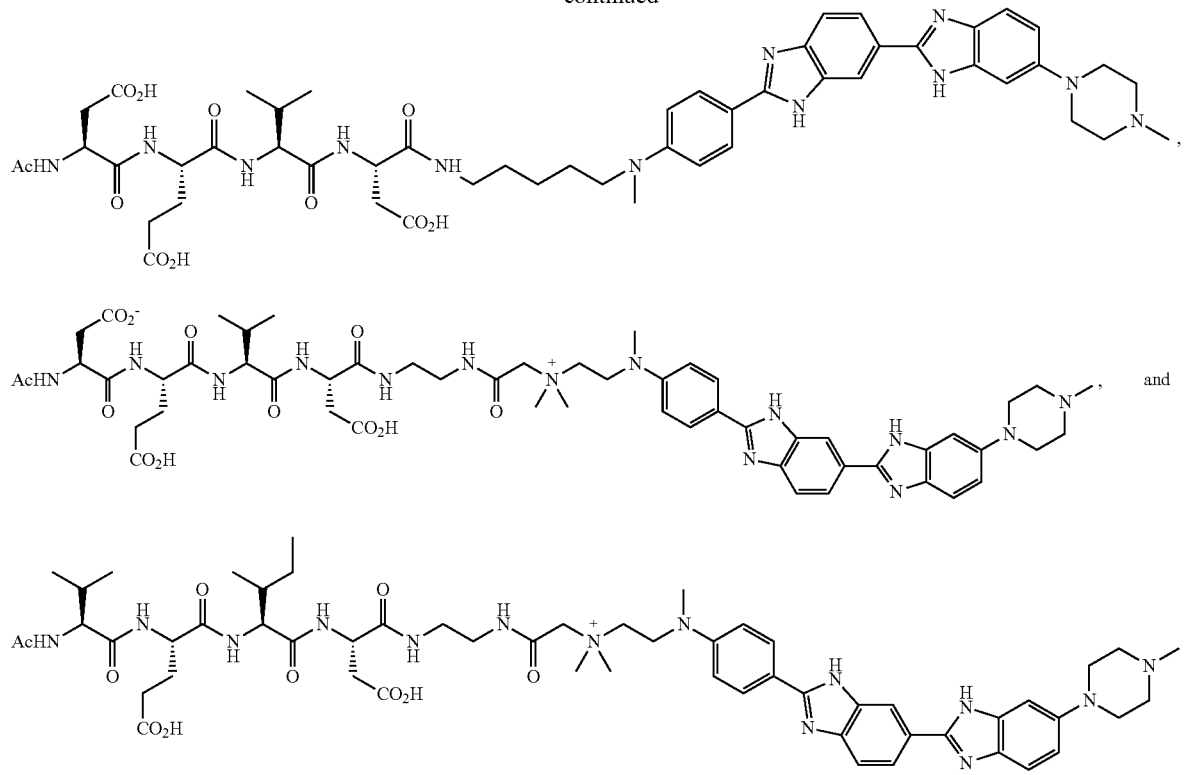
In certain embodiments of the kits provided herein, the compound is a compound of structural formula (II):
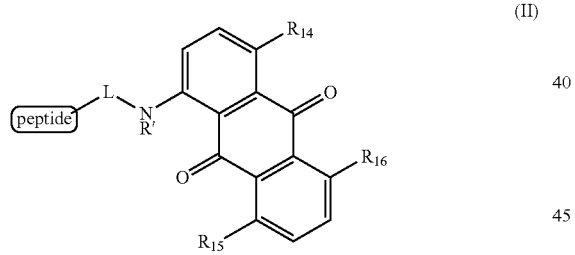
wherein
$R_{14}$, $R_{15}$, and $R_{16}$ are each independently —OH or —$NH_2$;
R' is H, alkyl or substituted alkyl; and
L is a linker.
In certain embodiments of the kits provided herein, the compound is selected from the group consisting of:
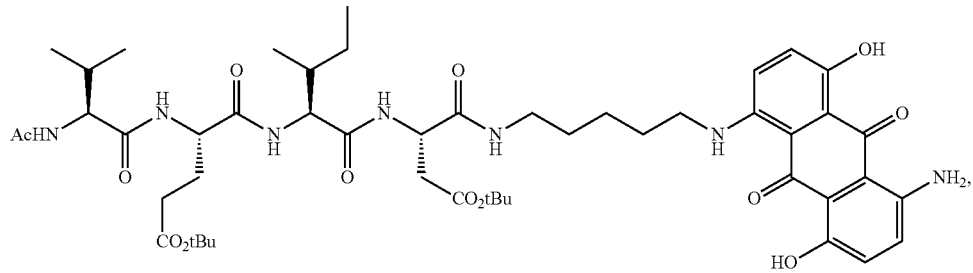

-continued

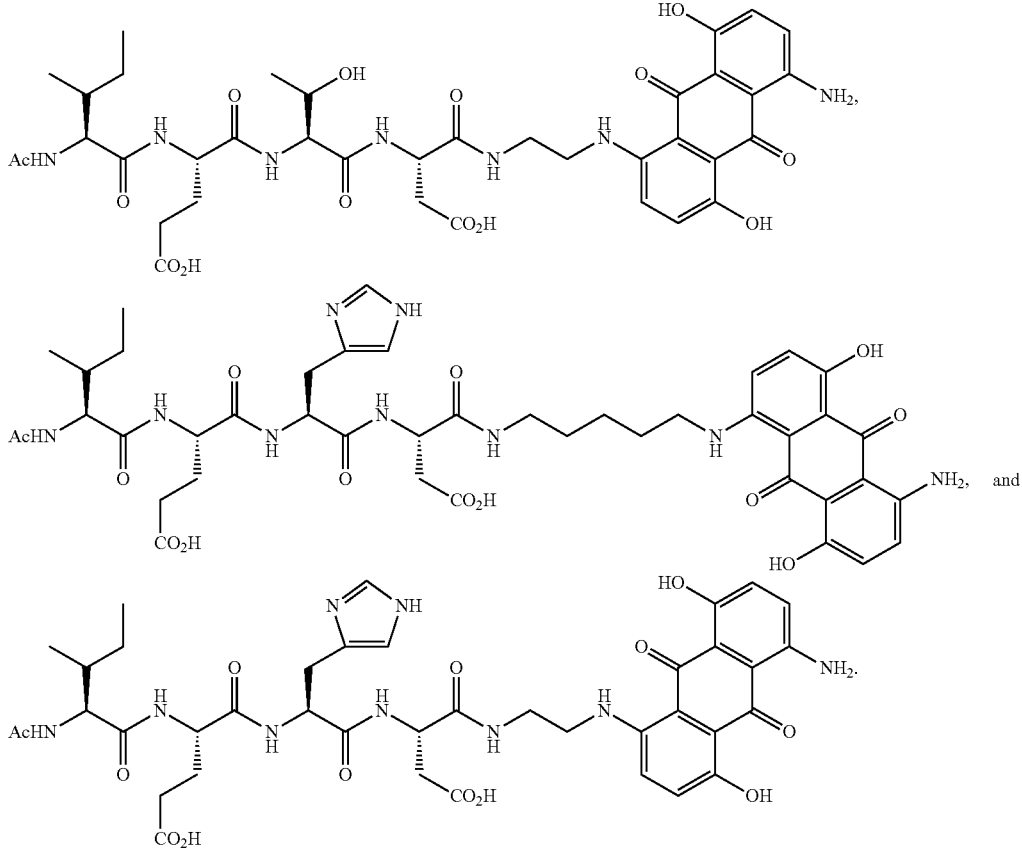

In certain embodiments of the kits provided herein, the kits comprise an enzyme substrate comprising a peptide, and the peptide comprises a sequence of $DX_2EX_1D$ (SEQ ID NO. 8) or $DX_2VX_1D$ (SEQ ID NO. 20), wherein $X_2$ is W, Y, I, L, or V, and $X_1$ is any amino acid.

In certain embodiments of the kits provided herein, the organic solvent comprises DMSO.

Certain embodiments provide compositions for detecting the presence or absence of a caspase enzyme, the compositions comprising:

a) one or more of the compounds or enzyme substrates provided herein; and b) a carrier, wherein the one or more of the compounds or enzyme substrates are present in an amount effective to detect the presence or absence of the caspase enzyme.

Certain embodiments provide compositions for detecting the presence or absence of a caspase enzyme, the composition comprising:

(a) one or more of the compounds or enzyme substrates provided herein; and (b) an analyte, wherein the one or more of the compounds or enzyme substrates are present in an amount effective to detect the presence or absence of the caspase enzyme.

Certain embodiments provide compositions for detecting the presence or absence of apoptosis, the compositions comprising:

a) one or more of the compounds or enzyme substrates provided herein; and b) a carrier, wherein the one or more of the compounds or enzyme substrates are present in an amount effective to detect the presence or absence of apoptosis.

Certain embodiments provide compositions for detecting the presence or absence of apoptosis, the composition comprising:

(a) one or more of the compounds or enzyme substrates provided herein; and (b) an analyte, wherein the one or more of the compounds or enzyme substrates are present in an amount effective to detect the presence or absence of apoptosis.

Certain embodiments provide compositions for measuring activity of a caspase enzyme, the compositions comprising:

a) one or more of the compounds or enzyme substrates provided herein; and b) a carrier, wherein the one or more of the compounds or enzyme substrates are present in an amount effective to measure the activity of the caspase enzyme.

Certain embodiments provide compositions for measuring activity of a caspase enzyme, the composition comprising:

(a) one or more of the compounds or enzyme substrates provided herein; and (b) an analyte, wherein the one or more of the compounds or enzyme substrates are present in an amount effective to measure the activity of the caspase enzyme.

In certain embodiments of any of the compositions provided herein, the analyte is a cell and the compound or enzyme substrate is located inside the cell.

In certain embodiments of any of the compositions provided herein, the compound or enzyme substrate is conjugated to a carrier molecule.

Certain embodiments provide for the use of a compound or enzyme substrate provided herein for detecting the presence or absence of a caspase enzyme in a sample, detecting the presence or absence of apoptosis, or measuring activity of a caspase enzyme.

In certain embodiments of the uses provided herein, the caspase enzyme is an intracellular caspase enzyme, or the presence or absence of apoptosis is detected based on whether or to what extent intracellular cleavage of the compound or enzyme substrate occurs.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9D graphically represents a dose-response of Compound 1 and Compound 9 fluorescence to staurosporine concentration ("SS").

DETAILED DESCRIPTION OF THE INVENTION

Figure 1:
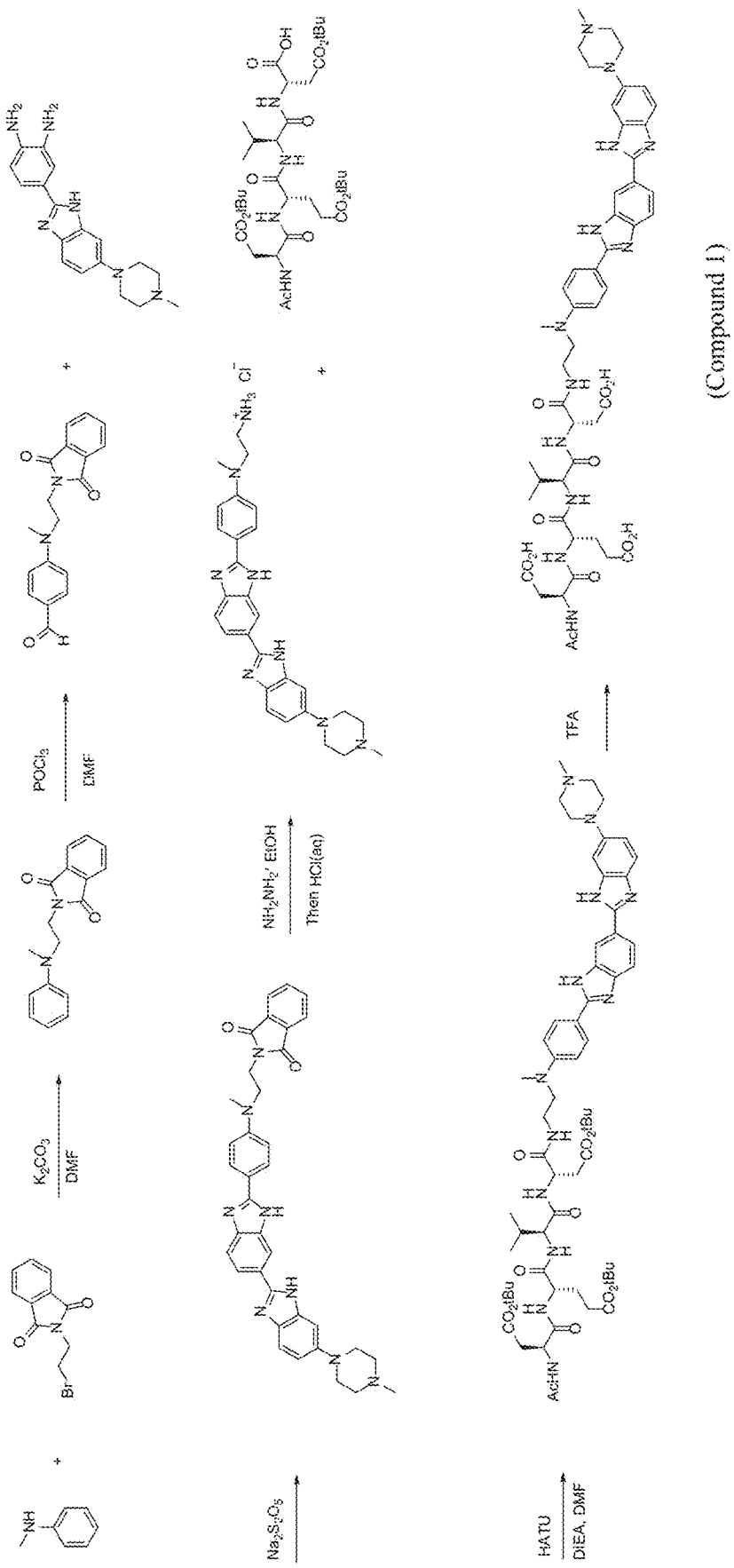
FIG. 1 shows the synthetic scheme for the synthesis of Compound 1 described in Example A.

The caspase family of about 12 cysteine proteases is central to the complex intracellular process of apoptosis, or programmed cell death (Thornberry, *Science* 281:1312-16 (1998)). Caspase activation accompanies the onset of apoptosis which has been implicated in many of the major illnesses without cures. Apoptosis is characterized by a set of morphological and biochemical changes that dying cells undergo, including condensation, shrinkage, margination of chromatin, cytoplasmic vacuolization, increased density, and fragmented nucleic acid with dispersal of nuclear DNA. Caspase-3 has been shown to control both cytoplasmic and nuclear events associated with Fas-mediated apoptosis in vivo (Zheng, *Proc. Natl. Acad. Sci. USA* 95:618-23 (1998)). DNase is activated by caspase in apoptotic cells (Enari, *Nature* 391:43-50 (1998)). Caspase enzymes are good targets for small molecule inhibitors. Caspase inhibitors are potential therapeutics for certain diseases such as Alzheimer's, multiple sclerosis and other neurodegenerative disorders; however, inhibiting caspases may have an accompanying effect of inducing cancers and other cell proliferation effects. It is hoped that understanding the mechanisms of inducing apoptosis and inhibiting caspase activation and activity will yield drugs, e.g. to reduce damage from stroke or myocardial infarction, or prevent and treat cancer.

Peptides which include the amino acid sequence cleaved by caspases are useful probes for assaying caspase activity and thus the onset and progress of apoptosis. (Xanthoudakis, WO 00/73437; Komoriyama WO 96/13607). One critical feature of probe design is to facilitate mammalian cell membrane permeability. For high throughput drug screening it is desirable to mimic the natural state of the living cell. Therefore, the probe should enter the living cell without hypotonic shock, microinjection or other invasive or damaging techniques. For cell based high-throughput screening (HTS), another desirable property is cellular retention of the reporter dye.

Fluorescence based detection methods are important to elucidate intracellular events such as apoptosis. Enzyme substrates labeled with fluorescent dyes have been used to measure protease cleavage activity (Coyler, WO 00/50635; Weber, WO 99/18856). Fluorescent enzymatic assays have been conducted on cell-based screening systems (Dunlay, U.S. Pat. No. 5,989,835; Schroeder, U.S. Pat. No. 5,355, 215) in microtiter plate, high throughput formats (Manian. U.S. Pat. No. 6,130,745; Harootunian, U.S. Pat. No. 5,589, 351; Heffelfinger, U.S. Pat. No. 5,784,152; Taylor, U.S. Pat. No. 6,103,479) and digitized imaging data (Baer, U.S. Pat. No. 5,547,849). Fluorescent dyes which are excited and emit fluorescence at longer wavelengths suitable for molecular biology experiments are discussed in Mao, U.S. Pat. No. 6,130,101; Glazer, U.S. Pat. No. 5,565,554; and Waggoner, U.S. Pat. No. 5,268,486.

Nonetheless, design of new fluorogenic probes for caspase activity or apoptosis is nontrivial because the probes must be cell-permeable, substrates for the intended caspase enzymes, and useful in live-cell experiments. It is generally not simple to predict ab initio that a new compound or class of compounds will meet each of these criteria.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a dye" includes a plurality of dyes and reference to "a cell" includes a plurality of cells and the like.

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components, embodiments in the specification that recite "consisting of" various components are also contemplated as "comprising" or "consisting essentially of" the recited components, and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

DEFINITIONS

Unless stated otherwise, the following terms and phrases as used herein are intended to have the following meanings:

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, "about" refers to a value that is 10% more or less than a stated value, gives results functionally equivalent to the stated value, or rounds to the stated value.

"Or" is used in the inclusive sense, i.e., equivalent to "and/or," unless the context requires otherwise.

"Polypeptide", "protein" and "peptide" are polymers comprised of chains of amino acid monomers linked by amide or disulfide bonds. Polypeptides may be formed by a condensation reaction between the α-carbon carboxyl group of one amino acid and the amino group of another amino acid. Amino acids include the 20 or so that occur naturally and are gene-encoded, as well as analogs of amino acids (common examples include but are not limited to norleucine, selenomethionine, and citrulline). All of the amino acids used in the present invention may be either the D- or L-optical isomer. In addition, other peptidomimetics are also useful (Spatola, (1983) in *Chemistry and Biochemistry of Amino Acids, Peptides, and Proteins*, Weinstein, ed., Marcel Dekker, New York, p. 267). The terminal amino acid at one end of the chain (amino terminal) therefore has an amino group (which can be free or modified, e.g., acylated, such as acetylated or carboxybenzoylated), while the terminal amino acid at the other end of the chain (carboxy terminal) has a carboxyl group (or a derivative thereof, such as derivative in which one of the oxygens has been substituted, such as an ester, amide, acid halide, ketone, aldehyde, or anhydride). As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. An amino terminus may be modified or protected with a variety of functional groups or protecting groups. Similarly, the term "carboxy terminus" refers to the free carboxyl group on the carboxy terminus of a peptide or the backbone carboxyl group of an amino acid at any other location within the peptide. A carboxy terminus may be modified, e.g. as an amide or the other forms mentioned above. The peptides described herein are written with the amino terminus at the left and the carboxyl terminus at the right, forming a sequence of amino acids.

"Amino acids" are represented interchangeably by their common names, their three letter code, or their one letter codes in Table 1 below:

TABLE 1

Amino Acid Abbreviations

| Amino Acid | Three letter | One letter |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |

TABLE 1-continued

Amino Acid Abbreviations

| Amino Acid | Three letter | One letter |
|---|---|---|
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acid residues that are "conservative variants" or "conservative substitutions" for corresponding residues in a reference sequence are those that are physically or functionally similar to the corresponding reference residues, e.g. that have similar size, shape, electric charge, hydrophobicity, hydrophilicity, polarity, reactive chemical properties including the ability to form covalent or hydrogen bonds, and other properties. Particularly preferred conservative variants are those fulfilling the criteria defined for an "accepted point mutation" (Dayhoff et al, (1978) in *Atlas of Protein Sequence and Structure. Suppl.* 3, Natl. Biomed. Res. Foundation, Washington, D.C., chapter 22, pp. 352-54.). Conservative variants of amino acids typically include substitutions within the following groups: I. glycine, alanine, valine, isoleucine, leucine; II, aspartic acid, glutamic acid, asparagine, glutamine; III, serine, threonine; IV, lysine, arginine; V, phenylalanine, tyrosine.

"Homologs" are peptides with substantially identical amino acid sequences which retain the lipid membrane-permeant function and which differ from the preferred sequences mainly or only by conservative amino acid substitutions, for example, substitution of one amino acid for another within the same class above, (e.g. I. valine for glycine or IV, arginine for lysine) or by one or more non-conservative substitutions, deletions, or insertions located at positions of the amino acid sequence which do not destroy the function of the protein. Preferably, such a sequence is at least 85%, and more preferably 90%, and most preferably 95% identical at the amino acid level to the sequence of the peptide to which it is being compared.

A polypeptide includes an antibody or an enzyme. Polypeptides also include analogs and peptide mimetics such as amino acids joined by an ether as opposed to an amide bond. The constituent amino acids may be naturally occurring amino acids or structural analogs of natural amino acids that can function in a similar manner as naturally occurring amino acids. A peptide or protein analog comprises an unnatural or modified amino acid side-chain, a modified amide backbone, or modified terminus, e.g. carboxyl-terminus amide or cyclized polypeptide.

The terms "cleaving" or "cleavage" refer to breaking a covalent bond within a compound, e.g., a peptide or peptide-linker-dye substrate. The term "cleavage site" thus refers to a particular amide bond (e.g., peptide bond between amino acids in a peptide or bond between a terminus, such as the C-terminus, of a peptide and a linker) in a peptide is cleaved by a protease enzyme, e.g. a caspase. Cleavage results in two peptide subunits or a peptide subunit and a leaving group, e.g., a linker with a free end.

The term "label", as used herein, means any moiety which can be attached to a peptide and that functions to: (i) provide a detectable signal; (ii) interact with a second label to modify the detectable signal provided by the first or second label. (iii) stabilize hybridization, i.e. duplex formation; (iv) affect mobility, e.g. electrophoretic mobility or cell-permeability, by charge, hydrophobicity, shape, or other physical parameters, or (v) provide a capture moiety, e.g., affinity, antibody/antigen, or ionic complexation.

As used herein, colors and color channels such as near infrared, red, orange, yellow, green, cyan, blue, and violet have their ordinary and customary meaning in the arts of fluorescence detection in molecular and cell biology, including fluorescence microscopy and flow cytometry. Exemplary ranges for the colors and color channels are as follows: about 380 nm to about 435 or 440 nm for violet, about 435 or 440 nm to about 485 nm or about 435 or 440 nm to about 500 nm for blue, about 485 to 500 nm or about 500 nm to about 520 nm for cyan, about 500 nm or 520 nm to about 560 nm or about 500 nm or 520 nm to about 565 nm for green, about 560 or 565 nm to about 590 nm or about 560 or 565 nm to about 600 nm for yellow, about 590 nm or 600 nm to about 625 nm or about 590 nm or 600 nm to about 650 nm for orange, about 625 nm or 650 nm to about 700 nm or about 625 nm or 650 nm to about 740 nm for red, and about 700 nm or 740 nm to about 1000 nm or about 700 nm or 740 nm to about 2000 nm for near infrared.

As used herein, the term "kit" refers to a packaged set of related components, such as one or more compounds or compositions and one or more related materials such as solvents, solutions, buffers, instructions, desiccants, or cells.

"Substituted" as used herein refers to a molecule wherein one or more hydrogen atoms are replaced with one or more non-hydrogen atoms, functional groups or moieties. By example, an unsubstituted nitrogen is —NH$_2$, while a substituted nitrogen is —NHCH$_3$. Exemplary substituents include but are not limited to halogen, e.g., fluorine and chlorine, (C$_1$-C$_8$) alkyl, sulfate, sulfonate, sulfone, amino, ammonium, amido, nitrile, nitro, lower alkoxy, phenoxy, aromatic, phenyl, polycyclic aromatic, heterocycle, water-solubilizing group, linkage, and linking moiety.

"Array" means a predetermined spatial arrangement of peptides, cells, or other samples present on a solid support or in an arrangement of vessels, e.g. wells.

A dashed line projecting from a substituent, such as:

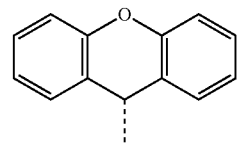

indicates the point of attachment to the base molecule. For a fused ring, dashed lines indicate portions of the base molecule where the fused ring is attached, such as:

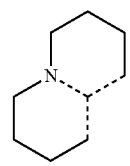

wherein the full molecule could have the structure:

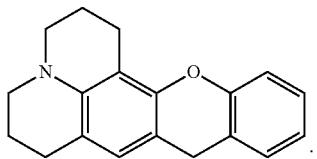 [SMILES: c1ccc2c(c1)Cc1cc3c4c(c1O2)CCCN4CCC3]

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined herein, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the definitions provided herein are not intended to include impermissible substitution patterns (e.g., methyl substituted with 5 fluoro groups). Such impermissible substitution patterns are well known to the skilled artisan.

The compounds disclosed herein may exist in unsolvated forms as well as solvated forms, including hydrated forms. These compounds may exist in multiple crystalline or amorphous forms. In general, all physical forms are equivalent for the uses described herein and are intended to be within the scope of the present disclosure. The compounds disclosed herein may possess asymmetric carbon atoms (i.e., chiral centers) or double bonds; the racemates, diastereomers, geometric isomers and individual isomers of the compounds described herein are within the scope of the present disclosure. The compounds described herein may be prepared as a single isomer or as a mixture of isomers.

Where substituent groups are specified by their conventional chemical formulae and are written from left to right, they equally encompass the chemically identical substituents, which would result from writing the structure from right to left, e.g., —CH$_2$O— is intended to also recite —OCH$_2$—.

It will be understood that the chemical structures that are used to define the compounds disclosed herein are each representations of one of the possible resonance structures by which each given structure can be represented. Further, it will be understood that by definition, resonance structures are merely a graphical representation used by those of skill in the art to represent electron delocalization, and that the present disclosure is not limited in any way by showing one particular resonance structure for any given structure.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

"Alkyl" refers to monovalent saturated aliphatic hydrocarbyl groups having from 1 to 10 carbon atoms and preferably 1 to 6 carbon atoms, e.g. 1, 2, 3, 4, 5 or 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxylalkyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cvcloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, sulfonyl, substituted sulfonyl, sulfonyloxy, thioacyl, thiol, alkylthio, and substituted alkylthio, wherein said substituents are defined herein. Particular substituted alkyl groups comprise a reactive group for direct or indirect linking to a carrier molecule or solid support, for example, but not limited to, alkyl substituted by carboxyl or a carboxyl ester (e.g. an activated ester such as an N-hydroxysuccinimide ester) and alkyl substituted by aminocarbonyl —CONHR where R is an organic moiety as defined below with reference to the term "aminocarbonyl", e.g. a C$_1$-C$_{10}$ (e.g. C$_1$-C$_6$) alkyl terminally substituted by a reactive group (R$_x$) including, but not limited to, carboxyl, carboxylester, maleimide, succinimidyl ester (SE), sulfodichlorophenyl (SDP) ester, sulfotetrafluorophenyl (STP) ester, tetrafluorophenyl (TFP) ester, pentafluorophenyl (PFP) ester, nitrilotriacetic acid (NTA), aminodextran, and cyclooctyne-amine.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl), wherein substituted alkyl is defined herein.

"Aryl" or "Ar" refers to a monovalent aromatic carboxylic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, sulfonyl, substituted sulfonyl, sulfonyloxy, thioacyl, thiol, alkylthio, and substituted alkylthio, wherein said substituents are defined herein.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, but-3-en-1-yl, and propenyl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino. (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocvclylthio, nitro, sulfo, sulfonyl, substituted sulfonyl, sulfonyloxy, thioacvl, thiol, alkylthio, and substituted alkylthio, wherein said substituents are defined herein and with the proviso that any hydroxy substitution is not attached to a vinyl (unsaturated) carbon atom.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O) substituted alkyl, —NRC(O)cycloalkyl, —NRC(O) substituted cycloalkyl, —NRC(O)cycloalkenyl, —NRC(O) substituted cycloalkenyl, —NRC(O) alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O)heterocyclic, and —NRC(O) substituted heterocyclic, wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O) O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl. —$SO_2$— substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl substituted alkenyl alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NRSO$_2$NR'R" where R is hydrogen or alkyl and R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR''')R'R" where R', R", and R''' are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryloxy" refers to the group —O-aryl, where aryl is as defined herein, that includes, by way of example, phenoxy and naphthoxy.

"Substituted aryloxy" refers to the group —O-(substituted aryl), where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino. (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, sulfonyl, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof.

"Carboxyl alkyl" or "carboxyalkyl" refers to the group —(CH$_2$)$_n$COOH, where n is 1-6.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, —NR—C(O)O-substituted alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl. —NR—C(O)O-cycloalkyl, —NR—C(O)O-substituted cycloalkyl. —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic, wherein R is alkyl or hydrogen, and wherein alkyl, substituted alkyl, alkenyl, substituted alkenyl, alkynyl. substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refer to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester. (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, sulfo, sulfonyl, substituted sulfonyl, sulfonyloxy, thioacvl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"H" indicates hydrogen.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5, or preferably 1 to 3 of the same substituents as defined for substituted cycloalkyl.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Heterocyclyloxy" refers to the group —O-heterocyclyl.

"Substituted heterocyclyloxy" refers to the group —O-(substituted heterocyclyl).

"Heterocyclylthio" refers to the group —S— heterocyclyl.

"Substituted heterocyclylthio" refers to the group —S-(substituted heterocyclyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Hydrazinyl" refers to the group —NHNH$_2$— or =NNH—.

"Substituted hydrazinyl" refers to a hydrazinyl group, wherein a non-hydrogen atom, such as an alkyl group, is appended to one or both of the hydrazinyl amine groups. An example of substituted hydrazinyl is —N(alkyl)-NH$_2$ or =N$^{30}$(alkyl)-NH$_2$.

"Nitro" refers to the group —NO$_2$.

"Oxo" refers to the atom (=O) or (—O$^-$).

"Spirocyclyl" refers to divalent saturated cyclic group from 3 to 10 carbon atoms having a cycloalkyl or heterocyclyl ring with a spiro union (the union formed by a single atom which is the only common member of the rings) as exemplified by the following structure:

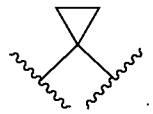

"Sulfo" refers to the groups —SO$_3$H or —SO$_3^-$.

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl. —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl), wherein substituted alkyl is as defined herein.

The term "carrier molecule" as used herein, refers to a biological or a non-biological component that is or becomes covalently bonded to a cell-tracker compound disclosed herein. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. Included is one embodiment in which carrier molecules comprise an organic moiety having at least 4 plural valent atoms and often more than 10 plural valent atoms (i.e., atoms other than hydrogen and halo), e.g. at least 15 such atoms, as in the case of moieties having at least 20 such atoms.

The term "conjugated substance" or "Se" refers to a carrier molecule or solid support.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

As used herein, the term "fluorophore" or "fluorogenic" refers to a compound or a composition that demonstrates a change in fluorescence upon binding to a biological compound or analyte of interest and/or upon cleavage by an enzyme. The fluorophores of the present disclosure may be substituted to alter the solubility, spectral properties or physical properties of the fluorophore.

As used herein, "a pharmaceutically acceptable salt" or "a biologically compatible salt" is a counterion that is not toxic as used, and does not have a substantially deleterious effect on biomolecules. Examples of such salts include, among others. K$^+$, Na$^+$, Cs$^+$, Li$^+$, Ca$^{2+}$, Mg$^{2+}$, Cl$^-$, AcO$^-$, and alkylammonium or alkoxyammonium salts.

The term "linker" or "L", as used herein, refers to a single covalent bond or a moiety comprising series of stable covalent bonds, the moiety often incorporating 1-40 plural valent atoms selected from the group consisting of C, N, O, S and P that covalently attach the fluorogenic or fluorescent compounds to another moiety such as a chemically reactive group or a biological and non-biological component. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups, or both. Examples of such pendant moieties are hydrophilicity modifiers, for example solubilizing groups like, e.g. sulfo. In certain embodiments, a linker is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety that includes —C(O)NH—, —C(O)O—, —NH—, —S—, —O—, and the like. Linkers may, by way of example, consist of a combination of moieties selected from alkyl; —C(O)NH—; —C(O)O—; —NH—; —S—; —O—; —C(O)—; —S(O)$_n$— where n is 0, 1 or 2; —O—; 5- or 6-membered monocyclic rings; and optional pendant functional groups, for example sulfo, hydroxy and carboxy. The moiety formed by a linker bonded to a reactive group (R$_x$) may be designated -L-R$_x$. The reactive group may be reacted with a substance reactive therewith, whereby the linker becomes bonded to a conjugated substance (S$_c$) and may be designated -L-S$_c$c, or in some cases, the linker may contain a residue of a reactive group (e.g. the carbonyl group of an ester) and may be designated "–L". A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present disclosure to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al., *Biochem. Biophys. Acta.* 761:152-162 (1983); Joshi et al., *J. Biol. Chem.*, 265:14518-14525 (1990); Zarling et al., *J. Immunol.*, 124:913-920 (1980); Bouizar et al., *Eur. J. Biochem.*, 155:141-147 (1986); Park et al., *J. Biol. Chem.*, 261:205-210 (1986); Browning et al., *J. Immunol.*, 143:1859-1867 (1989). Moreover a broad range of cleavable, bifunctional (both homo- and hetero-bifunctional) spacer arms are commercially available.

An exemplary cleavable group, such as an ester, is a cleavable group that may be cleaved by a reagent, e.g., sodium hydroxide, resulting in a carboxylate-containing fragment and a hydroxyl-containing product.

The linker may be used to attach the compound to another component of a conjugate, such as a targeting moiety (e.g., antibody, ligand, non-covalent protein-binding group, etc.), an analyte, a biomolecule, a drug and the like.

The term "reactive group" (or "$R_x$"), as used herein, refers to a group that is capable of reacting with another chemical group to form a covalent bond, i.e., is covalently reactive under suitable reaction conditions, and generally represents a point of attachment for another substance. The reactive group is a moiety, such as carboxylic acid or succinimidyl ester, on the compounds of the present disclosure that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides, succinimidyl esters (SE), sulfodichlorophenyl (SDP) esters, sulfotetrafluorophenyl (STP) esters, tetrafluorophenyl (TFP) esters, pentafluorophenyl (PFP) esters, nitrilotriacetic acids (NTA), aminodextrans, cyclooctyne-amines and the like. Methods to prepare each of these functional groups are well known in the art and their application to or modification for a particular purpose is within the ability of one of skill in the art (see, for example, Sandler and Karo, eds., Organic Functional Group Preparations. Academic Press, San Diego, 1989).

The term "solid support," as used herein, refers to a matrix or medium that is substantially insoluble in liquid phases and capable of binding a molecule or particle of interest. Solid supports suitable for use herein include semi-solid supports and are not limited to a specific type of support. Useful solid supports include solid and semi-solid matrixes, such as aerogels and hydrogels, resins, beads, biochips (including thin film coated biochips), microfluidic chip, a silicon chip, multi-well plates (also referred to as microtiter plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as SEPHAROSE (GE Healthcare), poly(acrylate), polystyrene, poly(acrylamide), polyol, agarose, agar, cellulose, dextran, starch, FICOLL (GE Healthcare), heparin, glycogen, amylopectin, mannan, inulin, nitrocellulose, diazocellulose, polyvinylchloride, polypropylene, polyethylene (including poly(cthylene glycol)), nylon, latex bead, magnetic bead, paramagnetic bead, superparamagnetic bead, starch and the like.

"Water-solubilizing group" means a substituent which increases the solubility of the compounds of the invention in aqueous solution. Exemplary water-solubilizing groups include but are not limited to quaternary amine, sulfate, sulfonate, carboxylate, phosphonate, phosphate, polyether, polyhydroxyl, and boronate.

A. EXEMPLARY COMPOUND/ENZYME SUBSTRATES

In some embodiments, a compound is provided. In some embodiments, the compound is

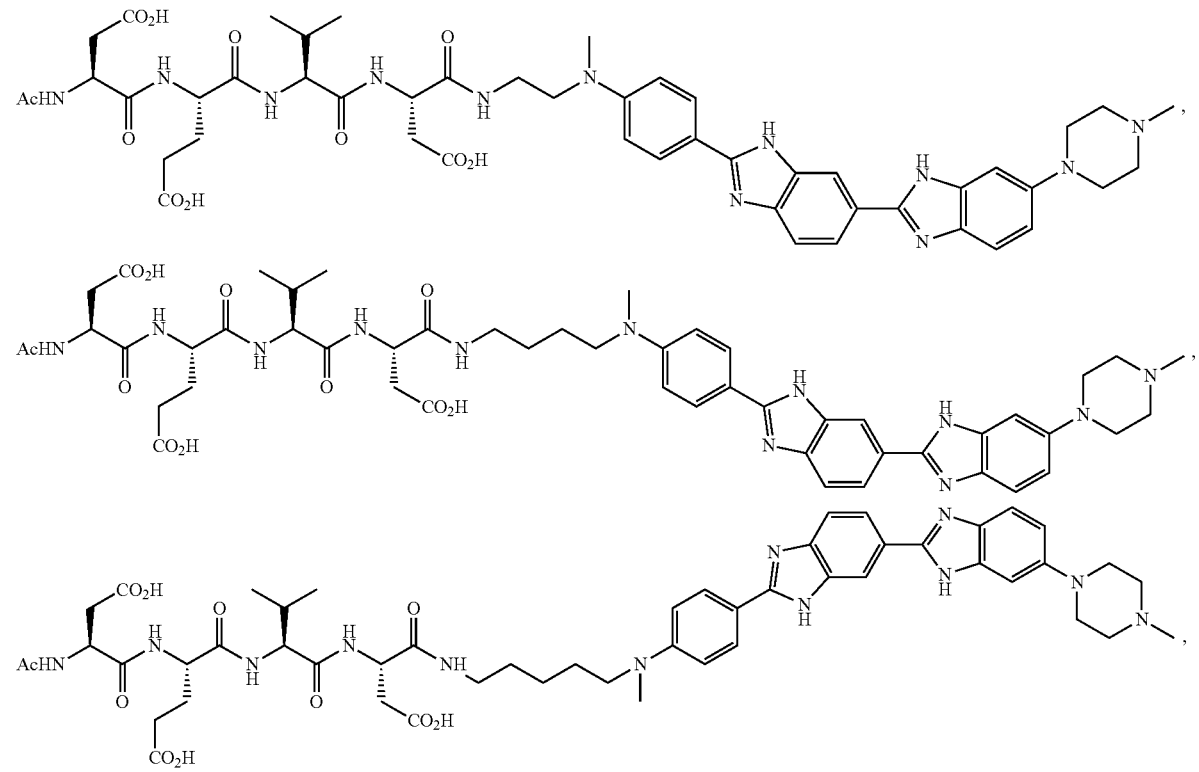

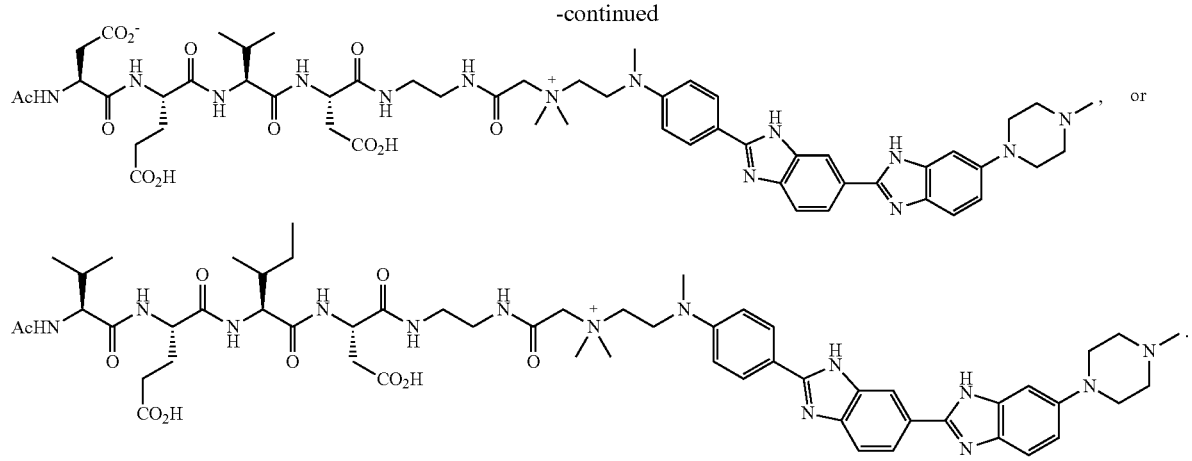
In some embodiments, the compound is
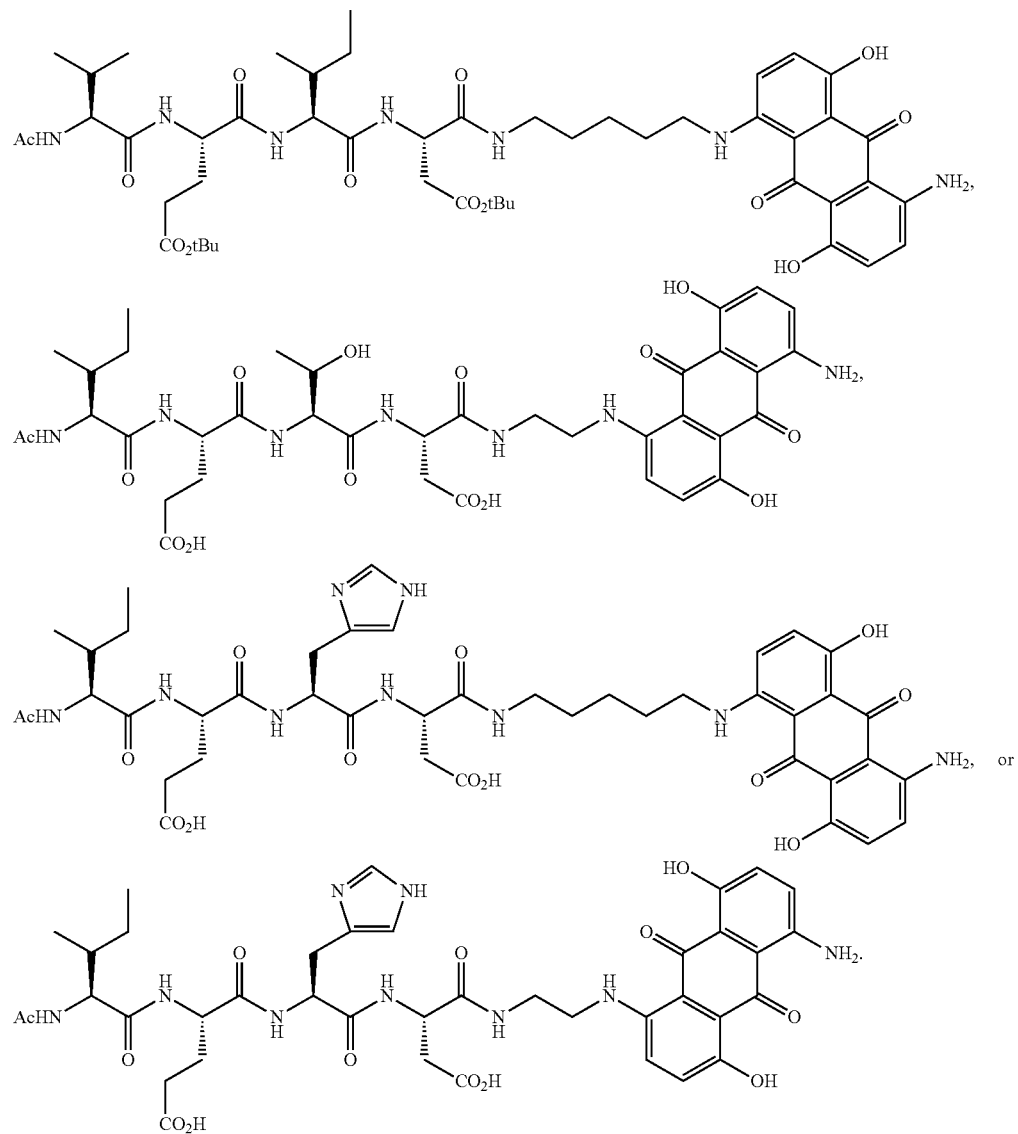

In some embodiments, the compound is a salt of any of the foregoing. In some embodiments, the compound is a pharmaceutically acceptable salt of any of the foregoing.

In one aspect, enzyme substrates are provided comprising a peptide covalently attached to a dye. The dye is attached to the peptide through a linker L. The dye may be attached through L to the amino terminus, the carboxyl terminus, or a side-chain of an amino acid of the peptide. The dye moiety can provide a detection element for localizing, visualizing, or quantitating cleavage events. The properties of the dyes can also facilitate transport through the cell membrane and targeting of intracellular structures and molecules. The enzyme substrates can retain the specific binding and recognition properties of the respective dyes and peptide sequence. In some embodiments, the dye is fluorescent when associated with a nucleic acid, such as DNA. In some embodiments, the dye is fluorescent in the violet channel. In some embodiments, the dye is fluorescent in the red channel.

In some embodiments, the fluorogenic probes comprise nucleic acid binding dyes attached either directly or indirectly to a peptide substrate moiety. In certain embodiments, the enzyme substrate moiety, when conjugated to the dye, reduces or eliminates the functionality of the dye. In certain embodiments, the substrate moiety may serve as a steric block such that, when attached to the dye, the substrate moiety interferes with the functionality of the dye. In another embodiment, the substrate moiety may carry a net positive or net negative charge so that upon conjugation to the dye, the substrate moiety alters the amount and/or nature of the charge on the dye that is associated with the functionality of the dye.

In some embodiments, the enzyme substrate for detecting or measuring caspase enzyme activity or apoptosis has an extra aspartic acid compared to a standard peptide substrate, e.g., a standard substrate for one or more of caspases 1, 8, or 9. The addition of the aspartic acid can increase the negative charge of the substrate moiety without interfering with substrate recognition and decreases the binding capacity of reagent to DNA while maintaining the binding capacity of the liberated dye after enzymatic cleavage. Further advantages of the extra aspartic acid include, lower background signal and increased impermeability to cross the nuclear membrane before cleavage resulting in localization of the reagent in the cytoplasm In some embodiments, the enzyme substrate is a compound of structural formula (I):

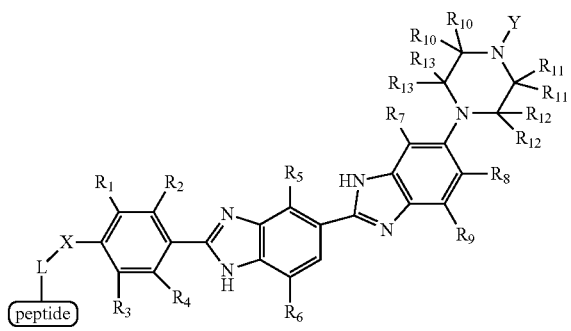

(I)

wherein Y is alkyl or substituted alkyl; X is —CH$_2$—, —O—, or —N(R)—, wherein R is H, halogen, alkyl or substituted alkyl; L is a linker; and each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, halogen, alkyl or substituted alkyl.

In some embodiments, each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, halogen, or alkyl. In some embodiments, each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H, alkyl, or substituted alkyl. In some embodiments, each $R_1$, $R_2$, $R_3$, $R_4$, $R_5$, $R_6$, $R_7$, $R_8$, $R_9$, $R_{10}$, $R_{11}$, $R_{12}$ and $R_{13}$ is independently H or alkyl. In some embodiments, each $R_1$, $R_2$, $R_3$, $R_4$, $R_5$, $R_6$, $R_7$, $R_8$, $R_9$, $R_{10}$, $R_{11}$, $R_{12}$ and $R_{13}$ is H. In some embodiments, at least one, two, three, four, five, six, seven, eight, nine, ten, eleven, or twelve of $R_1$, $R_2$, $R_3$, $R_4$, $R_5$, $R_6$, $R_7$, $R_8$, $R_9$, $R_{10}$, $R_{11}$, $R_{12}$ and $R_{13}$ are H.

In some embodiments, X is —N(R)— wherein R is H, halogen, alkyl, or substituted alkyl. In some embodiments. R is alkyl or substituted alkyl. In some embodiments, R is alkyl. In some embodiments. R is methyl, ethyl, propyl, or isopropyl. In some embodiments, R is methyl or ethyl. In some embodiments, X is —N(CH$_3$)—.

In some embodiments, Y is alkyl. In some embodiments, Y is methyl, ethyl, propyl, or isopropyl.

In some embodiments, Y is methyl or ethyl. In some embodiments, Y is methyl.

In some embodiments, the enzyme substrate is a compound of structural formula (II):

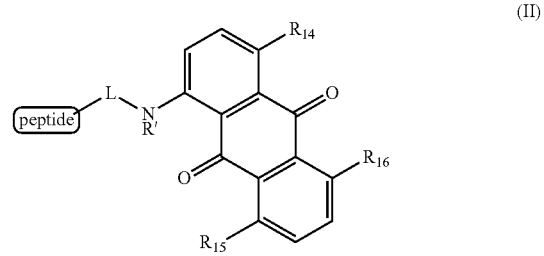

(II)

wherein $R_{14}$, $R_{15}$, and $R_{16}$ are each independently —OH or —NH$_2$; R' is H, alkyl or substituted alkyl; and L is a linker.

In some embodiments, $R_{14}$ is —OH. In some embodiments, $R_{15}$ is —OH. In some embodiments, $R_{16}$ is —NH$_2$. In some embodiments, $R_{14}$ is —OH and $R_{15}$ is —OH. In some embodiments, $R_{14}$ is —OH and $R_{16}$ is —NH$_2$. In some embodiments, $R_{15}$ is —OH and $R_{16}$ is —NH$_2$. In some embodiments, $R_{14}$ is —OH, $R_{15}$ is —OH, and $R_6$ is —NH$_2$.

In some embodiments, R' is H or alkyl. In some embodiments, R' is H or methyl, ethyl, propyl, or isopropyl. In some embodiments, R' is H.

In some embodiments, the enzyme substrate comprises a peptide and a fluorogenic dye and having structural formula (III):

peptide-L-dye    (III);

wherein:
the peptide comprises a sequence of DX$_2$EX$_1$D (SEQ ID NO. 8) or DX$_2$VX$_1$D (SEQ ID NO. 20), wherein X$_2$ is W, Y, I, L, or V. and X$_1$ is any amino acid; L is a linker; and dye is the fluorogenic dye, wherein the fluorogenic dye is able to emit a fluorescent signal upon excitation when free from the peptide. The fluorogenic dye is considered free from the peptide when the peptide has been cleaved, e.g., at an internal position of the peptide or at its C-terminus, such that the fluorogenic dye is no longer linked to the complete peptide as present in the enzyme substrate before cleavage. In some embodiments, the fluorogenic dye is able to associate with a nucleic acid when free from the peptide, and is able to emit a fluorescent signal upon excitation when associated with a nucleic acid. In some embodiments, the fluorogenic dye is as disclosed above with respect to structural formula (I) or structural formula (II). In some embodiments, the fluorogenic dye comprises a rhodamine moiety. In some embodiments, the rhodamine moiety is a rhodamine 110 (R110) moiety, such as N-Octyloxycarbonyl-R110 or N'-morpholinecarbonyl-R110. See, e.g., U.S. Pat. No. 7,270,801; Cai et al., *Bioorg. Med. Chem. Lett.* 11:39-42 (2001); Terentyeva et al., *Bioconj. Chem.* 22:1932-1938 (2011). In some embodiments, the enzyme substrate has the formula:

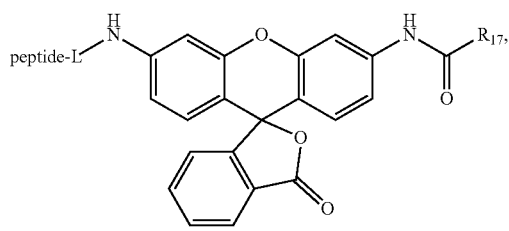

wherein $R_{17}$ is OH, —O—$C_{1-12}$ alkyl, a substituted —O—$C_{1-12}$ alkyl, $NH_2$, —NH—$C_{1-12}$ alkyl, a substituted —NH—$C_{1-12}$ alkyl, or a heterocycle, such as N-morpholino (which may be optionally substituted). In some embodiments, the fluorogenic dye has the formula:

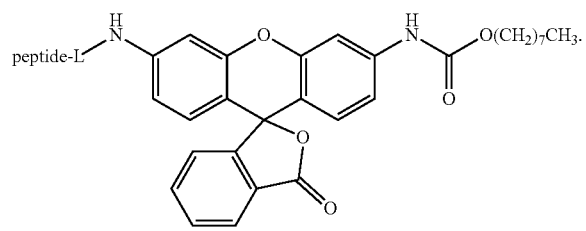

In some embodiments, the rhodamine moiety is a rhodamine 600 (R600) moiety, optionally comprising a silicon, germanium, or tin atom at the 10 position of the xanthene ring system in the rhodamine 600 moiety, such as an SiR600 or 2-Me SiR600 moiety. See. e.g., U.S. Pat. No. 9,329,184. In some embodiments, the fluorogenic dye is a thiazole, such as thiazole orange or 2-[(1-(5-((2-aminoethylamino)carbonyl)pentyl)quinolinium-4(1H)-ylidene)methyl]-3-methylbenzo[d]thiazolium iodide (NUCVIEW™488, Biotium, Inc., Hayward, Calif.). See. e.g., Cen et al., *FASEB J.* 22:2243-2252 (2008). In some embodiments, the fluorogenic dye is a coumarin, dibenzorhodamine, or cresyl violet. In some embodiments, the fluorogenic dye is a compound having structural formula (IV):

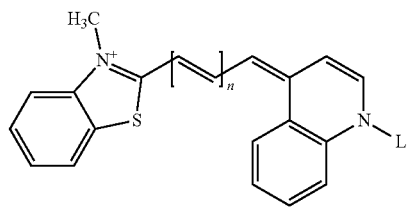

wherein:
n=0 or 1; and
L is a linker; and
the peptide is $DX_2EX_1D$ (SEQ ID NO. 8), wherein $X_2$ is W, Y, I, L, or V, and $X_1$ is any amino acid.

In some embodiments, the fluorogenic dye comprises a bis-benzamide moiety or an anthraquinone moiety.

The following descriptions of peptides, linkers, solid supports, tautomerism, isomerism, charge, protonation state, and counterions are provided with respect to the enzyme substrates disclosed herein in general, with respect to each of structural formulae (I), (II), and (III), and with respect to subgenera thereof, including species, where applicable.

Peptide sequences of enzyme substrates, such as the sequences of peptides in enzyme substrates of structural formula (I), (II) or (III), may have a protease-cleavage site, such as a caspase-cleavage site.

A protease binding site is an amino acid sequence (peptide) which is recognized and cleaved by a particular protease (Komoriya. U.S. Pat. No. 5,714,342). In some embodiments, compounds disclosed herein are enzyme substrates for the family of caspase enzymes. Caspases are known to cleave peptide substrates adjacent to particular amino acids within a recognition site. A particular caspase does not cleave every bond in a substrate that has any particular amino acid. Rather, caspases are specific to particular amino acid sequences which serve as recognition domains for each particular caspase.

Certain peptide sequences of enzyme substrates are substrates for caspase enzymes. Any peptide that comprises the DEVD (SEQ ID NO. 1) caspase recognition site can be part of an enzyme substrate of the invention. In this recognition site, the cleavage site is the amide bond between the aspartic acid residue D toward the carboxyl terminus and the adjacent amino acid. For example, the caspase recognition site in a peptide containing the sequence $(AA)_n$-DEVDG-$(AA)_m$ (SEQ ID NO.21) will cleave to form $(AA)_n$-DEVD (SEQ ID NO. 22) and G-$(AA)_m$ (SEQ ID NO. 23) peptide fragments, the former with a D carboxy-terminus and the latter with a G amino-terminus. As additional examples, the sequences Asp-Glu-Val-Asp-Gly (DEVDG) (SEQ ID NO. 3) and Gly-Asp-Glu-Val-Asp-Gly-Ile-Lys (GDEVDGIK) (SEQ ID NO. 4) are caspase-specific sequences which result in cleavage by caspase of an amide bond in the enzyme substrate. The DEVDG (SEQ ID NO. 3) sequence in the enzyme substrate represented below may be flanked by other amino acids where n may be 0 to 100:

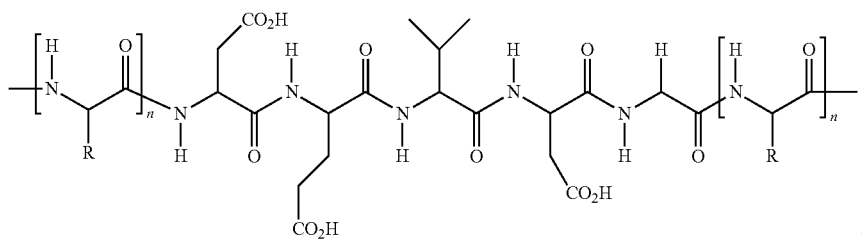

Caspases cleave sequences other than those containing DEVD (SEQ ID NO. 1) as well. In some embodiments, the peptide comprises an amino acid sequence of $X_2EX_1D$ (SEQ ID NO. 5), wherein $X_2$ is W, Y, I, L, D, or V, and $X_1$ is any amino acid. In some embodiments, the peptide comprises an amino acid sequence of $X_3DEX_1D$ (SEQ ID NO. 6), wherein $X_3$ is V or L and $X_1$ is any amino acid. In some embodiments, the peptide comprises an amino acid sequence of $DX_1VD$ (SEQ ID NO. 7), wherein $X_1$ is any amino acid. In some embodiments, the peptide comprises an amino acid sequence of $DX_2EX_1D$ (SEQ ID NO. 8), wherein $X_2$ is W, Y, I, L, or V, and $X_1$ is any amino acid. In some embodiments, the peptide comprises an amino acid sequence of $DX_2EX_1D$ (SEQ ID NO. 8), wherein $X_2$ is I, L, or V, and $X_1$ is any amino acid. In some embodiments, the peptide comprises an amino acid sequence of $DX_1EX_1D$ (SEQ ID NO. 8), wherein $X_2$ is W or Y, and $X_1$ is any amino acid. In some embodiments, the peptide comprises an amino acid sequence of $DX_2VX_1D$ (SEQ ID NO. 20), wherein $X_2$ is W, Y, I, L, or V, and $X_1$ is any amino acid. In some embodiments, the peptide comprises an amino acid sequence of $DX_2VX_1D$ (SEQ ID NO. 20), wherein $X_2$ is W or Y. and $X_1$ is any amino acid. In some embodiments, $X_1$ in any of the foregoing sequences is H, A, T, I, or V. In some embodiments, the peptide comprises an amino acid sequence of WEHD (SEQ ID NO. 9), YVAD (SEQ ID NO. 10), YVHD (SEQ ID NO. 11), VDVAD (SEQ ID NO. 12), LEHD (SEQ ID NO. 2), IETD (SEQ ID NO. 13), VEID (SEQ ID NO. 14), DEVD (SEQ ID NO. 1), LEVD (SEQ ID NO. 15), or AEVD (SEQ ID NO. 16). In some embodiments, the peptide comprises an amino acid sequence of DIETD (SEQ ID NO. 17), DLEHD (SEQ ID NO. 18), or DYVAD (SEQ ID NO. 19).

In some embodiments, the fluorogenic probes comprise nucleic acid binding dyes attached either directly or indirectly to a peptide substrate moiety. In certain embodiments, the enzyme substrate moiety, when conjugated to the dye, reduces or eliminates the functionality of the dye. In certain embodiments, the substrate moiety may serve as a steric block such that, when attached to the dye, the substrate moiety interferes with the functionality of the dye. In another embodiment, the substrate moiety may carry a net positive or net negative charge so that upon conjugation to the dye, the substrate moiety alters the amount and/or nature of the charge on the dye that is associated with the functionality of the dye.

In some embodiments, the enzyme substrates provided herein have an extra aspartic acid compared to a standard peptide substrate, e.g., a standard substrate for one or more of caspases 1, 8, or 9. The addition of the aspartic acid can increase the negative charge of the substrate moiety without interfering with substrate recognition and decreases the binding capacity of reagent to DNA while maintaining the binding capacity of the liberated dye after enzymatic cleavage. Further advantages of the extra aspartic acid include, lower background signal and increased impermeability to cross the nuclear membrane before cleavage resulting in localization of the reagent in the cytoplasm.

In some embodiments, the peptide is a substrate for cleavage by at least one caspase, has a length of 5 or more amino acids, and comprises an aspartic acid in the $P_5$ position, i.e., the $5^{th}$ amino acid N-terminal to the scissile peptide bond of the caspase substrate. Because caspases generally cleave immediately C-terminally to an aspartic acid residue, such sequences will fit the general pattern DXXXD (SEQ ID NO. 24) (e.g., the sequences $DX_2EX_1D$ (SEQ ID NO. 8), $DX_2VX_1D$ (SEQ ID NO. 20), DIETD (SEQ ID NO. 17), DLEHD (SEQ ID NO. 18), and DYVAD (SEQ ID NO. 19) discussed above). It has been found that, especially where the $P_4$ residue is not acidic, including the D at $P_5$ can add an additional negative charge with potential benefits such as decreasing the uncleaved substrate's binding capacity for nucleic acid, e.g., DNA, lowering background signal, and increasing localization of the uncleaved substrate in the cytoplasm relative to the nucleus. Furthermore, one or more of these benefits can be provided without interfering with substrate recognition, without affecting nucleic acid (e.g., DNA) binding capacity after cleavage, or both.

In some embodiments, any of the foregoing peptide sequences is flanked C-terminally, N-terminally, or both C-terminally and N-terminally by one or more additional amino acid residues, e.g., 1 to 100 amino acid residues. In some embodiments, any of the foregoing peptide sequences is flanked C-terminally by 1 to 50, 1 to 20, 1 to 10, 1 to 5, 5, 4, 3, 2, or 1 amino acid residues. In some embodiments, any of the foregoing peptide sequences is flanked N-terminally by 1 to 50, 1 to 20, 1 to 10, 1 to 5, 5, 4, 3, 2, or 1 amino acid residues. In some embodiments, the peptide has a sequence with a total length of 4 to 200 amino acid residues, 4 to 100 amino acid residues, 4 to 50 amino acid residues, 5 to 200 amino acid residues, 5 to 100 amino acid residues, 5 to 50 amino acid residues, 20 to 50 amino acid residues, or 4, 5, 6, 7, 8, 9, 10, 11, 12, 13, 14, 15, 16, 17, 18, 19, or 20 amino acid residues.

In some embodiments, any of the foregoing sequences is the entire amino acid sequence of the peptide, i.e., the peptide has no additional amino acid residues (but optionally has one or more modifications such as one or more protecting groups, N-acylations, amidated carboxyls, or the like; or a linker attached N-terminally. C-terminally, or to a side chain). In some embodiments, any of the foregoing is the C-terminal amino acid sequence of the peptide, i.e., the peptide has no additional residues following the C-terminal Asp residue of a sequence listed above (but optionally has one or more additional N-terminal residues; one or more modifications such as one or more protecting groups, N-acylations, amidated carboxyls, or the like; or a linker attached N-terminally, C-terminally, or to a side chain).

The side-chains of certain amino acids of the peptide may be protected. For example, acidic or basic side chains may be protected. In some embodiments, acidic side chains are protected as esters, such as t-butyl esters.

In some embodiments, the peptide comprises an N-terminal acyl. e.g., an acetyl or carboxybenzyl.

The enzyme substrate may be covalently attached to a solid support. The solid support may be any material useful as a synthesis support or to which a peptide may be covalently attached. The solid support may be a bead, a particle, or a monolithic material with a surface or pores to which a peptide may be covalently attached.

The dye moiety may be covalently attached to the peptide through a linker. Rigid and non-rigid linkages may be useful. Generally, the linkage linking the label and the peptide should not (i) inhibit membrane permeability, (ii) inhibit enzymatic activity, or (iii) adversely affect the properties of the label, e.g. quenching or bleaching fluorescence of a dye. Peptides can be labeled at sites including an amino acid side-chain, the amino terminus, and the carboxy terminus. Peptides can be functionalized to bear reactive amino, thiol, sulfide, disulfide, hydroxyl, and carboxyl groups at any of these sites. L may be any bond, such as an amide or phosphate, or comprise a chain, such as an alkyldiyl, phenyldiyl, or benzydiyl, and substituted forms thereof.

In some embodiments, L is —N($R_{N1}$)—[$CH_2$]$_n$—, wherein n ranges from 1 to 10 and $R_{N1}$ is H or optionally substituted $C_{1-6}$ alkyl. In some embodiments, L is —N($R_{N1}$)-$L_a$-, wherein $L_a$ is a $C_{2-10}$ alkylene optionally interrupted by one or both of —N($R_{N1}$)—C(O)— or —N$^+$($R_{N2}$)$_2$—, wherein each $R_{N1}$ is independently H or optionally substituted $C_{1-6}$ alkyl and each $R_{N2}$ is independently an optionally substituted $C_{1-6}$ alkyl. In some embodiments. L is —C(O)—[$CH_2$]$_n$-n wherein n ranges from 1 to 10. In some embodiments, L is —N($R_{N1}$)—[$CH_2$]$_n$—C(O)—, wherein n ranges from 1 to 10 and $R_{N1}$ is H or optionally substituted $C_{1-6}$ alkyl. In some embodiments, L is —C(O)—[$CH_2$]$_n$—C(O)—, wherein n ranges from 1 to 10. In some embodiments, L is —[$CH_2$]$_n$—N$^+$($R_{N2}$)$_2$—[$CH_2$]$_n$—, wherein each $R_{N2}$ is independently an optionally substituted $C_{1-6}$ alkyl. In any of the foregoing, n can be 1, 2, 3, 4, 5, 6, 7, 8, 9, or 10. In any of the foregoing, the optionally substituted $C_{1-6}$ alkyl can be a methyl, ethyl, $C_3$ alkyl, $C_4$ alkyl, $C_5$ alkyl, or $C_6$ alkyl, any of which can be optionally substituted. In some embodiments, each $R_{N2}$ is methyl. In some embodiments, each $R_{N1}$ is methyl. In some embodiments, each $R_{N1}$ is H.

In some embodiments, L is —NH—[$CH_2$]$_2$—. In some embodiments, L is —NH—[$CH_2$]$_4$—. In some embodiments, L is —NH—[$CH_2$]$_5$—. In some embodiments, L is —NH—[$CH_2$]$_2$—NH—C(O)—$CH_2$—N($CH_3$)$_2$—[$CH_2$]$_2$—.

Those of skill in the art will appreciate that many of the enzyme substrates, including the dye moieties may exhibit the phenomena of tautomerism, conformational isomerism, geometric isomerism and/or stereo isomerism. As the formulae drawings within this specification and claims cannot necessarily represent all of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein.

In addition, it will also be apparent that the enzyme substrates of the present disclosure may exist in many different protonation states, depending on, among other things, the pH of their environment. While the structural formulae provided herein depict the compounds in only one of several possible protonation states, it will be understood that these structures are illustrative only, and that the invention is not limited to any particular protonation state. Any and all protonated forms of the enzyme substrates are intended to fall within the scope of the invention.

Furthermore, the enzyme substrates of the present disclosure may bear multiple positive or negative charges. The associated counter ions with the enzyme substrates are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion.

B. METHODS, USES, AND COMPOSITIONS FOR DETECTION AND MEASUREMENT

Certain embodiments provide a method, use, or composition for detecting the presence or absence of a caspase enzyme in a cell or mixture of cells, being compatible for use with, for example, flow cytometry and fluorescence microscopy, and including incubating the cell or mixture of cells with a compound or enzyme substrate disclosed herein; providing a stimulus to the cell or mixture of cells to elicit a fluorescent signal; and measuring the fluorescent signal, whereby the presence or absence of the caspase enzyme is detected.

Certain embodiments provide a method, use, or composition for measuring the activity of a caspase enzyme in a cell or mixture of cells, being compatible for use with, for example, flow cytometry and fluorescence microscopy, and including incubating the cell or mixture of cells with a compound or enzyme substrate disclosed herein; providing a stimulus to the cell or mixture of cells to elicit a fluorescent signal; and measuring the fluorescent signal, whereby the activity of the caspase enzyme is measured.

Certain embodiments provide a method, use, or composition for detecting the presence or absence of apoptosis in a cell or mixture of cells, being compatible for use with, for example, flow cytometry and fluorescence microscopy, and including incubating the cell or mixture of cells with a compound or enzyme substrate disclosed herein; providing a stimulus to the cell or mixture of cells to elicit a fluorescent signal; and measuring the fluorescent signal, whereby the presence or absence of apoptosis is detected.

In some embodiments, the compound or enzyme substrate is delivered or passes into eukaryotic cells. When the cells are illuminated with a light source, then fluorescence emissions can be collected, detected, analyzed, or measured. Fluorescence emissions or intensity can be measured before and after the enzyme substrate enters the cells. The enzyme substrate may be cleaved inside the cell, e.g. by a protease enzyme. The particular protease enzyme may be termed a caspase enzyme and specific for cleaving certain peptide sequences. In some embodiments, the enzyme is caspase-1, caspase-3, caspase-6, caspase-7, caspase-8, caspase-9, or a combination thereof. The cells in the assay may also be treated with one or more caspase inhibitors, e.g., one or more inhibitors that inhibit caspase-1, caspase-3, caspase-6, caspase-7, caspase-8, or caspase-9, or a combination thereof. For discussions of caspases, their substrate preferences, and inhibitors, see Li and Yuan, *Oncogene* 27:6194-6206 (2008) and Poreba et al., *Cold Spring Harb Perspect Biol.* 5:a008680 (2013). The enzyme substrate may be cleaved inside the cell into two or more peptide fragments or into a peptide fragment and a linker-fluorophore fragment. The fluorescence emissions from the dye may be used to locate the presence of the dye inside the cell, as well as count cells. The cells in the assay may be treated with a substance or reagent that induces apoptosis, e.g., staurosporine. Data may be acquired using any appropriate fluorescence detection apparatus such as a plate reader, fluorescence microscope, or flow cytometer.

In some embodiments, the cell or mixture of cells are incubated with at least one, two, three, or four additional fluorescent molecules, wherein the at least one, two, three, or four additional fluorescent molecules are spectrally distinguishable from the compound of structural formula (I), and fluorescent signals are measured measuring from the at least one, two, three, or four additional fluorescent molecules. In some embodiments, the cell or mixture of cells are incubated with at least one, two, three, or four additional fluorescent molecules, wherein the at least one, two, three, or four additional fluorescent molecules are spectrally distinguishable from the compound of structural formula (II), and fluorescent signals are measured measuring from the at least one, two, three, or four additional fluorescent molecules. Fluorescence from two sources is considered spectrally distinguishable if the emission maxima are separated by at least about 30 nm or if fluorescence from the sources can be distinguished through the use of optical filters, e.g., a pair of filters wherein fluorescence from at least one of the molecules is differentially reduced by at least one of the filters. In some embodiments, the cell or mixture of cells is incubated with a compound of structural formula (I) and the at least one, two, three, or four additional fluorescent molecules have near infrared, red, orange, yellow, green, or cyan emission maxima. In some embodiments, the cell or mixture of cells is incubated with a compound of structural formula (II) and the at least one, two, three, or four additional fluorescent molecules have near infrared, yellow, green, cyan, blue, or violet emission maxima.

Many fluorescent proteins are known, e.g., RFP, BFP, CFP, YFP, mCherry, mOrange, EGFP, GFP, as are fusions thereof. In some embodiments, the cell or mixture of cells expresses or comprises a construct encoding at least one, two, three, or four fluorescent proteins, optionally wherein at least one, two, three, or four of the fluorescent proteins are fusion proteins, and the at least one, two, three, or four fluorescent proteins are spectrally distinguishable from the compound of structural formula (I). In some embodiments, the cell or mixture of cells expresses or comprises a construct encoding at least one, two, three, or four fluorescent proteins, optionally wherein at least one, two, three, or four of the fluorescent proteins are fusion proteins, and the at least one, two, three, or four fluorescent proteins are spectrally distinguishable from the compound of structural formula (II). In some embodiments, the cell or mixture of cells expresses or comprises a construct encoding at least one, two, three, or four fluorescent proteins, optionally wherein at least one, two, three, or four of the fluorescent proteins are fusion proteins, and the at least one, two, three, or four fluorescent proteins are spectrally distinguishable from at least one of the compound of structural formula (I) or the compound of structural formula (II). In some embodiments, the cell or mixture of cells is incubated with a compound of structural formula (I) and the at least one, two, three, or four additional fluorescent molecules have near infrared, red, orange, yellow, green, or cyan emission maxima. In some embodiments, the cell or mixture of cells is incubated with a compound of structural formula (II) and the at least one, two, three, or four additional fluorescent molecules have near infrared, yellow, green, cyan, blue, or violet emission maxima.

In another embodiment, the assay method may be conducted where cells are contained in a plurality of vessels. In any vessel, the cells may be of one type or different types of cells. The cells may be the same type grown under different conditions, e.g. in the presence of different media. Some of the cells may be treated with an apoptosis inducer or a caspase inhibitor. The plurality of vessels, an array, may be illuminated by a light source, e.g. a scanning light source. The cells may be of the same or different organisms.

In another aspect, the invention includes a solid phase method for detecting caspase activity. An enzyme substrate disclosed herein covalently attached by a linkage to a solid support is suspended in an aqueous solution containing a caspase in a vessel. The vessel is illuminated with a light source. Fluorescence in the vessel is detected to establish a caspase cleavage site in the peptide sequence in the enzyme substrate. The enzyme substrate may be cleaved into a peptide fragment that remains attached to the solid support and one or more soluble peptide fragments that are dissolved in the solution. Fluorescence from dyes linked to the peptide fragments may be detected.

C. KITS

In another aspect, kits are provided comprising a compound or enzyme substrate disclosed herein and one or more other reagents, such as an apoptosis inducer, a caspase inhibitor, cells, a solvent, or a desiccant. Kits may include reagents useful to conduct the assay methods of the invention. In some embodiments, kits comprise at least one of an organic solvent and a desiccant. In some embodiments, the solvent is DMSO. The kit may also include eukaryotic cells. In some embodiments, the kit is compatible for use with flow cytometry. In some embodiments, the kit is compatible for use with fluorescence microscopy.

In certain embodiments, the kits further comprise one or more of the following: a buffering agent, a purification medium, or a vial comprising the sample.

In certain embodiments, the kits disclosed herein comprise one or more of the compounds or enzyme substrates described herein, one or more carriers suitable for in vitro or in vivo applications, and one or more containers in which to store the one or more compounds and/or one or more carriers, such as solvents, buffers, stabilizers, pH adjusting agents, etc. The kit optionally contains instructions for how to prepare the one or more compounds or how to prepare a composition containing the one or more compounds, and how to administer the compound or composition containing the compound. In certain embodiments, the kit comprises instructions for performing a method disclosed herein, such as a method for detecting the presence or absence of a caspase enzyme in a cell or mixture of cells, a method for measuring caspase enzyme activity in a cell or mixture of cells, or a method for detecting the presence or absence of apoptosis. In certain embodiments, the method is an in vitro method. In certain embodiments, the method is an in vivo method. The kit may further comprise one or more pieces of equipment to administer the compound, or composition containing the compound including, but not limited to, syringes, pipettes, pipette bulbs, spatulas, vials, syringe needles, and various combinations thereof.

In certain embodiments, the kits provided herein comprise indicator solutions or indicator "dipsticks", blotters, culture media, cuvettes, and the like. In certain embodiments, the kits provided herein comprise indicator cartridges (where a kit component is bound to a solid support) for use in an automated detector. In certain embodiments, the kits provided herein further comprise molecular weight markers, wherein said markers are selected from phosphorylated and non-phosphorylated peptides, calcium-binding and non-calcium binding peptides, sulfonated and non-sulfonated peptides, and sialylated and non-sialylated peptides. In certain embodiments, the kits provided herein further comprise a member selected from a fixing solution, a detection reagent, a standard, a wash solution, and combinations thereof.

In certain embodiments, kits are provided, comprising:
(a) one or more of the compounds, enzyme substrates, or compositions described herein;
(b) one or more containers; and optionally
(c) instructions for detecting the presence or absence of a caspase enzyme in a cell or mixture of cells, measuring caspase enzyme activity in a cell or mixture of cells, or detecting the presence or absence of apoptosis according to a method disclosed herein.

D. INTERMEDIATES, SYNTHESIS, REACTIVE GROUPS, AND CARRIER MOLECULES

Attaching the dye to the peptide through a linker (labeling) can be accomplished using any one of a large number of known techniques, methods, standard reagents and reaction conditions. Exemplary methods in which a dye is conjugated to the C-terminus of a peptide are provided in Examples A and E below. Those skilled in the art can adapt these methods for use with various dyes and peptides.

A general protocol for conjugating dyes in the form of an NHS ester to peptides with an N-terminus amino group or a nucleophilic amino acid side-chain, e.g. cysteine or lysine, entails dissolving the NHS esters in aqueous acetonitrile (the percentage of acetonitrile is determined by the hydrophobicity of the dye to attain solubility) with peptides in water (or aqueous acetonitrile solution if peptides were hydrophobic). Aqueous sodium bicarbonate buffer (1 M) is added to the solution to achieve 0.1M buffer concentration while vortexing or shaking. The mixture is shaken at room temperature for 10 minutes to 30 minutes. The crude peptide-dye conjugate in the reaction mixture can be directly purified by reverse-phase HPLC.

In one method for labeling peptides, a nucleophilic functionality, e.g. a primary aliphatic amine, is introduced at a labeling attachment site on a peptide, e.g. an amino terminus. After automated, solid-support synthesis is complete, the peptide is cleaved from the support and all protecting groups are removed. The nucleophile-peptide is reacted with an excess of a label reagent containing an electrophilic linking moiety, e.g. isothiocyanate or activated ester, e.g. N-hydroxysuccinimide (NHS), under homogeneous solution conditions (Hermanson, *Bioconjugate Techniques,* (1996) Academic Press, San Diego. Calif. pp. 40-55, 643-71).

As an example, the terminal amine of lysine can be protected with a Dde group (N-(1-(4,4-dimethyl-2,6-dioxo-cyclohexylidene)ethyl)) while the N-terminal backbone amine is protected with Fmoc (fluorenylmethoxycarbonyl). After synthesis of the peptide is complete, the Dde is selectively removed with hydrazine while the Fmoc group stays intact. One or more lysine amino groups are thus available for labeling with a first electrophilic dye reagent such as an NHS ester. The peptide may be further manipulated, e.g. cleaved, deprotected, or purified. The N-terminal Fmoc group may then be removed and the resulting N-terminal amino group reacted with a second and different dye reagent. Other protecting groups, other sites on the peptide, and other sequences of steps are available to one skilled in the art of labeling peptides to specifically prepare enzyme substrates labeled at designed sites with the dyes provided herein.

In some cases, the dyes and the peptide may be coupled by in situ activation of the dye and reaction with the peptide to label the peptide in one step. For example, the carboxyl group of a dye may be activated and coupled with an N-terminus or side-chain amino group of a peptide to give a labeled peptide in one vessel. Alternatively, the terminal carboxyl or side-chain carboxyl of a peptide may be activated and coupled with an amino group a donor or acceptor dye to give a labeled peptide. A useful activator and coupling reagent is BOP (Benzotriazol-1-yloxy-tris(dimethyl-amino) phosphonium hexafluorophosphate). As an example, about 1 mg of a crude protected peptide with a free carboxyl terminus is dissolved in dimethylformamide (DMF) or acetonitrile and mixed with a molar excess of BOP and a donor or acceptor dye with an amino group, e.g. as a TFA salt. The mixture is shaken, stirred or let stand at room temperature for a few hours or a few days to couple the carboxyl terminus of the peptide to amino group of the dye to form an amide bond to make a dye labeled enzyme substrate. The solvent is completely removed, and the residue is deprotected with 30% TFA in methylene chloride for about 30 minutes. After evaporation, the mixture is purified by reverse-phased HPLC to give the dye labeled enzyme substrate.

In another method, a label is directly incorporated into the peptide during or prior to automated synthesis, for example as a solid support reagent (U.S. Pat. Nos. 5,736,626 and 5,141,813) or as a modified amino acid.

Reactive Groups.

In certain embodiments, the compounds provided herein are chemically reactive, and are substituted by at least one reactive group ($R_x$). The reactive group functions as the site of attachment for another moiety, such as a carrier molecule or a solid support, wherein the reactive group chemically reacts with an appropriate reactive or functional group on the carrier molecule or solid support. Thus, in certain embodiments, the compounds provided herein comprise a fluorophore, a linker, a reactive group moiety and optionally a carrier molecule and/or a solid support.

In certain embodiments, the compounds provided herein further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocvanate, an isothiocyanate, a maleimide, a phosphoramidite, a photoactivatable group, a reactive platinum complex, a silyl halide, a sulfonyl halide, and a thiol. In certain embodiments the reactive group is selected from the group consisting of carboxylic acid, succinimidyl ester of a carboxylic acid, hydrazide, amine and a maleimide. The reactive group may be attached to any appropriate site on the reporter molecule or the fluorophore. Alternatively, if the compounds disclosed herein comprise a carrier molecule or solid support a reactive group may be covalently attached independently to those substituents, allowing for further conjugation to a fluorophore, carrier molecule or solid support.

These reactive groups are synthesized during the formation of the compounds provided herein and carrier molecule-and/or solid support-containing compounds to provide chemically reactive compounds. In this way, compounds incorporating a reactive group may be covalently attached to a wide variety of carrier molecules or solid supports that contain, or are modified to contain, functional groups with suitable reactivity, resulting in chemical attachment of the components. In certain embodiments, the reactive group of the compounds disclosed herein and the functional group of the carrier molecule or solid support comprise electrophiles and nucleophiles that can generate a covalent linkage between them. In certain embodiments, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the compounds disclosed herein to the carrier molecule or solid support. Selected examples of functional groups and linkages are shown in Table 2, where the reaction of an electrophilic group and a nucleophilic group yields a covalent linkage.

TABLE 2

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a suitable leaving group (e.g., succinimidyloxy (—OC$_4$H$_4$O$_2$), sulfosuccinimidyloxy (—OC$_4$H$_3$O$_2$—SO$_3$H), -1-oxybenzotriazolyl (—OC$_4$—H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^x$ or —OCNR'NHR', where R$^x$ and R', which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates.

The choice of the reactive group used to attach the compounds disclosed herein to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In certain embodiments, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. As used herein, "reactive platinum complex" refers to chemically reactive platinum complexes such as described in U.S. Pat. No. 5,714,327, herein incorporated by reference in its entirety.

In certain embodiments, the disclosed herein comprise at least one reactive group that selectively reacts with an amine group. This amine-reactive group is selected from the group consisting of succinimidyl ester (SE), sulfonyl halide, tetrafluorophenyl (TFP) ester, sulfodichlorophenyl (SDP) ester, sulfotetrafluorophenyl (STP) ester, pentafluorophenyl (PFP) ester, nitrilotriacetic acid (NTA), aminodextran, cyclooctyne-amine and iosothiocyanates. Thus, in certain embodiments, the compounds provided herein form a covalent bond with an amine containing molecule in a sample. In certain embodiments, the compounds provided herein comprise at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904, all of which are herein incorporated by reference in their entirety).

Where the reactive group is an activated ester of a carboxylic acid, such as a succinimidyl ester (SE) of a carboxylic acid, a sulfonyl halide, tetrafluorophenyl (TFP) ester, sulfodichlorophenyl (SDP) ester, sulfotetrafluorophenyl (STP) ester, or pentafluorophenyl (PFP) ester, the resulting cell-tracker compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a certain embodiments, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In certain embodiments, the reactive group is a succinimidyl ester of a carboxylic acid, a sulfonyl halide, a tetrafluorophenyl ester, an iosothiocyanates or a maleimide. In certain embodiments, the reactive group is selected from sulfodichlorophenyl (SDP) ester, sulfotetrafluorophenyl (STP) ester, tetrafluorophenyl (TFP) ester, and a pentafluorophenyl (PFP) ester.

Carrier Molecules.

In certain embodiments, the compounds provided herein are covalently bound to a carrier molecule. If the compound has a reactive group, then the carrier molecule can alternatively be linked to the compound through the reactive group. The reactive group can contain both a reactive functional moiety and a linker, or only the reactive functional moiety.

A variety of carrier molecules are useful herein. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, polymers and bacterial particles.

In certain embodiments, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In certain embodiments, the carrier molecule is selected from a hapten, a nucleotide, an oligonucleotide, a nucleic acid polymer, a protein, a peptide or a polysaccharide. In certain embodiments the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In certain embodiments, the carrier molecule is an antibody or fragment thereof, an antigen, an avidin or streptavidin, a biotin, a dextran, an IgG binding protein, a fluorescent protein, agarose, and a non-biological microparticle. In certain embodiments, carrier molecules may comprise a label or a fluorescent dye or quencher.

In certain embodiments, the carrier molecule is an amino acid (including those that are protected or are substituted by phosphates, carbohydrates, or $C_1$ to $C_{22}$ carboxylic acids), or a polymer of amino acids such as a peptide or protein. In certain embodiments, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, a growth factor, bacterial particle or a binding partner for a cell receptor.

In certain embodiments, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In certain embodiments, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In certain embodiments, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In certain embodiments, the polysaccharide carrier molecule includes dextran, agarose or FICOLL.

In certain embodiments, the carrier molecule comprises a lipid (typically having 6-25 carbons), including glycolipids, phospholipids, and sphingolipids. In certain embodiments, the carrier molecule comprises a lipid vesicle, such as a liposome, or is a lipoprotein. Some lipophilic substituents are useful for facilitating transport of the conjugated dye into cells or cellular organelles.

In certain embodiments, the carrier molecule is a cell, cellular system, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In certain embodiments, the carrier molecule non-covalently associates with organic or inorganic materials. Exemplary embodiments of the carrier molecule that possess a lipophilic substituent may be used to target lipid assemblies such as biological membranes or liposomes by non-covalent incorporation of the compound within the membrane, e.g., for use as probes for membrane structure or for incorporation in liposomes, lipoproteins, films, plastics, lipophilic microspheres or similar materials.

In certain embodiments, the carrier molecule comprises a specific binding pair member wherein the compounds provided herein are conjugated to a specific binding pair member and used to the formation of the bound pair. Alternatively, the presence of the labeled specific binding pair member indicates the location of the complementary member of that specific binding pair, each specific binding pair member having an area on the surface or in a cavity which specifically binds to, and is complementary with, a particular spatial and polar organization of the other. In this instance, the compounds disclosed herein function as a reporter molecule for the specific binding pair. Exemplary binding pairs are set forth in Table 3.

TABLE 3

Representative Specific Binding Pairs

| Antigen | Antibody |
|---|---|
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |

TABLE 3-continued

Representative Specific Binding Pairs

| Antigen | Antibody |
|---|---|
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†DNA and cRNA are the complementary strands used for hybridization In another aspect, the invention includes a method of synthesizing an enzyme substrate by synthesizing a peptide, e.g., on a solid support, and reacting it with a dye labeling reagent. The peptide may have any of the peptide sequences disclosed herein. The dye labeling reagent can be a precursor of any of the compounds or enzyme substrates disclosed herein, in which in place of the peptide moiety and optionally part or all of the linker there is a reactive group for forming a bond to the peptide and, if applicable, forming the complete linker structure. In some embodiments, the dye labeling reagent is a precursor of an enzyme substrate of structural formula (I). In some embodiments, the dye labeling reagent is a precursor of an enzyme substrate of structural formula (II). Each labeling reagent has a linker moiety or reactive group for forming the linker moiety.

E. SOLID SUPPORTS

In certain embodiments, the compounds disclosed herein are covalently bonded to a solid support.

The solid support may be attached to the compounds either through the fluorophore or through a reactive group, if present, or through a carrier molecule, if present. Even if a reactive group and/or a carrier molecule are present, the solid support may be attached through the fluorophore.

Solid supports suitable for use herein are typically substantially insoluble in liquid phases. Solid supports for use herein are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtiter plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as SEPHAROSE, poly(acrylate), polystyrene, poly (acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like.

In certain embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the cell-tracker compounds disclosed herein. Useful reactive groups are disclosed above and are equally applicable to the solid support reactive functional groups herein.

A suitable solid phase support may be selected on the basis of desired end use and suitability for various synthetic protocols. For example, where amide bond formation is desirable to attach the cell-tracker compounds disclosed herein to the solid support, resins generally useful in peptide synthesis may be employed, such as polystyrene (e.g., PAM-resin obtained from Bachem Inc., Peninsula Laboratories, etc.), POLYHIPE resin (obtained from Aminotech, Canada), polyamide resin (obtained from Peninsula Laboratories), polystyrene resin grafted with polyethylene glycol (TENTAGEL, Rapp Polymere, Tubingen, Germany), polydimethyl-acrylamide resin (available from Milligen/Biosearch, California), or PEGA beads (obtained from Polymer Laboratories).

F. CONJUGATES AND PREPARATION THEREOF

Another illustrative embodiment provides a process for preparing a conjugated compound disclosed herein, the process comprising reacting a compound disclosed herein as described herein with a substance to be conjugated thereto, thereby resulting in a conjugated substance $S_C$.

The compounds disclosed herein that contain a reactive group $R_X$ are useful to fluorescently label a wide variety of organic substances that contain functional groups with suitable reactivity, resulting in chemical attachment, i.e., conjugation, of the substance (thereby affording a conjugated substance, $S_C$) and formation of reagents that are themselves conjugates. Most preferably, but not exclusively, the conjugated substance disclosed herein is an intracellular amino acid, peptide, protein, nucleotide, oligonucleotide, nucleic acid, lipid, phospholipid, lipoprotein, or lipopolysaccharide. The reactive group and functional group are typically an electrophile and a nucleophile, respectively, that can generate a covalent linkage. Alternatively, the reactive group is a photoactivatable group that becomes chemically reactive only after illumination with light of an appropriate wavelength. Selected examples of functional groups and linkages, where the reaction of an electrophilic group and a nucleophilic group yields a covalent linkage, as well as a general discussion of dye-conjugate chemistry, are provided in U.S. Pat. No. 5,830,912 the disclosure of which is incorporated herein by reference in its entirety.

In certain embodiments, conjugates of the compounds disclosed herein are provided. Conjugates of components (carrier molecules or solid supports), e.g., drugs, peptides, toxins, nucleotides, phospholipids, proteins and other organic molecules are prepared by organic synthesis methods using the cell-tracker compounds disclosed herein, are generally prepared by means well recognized in the art (Haugland, MOLECULAR PROBES HANDBOOK, supra, (2002)). Preferably, conjugation to form a covalent bond consists of mixing the compounds disclosed herein in a suitable solvent in which both the compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformnnamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of peptide or protein conjugates typically comprises first dissolving the protein to be conjugated in aqueous buffer at about 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compound-protein conjugate is tested in its desired application.

Following addition of compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate may be used in solution or lyophilized. In this way, suitable conjugates may be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3:2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate compound. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity may also be obtained by careful control of the reaction conditions.

When modifying polymers with the compounds disclosed herein, an excess of compound is typically used, relative to the expected degree of compound substitution. Any residual, unreacted compound or a compound hydrolysis product is typically removed by dialysis, chromatography or precipitation. Presence of residual, unconjugated compound may be detected by thin layer chromatography using a solvent that elutes the compound away from its conjugate. In all cases it is usually preferred that the reagents be kept as concentrated as practical so as to obtain adequate rates of conjugation.

In certain embodiments, the compound-conjugates disclosed herein are associated with an additional substance, that binds either to the fluorophore or the conjugated substance (carrier molecule or solid support) through non-covalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the compound-conjugate, for example, as a means of enhancing the signal of the compound-conjugate.

G. EXAMPLES

The following are examples of methods, uses, and compositions disclosed herein. It is understood that various other embodiments may be practiced, given the general and detailed descriptions provided above. The following examples are given for the purpose of illustrating the present teachings and shall not be construed as being a limitation on the scope of the disclosure or claims.

A. Synthesis of Compound 1:

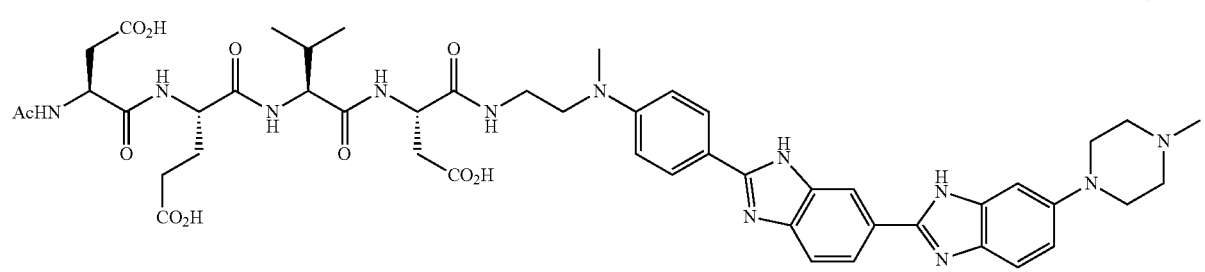

(Compound 1)

Compound 1 was synthesized as follows. See FIG. 1 for a scheme for this synthesis.

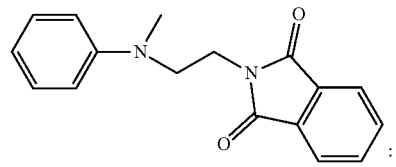 [SMILES: CN(CCN1C(=O)c2ccccc2C1=O)c1ccccc1]

N-methylaniline (0.30 g), N-(2-bromoethyl)phthalimide (1.42 g), and DIEA (1.5 mL) were dissolved in 6 mL of DMF. The reaction was heated to 100° C. for 24 hours. After removal of volatile, the residue was purified by flash chromatography with hexane-ethyl acetate to afford the title compound as yellow solid (yield 75%). H$^1$NMR (CDCl$_3$): δ 7.81 (m, 3H), 7.72 (m, 3H), 7.42 (m, 3H), 4.0 (t, 2H), 3.75 (t, 2H), 3.10 (s, 3H).

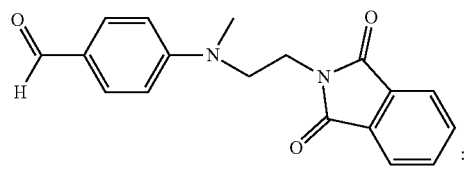 [SMILES: CN(CCN1C(=O)c2ccccc2C1=O)c1ccc(C=O)cc1]

POCl$_3$ (0.4 mL) was added into DMF (0.4 mL) cooled in an ice-bath. The reaction was stirred for 15 min. 2-(2-(methyl(phenyl)amino)ethyl) isoindoline-1,3-dione (1.0 g) dissolved in 4 mL of DMF was added dropwise. The mixture was warmed up to room temperature and heated to 60° C. for 15 min. After the reaction cooled down, it was poured into the aqueous sodium acetate. The solution was stirred for 1 hour. Light yellow solid precipitated. The filtration afforded the title compound as yellow solid (yield 90%). H$_1$NMR (CDCl3): δ 9.8 (s, 1H), 7.80-7.95 (m, 6H), 6.70 (m, 2H), 4.0 (t, 2H), 3.95 (t, 2H), 3.0 (s, 3H).

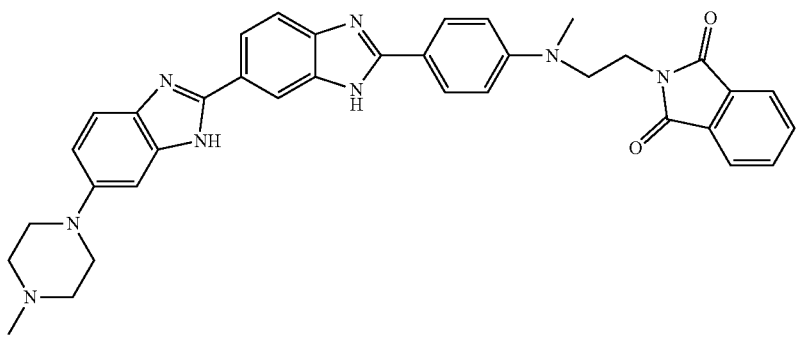 [SMILES: CN1CCN(c2ccc3nc(-c4ccc5nc(-c6ccc(N(C)CCN7C(=O)c8ccccc8C7=O)cc6)[nH]c5c4)[nH]c3c2)CC1]

Na$_2$S$_2$O$_5$ (75 mg) dissolved in 3 mL of water was added into the solution of 4-((2-(1,3-dioxoisoindolin-2-yl)ethyl)(methyl)amino) benzaldehyde (100 mg) and 4-(6-(4-methylpiperazin-1-yl)-1H-benzo[d]imidazol-2-yl)benzene-1,2-diamine (103 mg) in 15 mL of methanol. The reaction was heated to reflux for 24 hours. After the mixture cooled down, methanol was removed in vacuo. The remaining mixture was filtered and washed with water twice to afford the title compound as yellow solid (yield 80%). H$^1$NMR (d6-DMSO): δ 8.30 (s, 1H), 8.0 (m, 2H), 7.82 (m, 4H), 7.64 (d, 3H), 7.50 (d, 2H), 7.16 (s, 1H), 7.03 (d, 1H), 6.87 (d, 2H), 3.92 (t, 2H), 3.84 (t, 2H), 3.3-3.4 (m, 8H), 3.0 (s, 3H), 2.82 (s, 3H).

2-(2-(methyl(4-(6-(4-methylpiperazin-1-yl)-1H, 3H-[2,5'-bibenzo[d]imidazol]-2'-yl)phenyl)amino)ethyl)isoindoline-1,3-dione (200 mg) was mixed with hydrazine (100 mg) and 10 ml of ethanol. The mixture was heated to reflux for 2 hours. After the reaction cooled down, ethanol was removed in vacuo. 15 mL of ethanol was added and then removed via rotary evaporator. The residue was mixed with 4 mL of 1N HCl, then heated to reflux for 1 hour. After the reaction cooled down, the mixture was filtered. The filtrate was concentrated and dried under vacuum to afford the title compound as brown solid which was used for next step without further purification. LCMS: 481.6 (M+1).

2-(methyl(4-(6-(4-methylpiperazin-1-yl)-1H,3'H-[2,5'-bibenzoldlimidazol]-2'-yl)phenyl)amino)ethan-1-aminium (77 mg), tetra-peptideAc-D(OtBu)E (OtBu)VD(OtBu)-OH (110 mg), HATU (65 mg), DIEA (0.4 mL), DMF (6 mL) were mixed and stirred for 2 hours. The solvents were removed in vacuo. The residue was purified by flash chromatography with chloroform-methanol containing 0.1% triethylamine to afford the title compound as yellow solid (yield 55%). LCMS: 1150.4 (M+1).

(Compound 1)

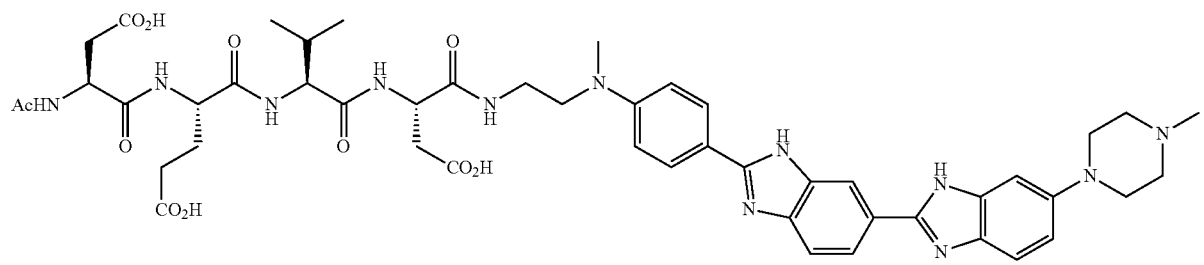 [SMILES: CC(=O)N[C@@H](CC(=O)OC(C)(C)C)C(=O)N[C@@H](CCC(=O)OC(C)(C)C)C(=O)N[C@H](C(=O)N[C@@H](CC(=O)OC(C)(C)C)C(=O)NCCN(C)c1ccc(-c2nc3ccc(-c4nc5ccc(N6CCN(C)CC6)cc5[nH]4)cc3[nH]2)cc1)C(C)C]

tert-butyl (7S,10S,13S,16S)-16-acetamido-7-(2-(tert-butoxy)-2-oxoethyl)-13-(3-(tert-butoxy)-3-oxopropyl)-10-isopropyl-2-(4-(6-(4-methylpiperazin-1-yl)-1H,3'H-[2,5'-bibenzo[d] imidazol]-2'-yl)phenyl)-6,9,12,15-tetraoxo-2,5,8,11,14-pentaazaoctadecan-18-oate (80 mg) was dissolved in 4 mL of dichloromethane and cooled to 0° C. TFA (4 mL) was added dropwise over 1-2 mins. The reaction was stirred for 2 hours. After removal of solvents, the residue was purified by reverse phase flash chromatography with water-acetonitrile containing 0.1% TFA to afford the title compound as yellow solid (yield 50%). H$^1$NMR (d6-DMSO): δ 8.32 (s, 1H), 8.24 (m, 2H), 8.1 (m, 2H), 8.03 (m, 2H), 7.80 (m, 3H), 7.6 (d, 2H), 7.53 (d, 2H), 7.12 (s, 1H), 7.0 (d, 1H), 6.83 (d, 2H), 4.2-4.3 (m, 4H), 3.90 (t, 2H), 3.81 (t, 2H), 3.3-3.4 (m, 8H), 3.0 (s, 3H), 2.8 (s, 3H), 2.2-2.4 (m, 6H), 2.0 (s, 3H), 1.42 (m, 2H), 1.32 9 m, 1H), 0.92 (d, 6H). LCMS: 981.1 (M+1).

B. Synthesis of Compound 2:

(Compound 2)

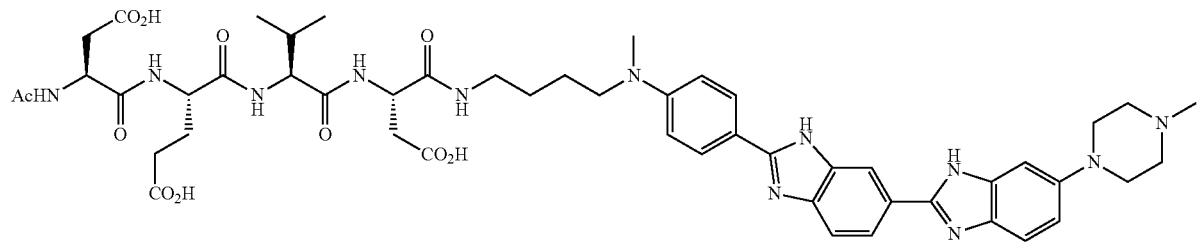

Compound 2 was synthesized in a manner analogous to Compound 1 as described above in Example A.

C. Synthesis of Compound 9:

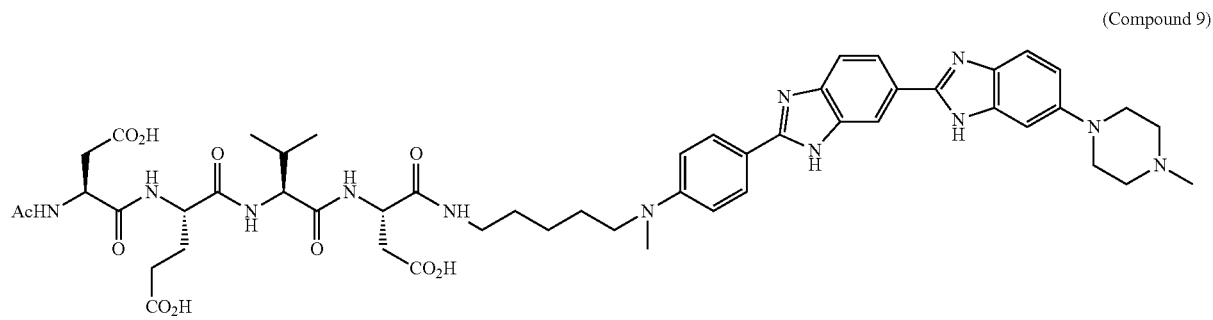 [SMILES: CC(=O)N[C@@H](CC(=O)O)C(=O)N[C@@H](CCC(=O)O)C(=O)N[C@H](C(=O)N[C@@H](CC(=O)O)C(=O)NCCCCCN(C)c1ccc(-c2nc3ccc(-c4nc5ccc(N6CCN(C)CC6)cc5[nH]4)cc3[nH]2)cc1)C(C)C]
(Compound 9)

Compound 9 was synthesized in a manner analogous to Compound 1 as described above in Example A.

D. Synthesis of Compound 3:

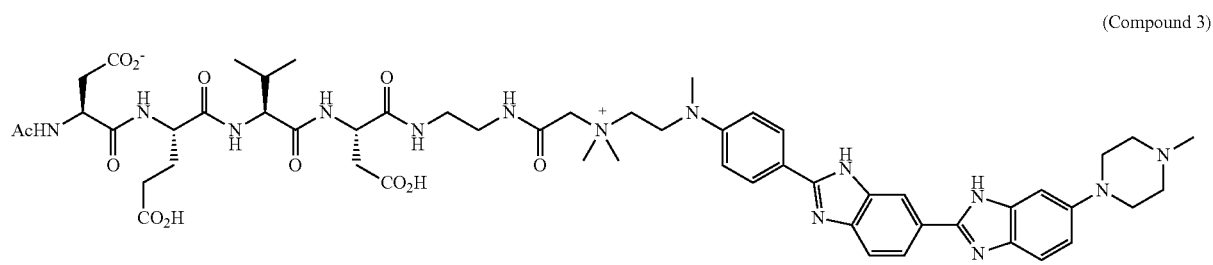
(Compound 3)

Compound 3 was synthesized in a manner analogous to Compound 1 as described above in Example A.

E. Synthesis of Compound 4:

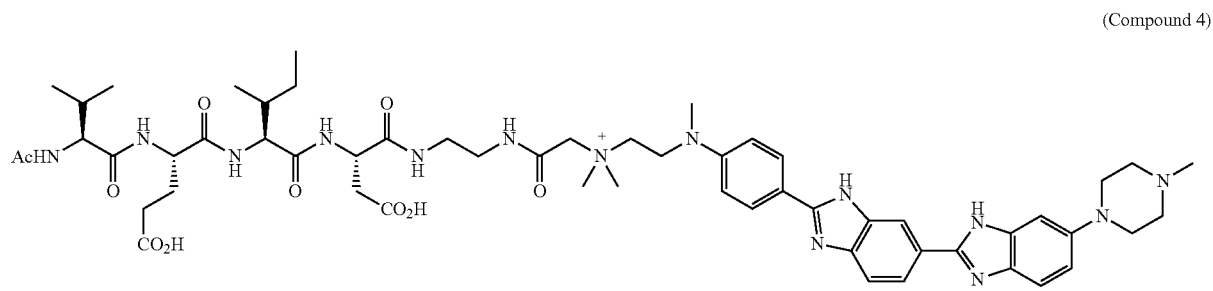
(Compound 4)

Compound 4 was synthesized in a manner analogous to Compound 1 as described above in Example A.

F. Synthesis of Compound 8:

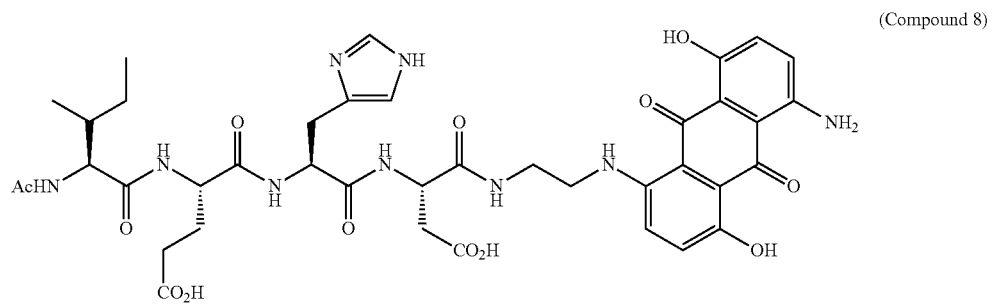 [SMILES: CCC(C)[C@H](NC(C)=O)C(=O)N[C@@H](CCC(=O)O)C(=O)N[C@@H](Cc1c[nH]cn1)C(=O)N[C@@H](CC(=O)O)C(=O)NCCNc1ccc(O)c2c1C(=O)c1c(O)ccc(N)c1C2=O]
(Compound 8)

Figure 2:
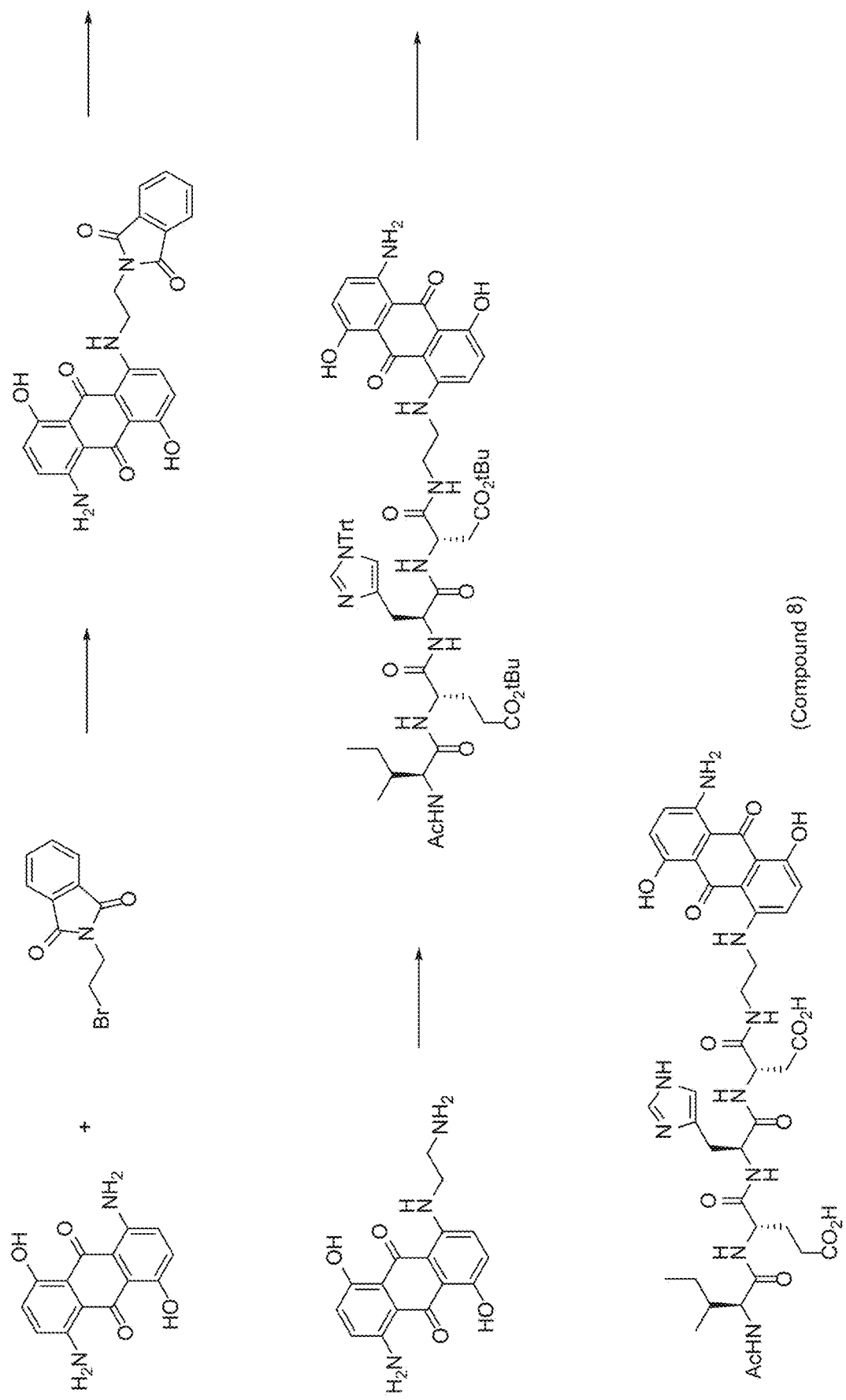
FIG. 2 shows the synthetic scheme for the synthesis of Compound 8 described in Example E.

Compound 8 was synthesized as follows. See FIG. 2 for a scheme for this synthesis.

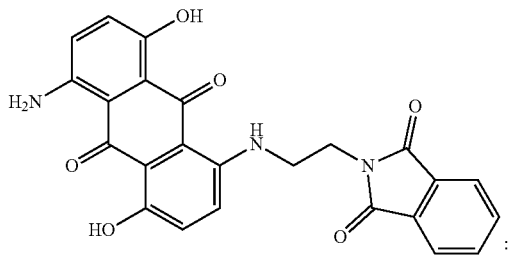 [SMILES: Nc1ccc(O)c2c1C(=O)c1c(O)ccc(NCCN3C(=O)c4ccccc4C3=O)c1C2=O]

1,5-dihydroxy-4,8-diaminoanthraquinone (0.30 g), N-(2-bromoethyl)phthalimide (0.56 g) and DMF (5 mL) were mixed and heated to 110° C. for 24 hours. After the reaction cooled down to room temperature, the solution was added into diethyl ether (30 mL) dropwise. The precipitate was obtained after centrifugation. The process was repeated twice to afford the title compound (0.30 g, 61%) as blue solid. H$^1$NMR (d6-DMSO): δ 7.91 (m, 4H), 6.8-7.1 (m, 4H), 6.4 (s, 2H), 3.52 (t, 2H), 3.41 (t, 2H).

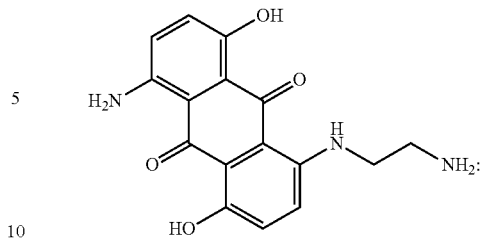

2-(2-((5-amino-4,8-dihydroxy-9,10-dioxo-9,10-dihydroanthracen-1-yl)amino)ethyl)isoindoline-1,3-dione (0.25 g), hydrazine (0.18 g) and ethanol (5 mL) was heated to reflux for 2 hours. After the reaction cooled down, the volatile was removed via rotary evaporation. 10 mL of ethanol was added and evaporated. This process was repeated twice. 2 mL of 1N HCl was added into the residue and then refluxed for 1 hour. After the reaction mixture cooled down to room temperature, it was filtered through Buchner funnel. The filtrate was concentration to afford the title compound which was used without purification for next step.

LCMS: 314.3 (M+1).

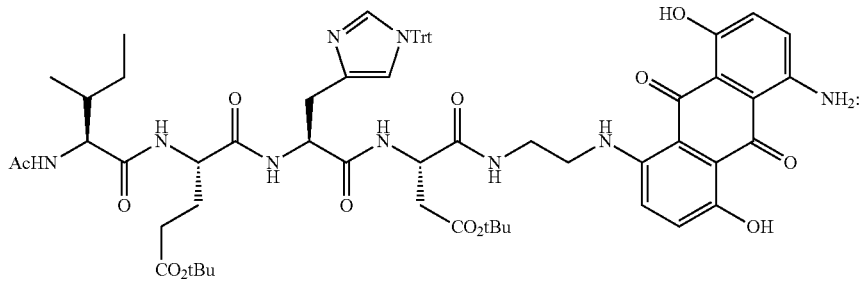

1-amino-5-((2-aminoethyl)amino)-4,8-dihydroxyanthracene-9,10-dione (20 mg), Ac-LEHD (70 mg), HATU (45 mg), DIEA (0.2 mL), DMF (3 mL) were mixed and stirred for 2 hours. After reaction was complete, the volatile was removed. The residue was purified by flash chromatography with chloroform-methanol to afford the title compound (40 mg). LCMS: 1205 (M+1).

(Compound 8)

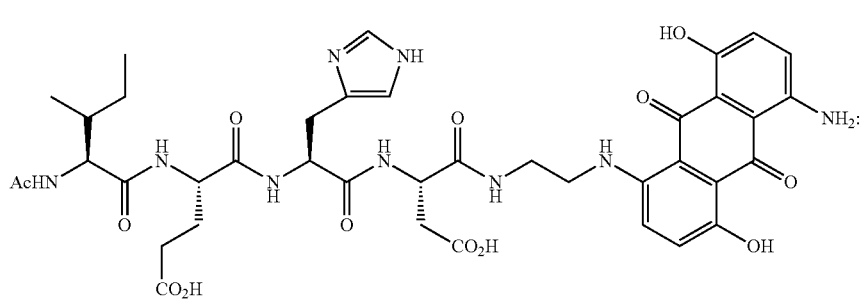

tert-butyl (4S,7S,10S,13S)-13-((2-((5-amino-4,8-dihydroxy-9,10-dioxo-9,10-dihydroanthracen-1-yl)amino)ethyl)carbamoyl)-7-(3-(tert-butoxy)-3-oxopropyl)-4-((R)-sec-butyl)-2,5,8,11-tetraoxo-10-((1-trityl-1H-imidazol-4-yl)methyl)-3,6,9,12-tetraazapentadecan-15-oate (30 mg) was mixed with dichloromethane (3 mL) and cooled down in an ice bath. TFA (3 mL) was added dropwise. The reaction was stirred for 2 hours. After the volatile was removed, the residue was purified by reverse phase flash chromatography with 0.1% TFA-water-Acetonitrile to afford the title compound (21 mg) as blue powder. H¹NMR (d6-DMSO): δ 12-13 (m, 3H), 8.61 (s, 1H), 8.2-3 (m, 4H), 7.82 (s, 1H), 6.8-7.0 (m, 4H), 6.3 (s, 2H), 4.4-4.5 (m, 4H), 3.45 (m, 4H), 3.01 (t, 2H), 2.92 (m, 2H), 2.50 (m, 2H), 2.43 (m, 2H), 2.1 (m, 2H), 2.0 (s, 3H), 1.72 (m, 2H), 1.0-1.1 (m, 6H). LCMS: 850.9 (M+1).

G. Synthesis of Compound 5:

(Compound 5)

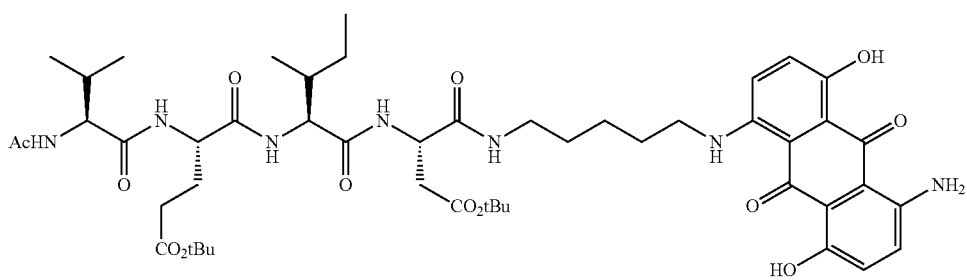

Compound 5 was synthesized in a manner analogous to Compound 8 as described above in Example F.

H. Synthesis of Compound 6:

(Compound 6)

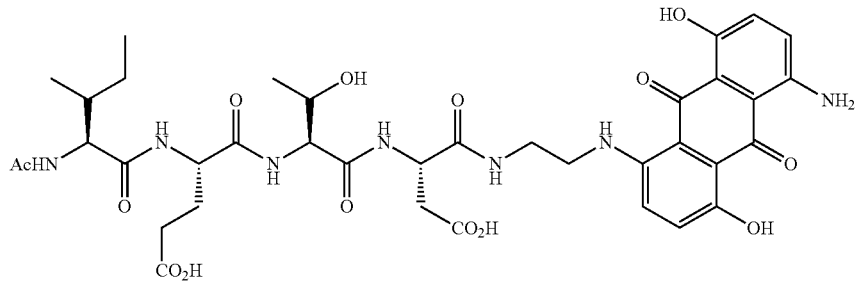

Compound 6 was synthesized in a manner analogous to Compound 8 as described above in Example F.

I. Synthesis of Compound 7:

(Compound 7)

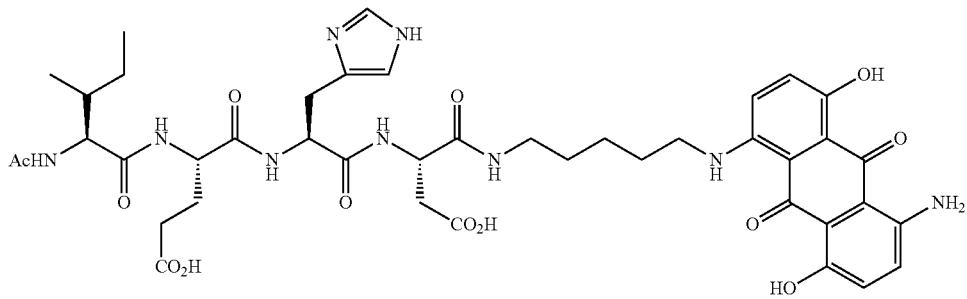

Compound 7 was synthesized in a manner analogous to Compound 8 as described above in Example F.

J. Flow Cytometric Detection of Caspase Activity and Apoptosis:

To demonstrate the ability of Compound 1 to recognize apoptotic populations, Jurkat cells were treated with varying concentrations of Staurosporine over a range from less than $10^{-6}$ M to about $10^{-4}$ M (n=3 for each concentration tested) and compared to an identical population of cells incubated with commercially available CELLEVENT™ Green 3/7 (Thermo Fisher Scientific, Waltham, Mass.).

Jurkat cells in log phase were resuspended in complete medium (RPMI-1640, supplemented with 10% Fetal Bovine Serum, 2 mM L-glutamine & 55 U/mL) and adjusted to a concentration of $2\times10^6$ cells per milliliter. 100 µl of cells were aliquoted in each well of a 96-well, V-bottom microplate so that 8 dilutions in triplicate were tested for each substrate.

Drug dilutions for treating cells were created by adding 1000 µL of complete medium containing 2 µM Staurosporine, 1:2 dilutions of this were added to 500 µL of complete medium, so that a series of 8 dilutions of Staurosporine were created.

100 µL of the media/Staurosporine mixtures were added to each well so that 3 wells of cells contained the highest dose, and then repeated for the next set of 3 wells.

Cells were incubated at 37° C., 5% $CO_2$ in a standard cell culture incubator for 4 hours.

After the 4 hour incubation, each well had 1 µL of caspase substrate added so that the final concentration of the substrate was 2 µM of substrate in 200 µL of media.

Cells were incubated at 37° C., 5% $CO_2$ in a standard cell culture incubator for 30 minutes.

At the end of the incubation, cells were analyzed using an ATTUNE® NXT Acoustic Focusing Cytometer (Thermo Fisher Scientific, Waltham. Mass.) using the 488 nm excitation and 530/30 nm emission filters to detect CELLEVENT™ Green, or the 405 nm excitation laser and the 440/50 nm emission filters to detect Compound 1. Via the cytometer software, cells were gated such that intact, single cells were used for analysis. Gates to detect the positive cells were set upon stained, but untreated/negative control cells such that cells that fluoresced in the appropriate wavelength, with a mean fluorescent intensity greater than 1-log above the negative population was considered positive. A percent positive of intact-single cells is reported.

Figure 3:
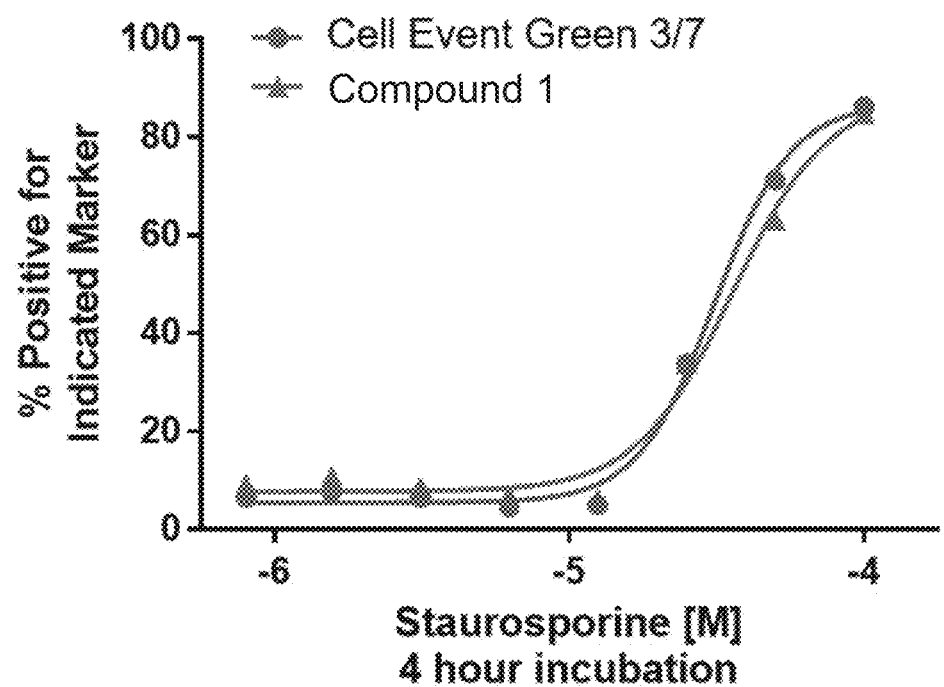
FIG. 3 shows a comparison of the ability of Compound 1 and commercially available CELLEVENT™ Green 3/7 (Thermo Fisher Scientific, Waltham, Mass.) to recognize apoptotic populations of Jurkat cells treated with varying concentrations of staurosporine.
Figure 4A:
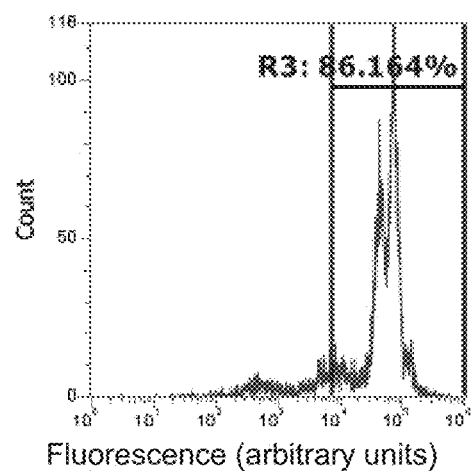
FIGS. 4A and 4B show flow cytometry results for cells treated with staurosporine and stained with either CELLEVENT™ Green 3/7 (FIG. 4A) or Compound 1 (FIG. 4B).
Figure 4B:
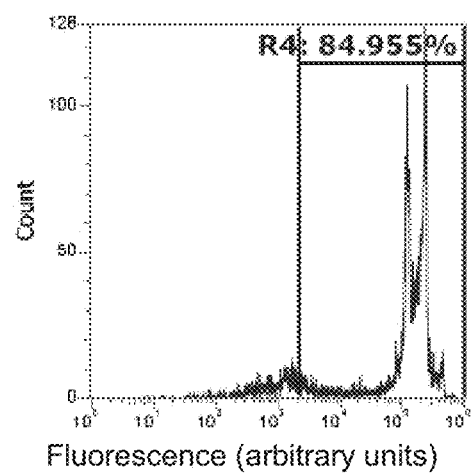

As shown in FIG. 3, there was essentially no difference over the entire staurosporine concentration range tested between the detection of apoptosis in Jurkat cells using either CELLEVENT™ Green 3/7 or Compound 1 substrates. For example, flow cytometry results for cells treated with 1 µM staurosporine and stained with CELLEVENT™ Green 3/7 (FIG. 4A) or Compound 1 (FIG. 4B) showed similar levels of positive cells (86.2% and 84.9%, respectively) in which Compound 1 entered the cells, was cleaved, bound nuclear DNA, and fluoresced. Gating was performed by using untreated, stained cells to set the positive gate.

Figure 5A:
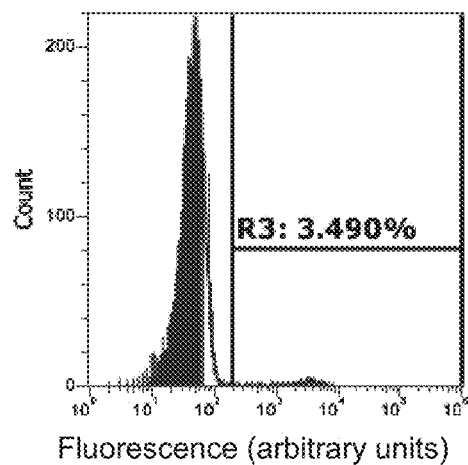
FIGS. 5A and 5B show flow cytometry results for cells treated with 1 μM staurosporine (FIG. 5A) or not treated (FIG. 5B) and stained with Compound 1.
Figure 5B:
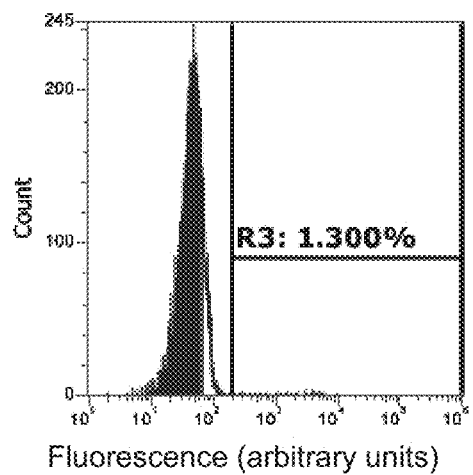

In another experiment, Jurkat cells treated with 1 µM Staurosporine for 1 hour (FIG. 5A) or untreated control cells (FIG. 5B) were then treated with Compound 1. Cells were then analyzed on an ATTUNE® NXT flow cytometer. The cells were oriented on a SSC/FSC plot to include both low and high side scatter cells, but to exclude debris and gated to exclude doublets (not shown). Histograms demonstrate an increase in Compound 1 positive cells for the Staurosporine-treated cells (3.49%, FIG. 5A) relative to the untreated control cells (1.30%, FIG. 5B). Density plots also showed an increase in the positive population of the staurosporine-treated cells relative to the untreated control cells (3.55% versus 1.32%; not shown).

Figure 6A:
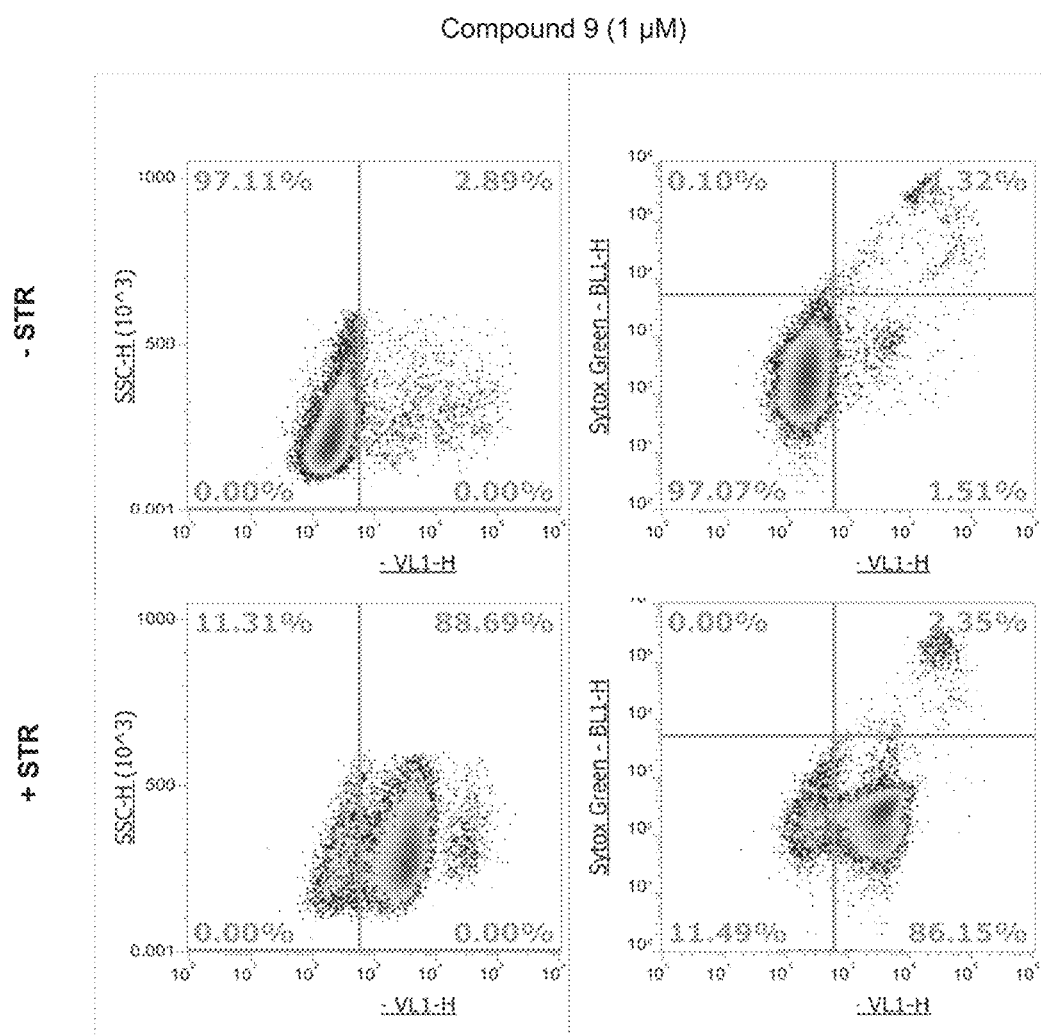
FIGS. 6A and 6B show flow cytometry results for Jurkat cells treated with 0.5 μM staurosporine (+STR) or without 0.5 μM staurosporine (–STR) and stained with Compound 9 (FIG. 6A) or CELLEVENT™ Green 3/7 (FIG. 6B) each at 1 μM final concentration.
Figure 6B:
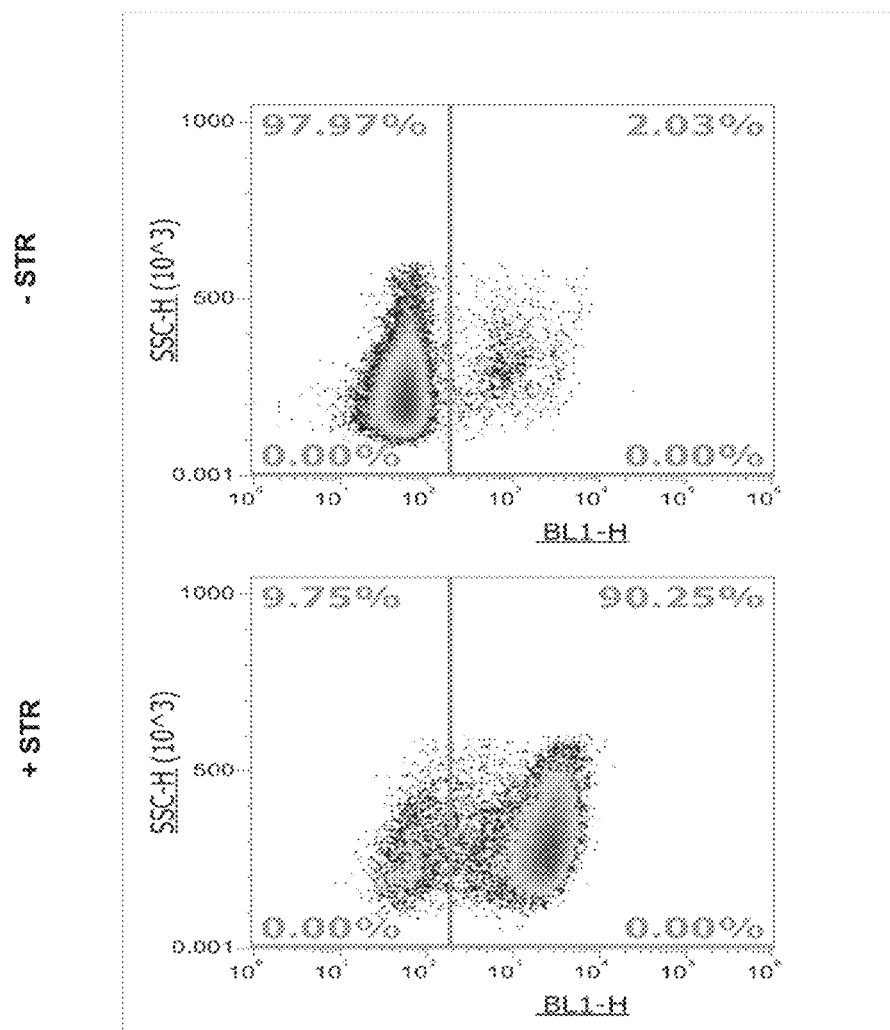

In another experiment. Jurkat cells were resuspended at $1\times10^6$ cells/mi in RPMI medium+10% FBS and aliquoted into 0.2 ml samples. The cells were treated with 0.5 µM Staurosporine (+STR) or without (−STR) and then each sample was treated for 4 hours at 37° C. with Compound 9 (FIG. 6A) or CELLEVENT™ Green 3/7 (FIG. 6B), each at a final concentration of 1 µM. The cells were then analyzed on an ATTUNE™ NXT flow cytometer as described above and analyzed without washing. Histograms show a ≥1 log difference between normal an apoptotic cells for both Compound 9 (FIG. 6A) and CELLEVENT™ Green 3/7 (FIG. 6B).

Figure 7A:
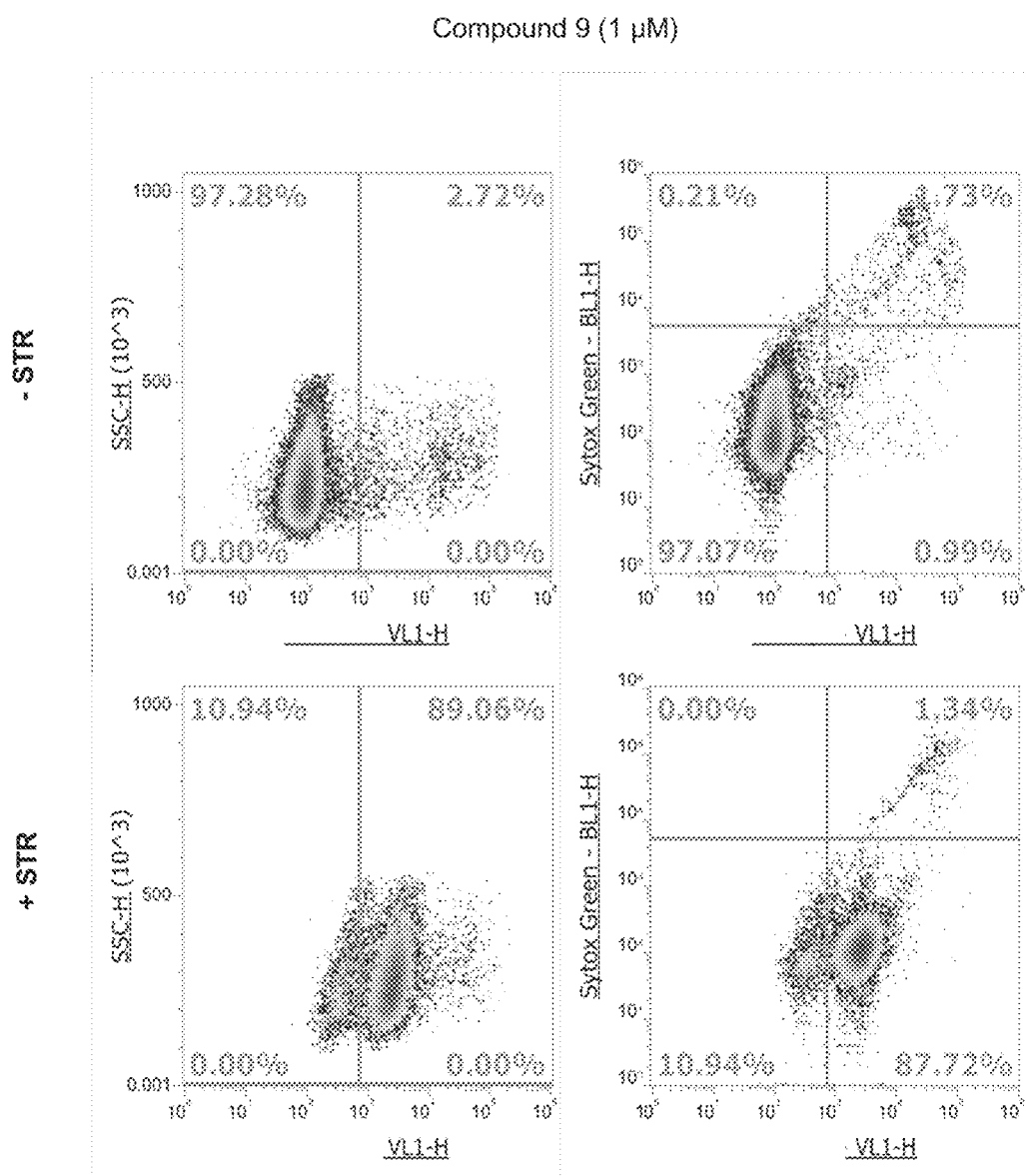
FIGS. 7A and 7B show flow cytometry results for Jurkat cells treated with 0.5 μM staurosporine (+STR) or without 0.5 μM staurosporine (–STR) and stained with Compound 9 (FIG. 7A) or CELLEVENT™ Green 3/7 (FIG. 7B) each at 1 μM final concentration, followed by addition of 1 μl SYTOX Dead Cell Stain (Thermo Fisher Scientific. Waltham, Mass.).
Figure 7B:
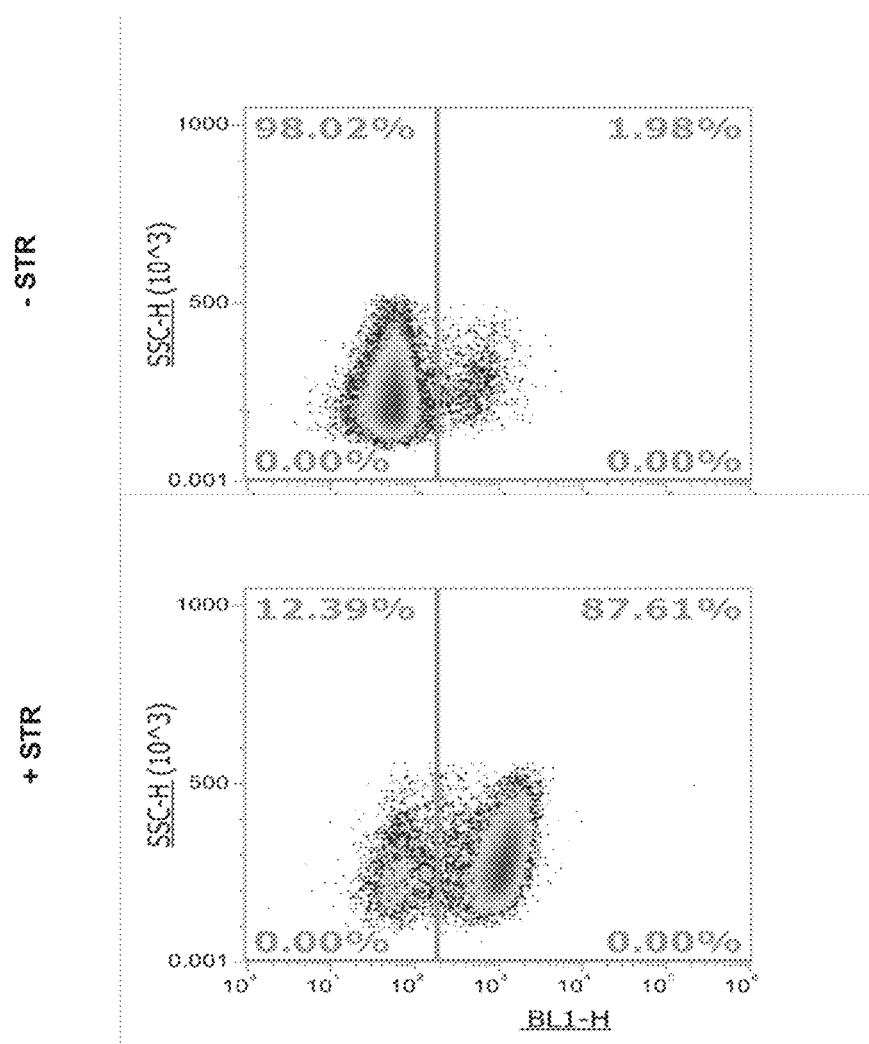

In yet another experiment, Jurkat cells were resuspended at $1\times10^6$ cells/ml in RPMI medium+10% FBS and aliquoted into 0.2 ml samples. The cells were treated with 0.5 µM Staurosporine (+STR) or without (−STR) for 3.5 hours at 37° C. The cells were then treated with either Compound 9 (FIG. 7A) or CELLEVENT™ Green 3/7 (FIG. 7B), each at a final concentration of 1 µM and incubated at 37° C. for an additional 30 min. 1 µl SYTOX™ Dead Cell Stain (Thermo Fisher Scientific, Waltham. Mass.) was added to the cells and incubated for at least 15 min. Cells were analyzed on an ATTUNE™ NXT flow cytometer as described above and were analyzed without washing. As shown in the histograms, both Compound 9 (FIG. 7A) and CELLEVENT™ Green 3/7 (FIG. 7B) distinguished non-apoptotic from apoptotic cell populations.

Figure 8A:
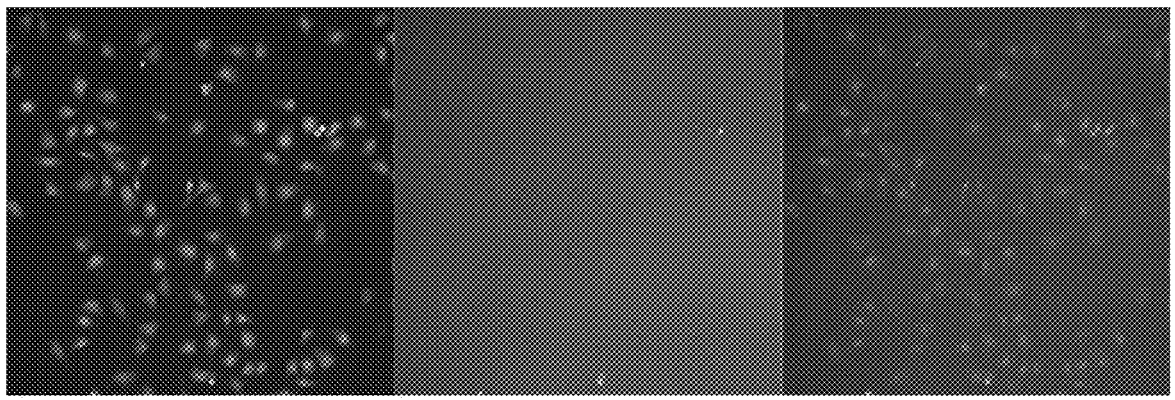
FIGS. 8A and 8B show fluorescence microscopy results for HeLa cells treated for 18 hours with 1 nM staurosporine (FIG. 8A) or 1 μM staurosporine (FIG. 8B) and stained with SYTO®82 nuclear stain (left panels of FIGS. 8A and 8B) and Compound 1 (center panels of FIGS. 8A and 8B). The right panels of FIGS. 8A and 8B show composite overlays of the left and center panels.
Figure 8B:
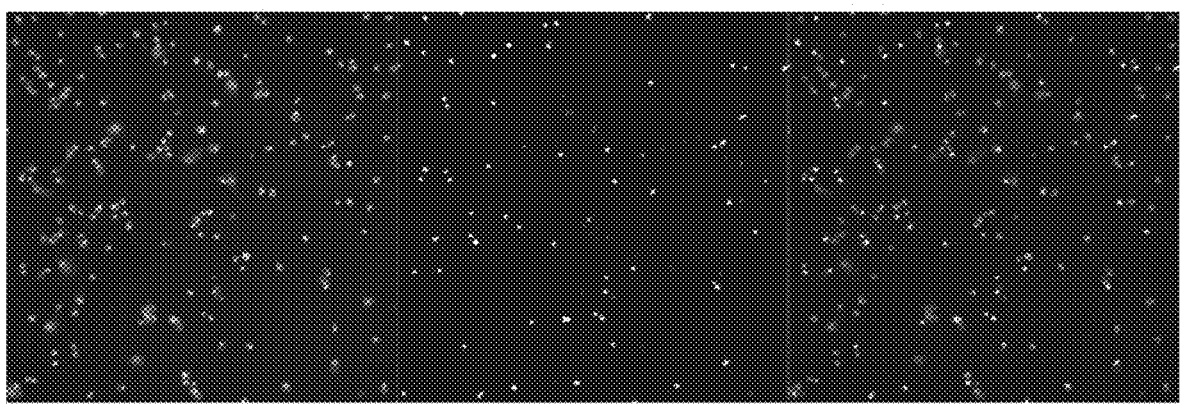

K. Fluorescence Microscopy Detection of Caspase Activity and Apoptosis:

HeLa cells at a density of 7500 cells/well were incubated overnight in growth media (MEM+10% FBS. L-glutamine and Pen-Strep). Half of the plate was treated with 1 µM Staurosporine (FIG. 8B), while the other half was treated with 1 nM Staurosporine (FIG. 8A). After an 18 hour incubation (37° C., 5% $CO_2$), all cells were incubated with SYT®82 (FIGS. 8A and 8B, left panels) and Compound 1 (FIGS. 8A and 8B, center panels). The average intensity of Compound 1 in the cellular nuclear region was calculated using HCSStudio (Compartmental Analysis Bioapplication), and a Z' was determined (Z'=0.63).

Figure 9A:
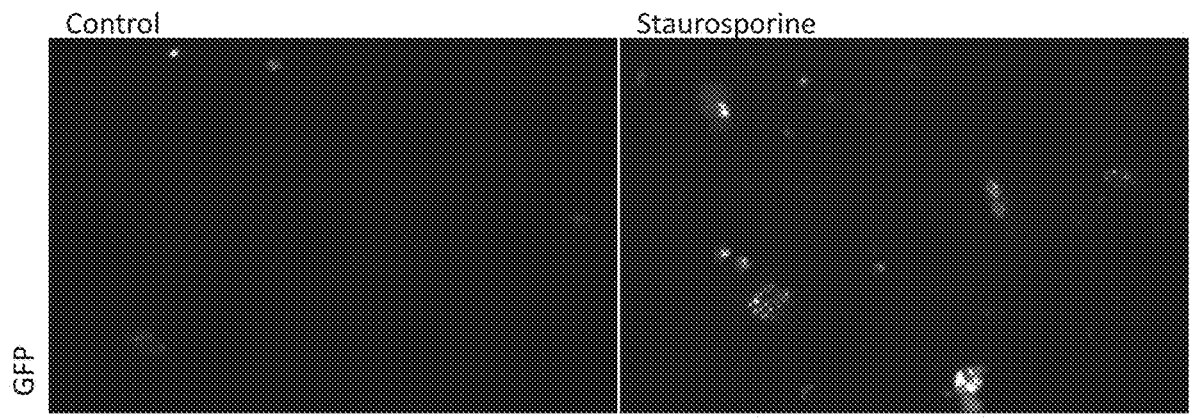
FIGS. 9A, 9B, 9C and 9D show fluorescence microscopy results for HeLa cells treated for 5 hours with 10 μM staurosporine ("Staurosporine") or without ("Control") and stained with CELLEVENT™ Green 3/7 (FIG. 9A), Compound 1 (FIG. 9B) or Compound 9 (FIG. 9C).
Figure 9B:
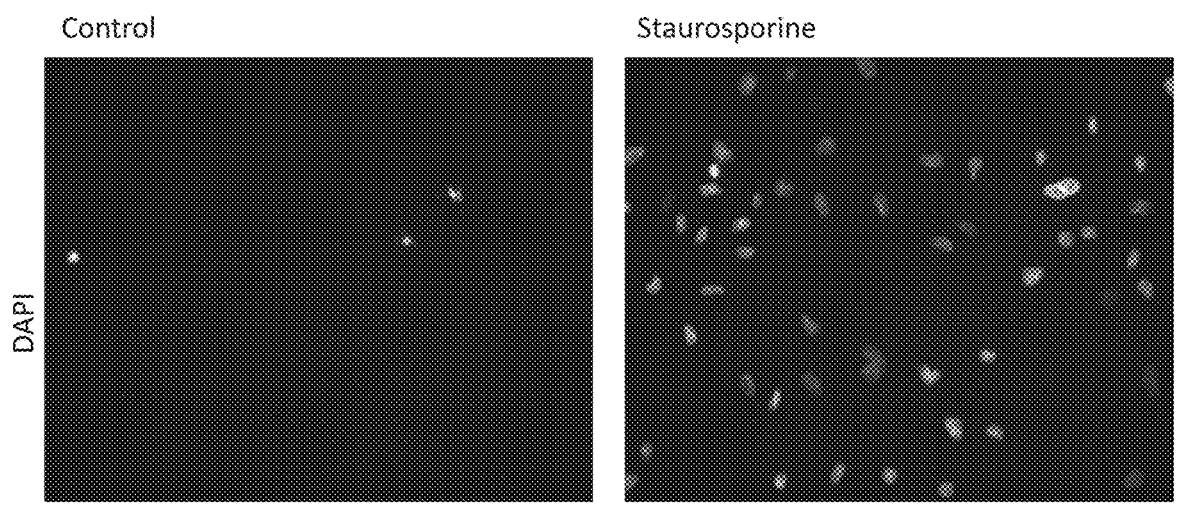
Figure 9C:
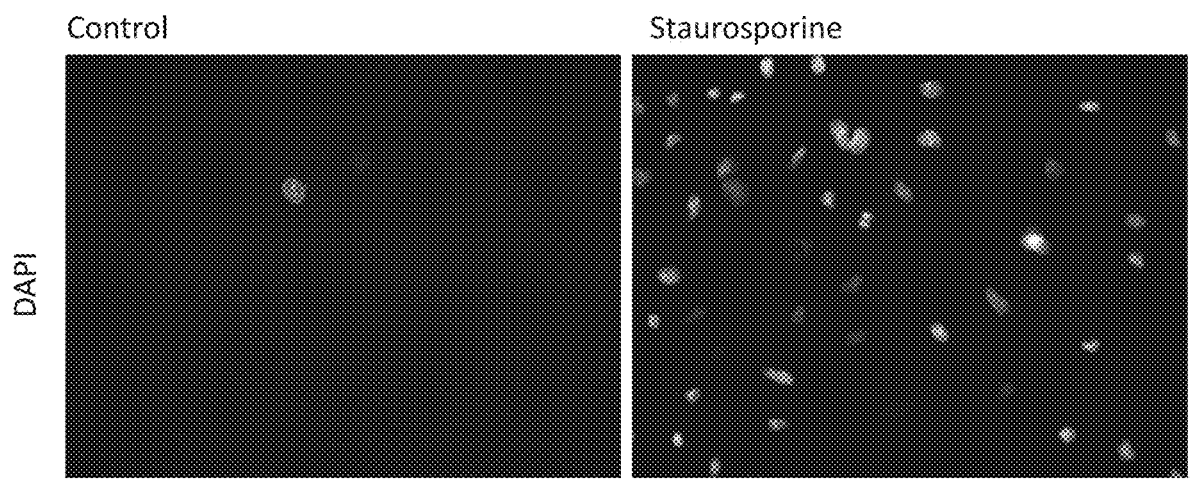
Figure 9D:
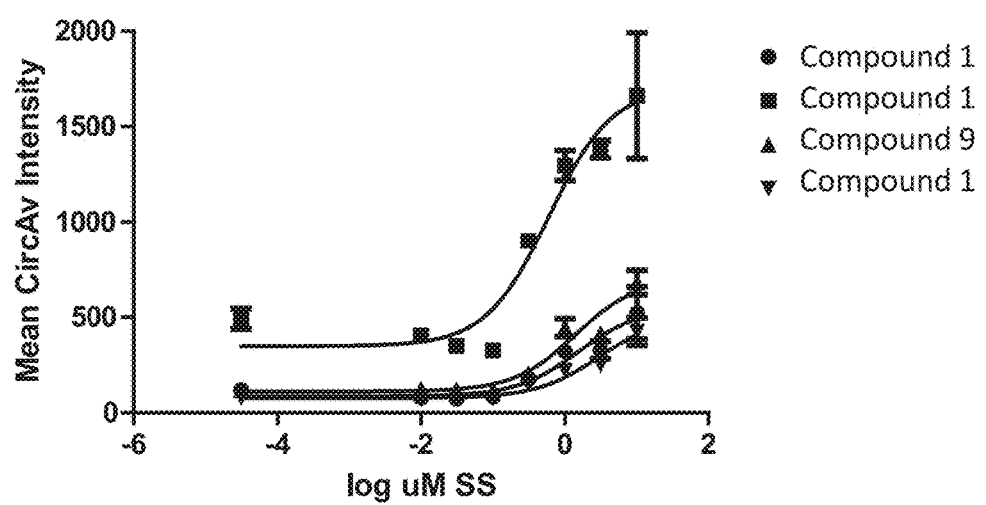

In another experiment, HeLa cells were incubated overnight in growth media (DMEM+10% FBS). A working stock solution of Staurosporine (SS) was prepared at 1:10 into 50 µM dye in LCIS (depending on the experiment, the dye was Compound 1 (FIG. 9B), Compound 9 (FIG. 9C) or CELLEVENT™ Green 3/7 (FIG. 9A)) to use in a dose-response experiment. The dye/staurosporine stock solution was diluted 1:10 onto HeLa cells in complete media for a final concentration starting at 5 µM Compound 1 or Compound 9, or 4 µM CELLEVENT Green 3/7 and 10 µM staurosporine and ending at 0 µM staurosporine. After a 5 hour incubation at 37° C., live cells were imaged using white light, DAPI and FITC filters. The cells were then fixed and stained with HCS CELLMASK™ Deep Red stain (Thermo Fisher Scientific, Waltham, Mass.) and quantified on a CELLINSIGHT™ CX5 High Content Screening (HCS) Platform (Thermo Fisher Scientific, Waltham, Mass.). The imaging results show that Compound 1 (FIG. 9B), Compound 9 (FIG. 9C) and CELLEVENT™ Green 3/7 (FIG. 9A) all recognize apoptotic cells and the dose-response curve of staurosporine (FIG. 9D) shows good induction of apoptosis for Compound 1 (circle, square, and upside-down triangle) and Compound 9 (right-side-up triangle).

Figure 10A:
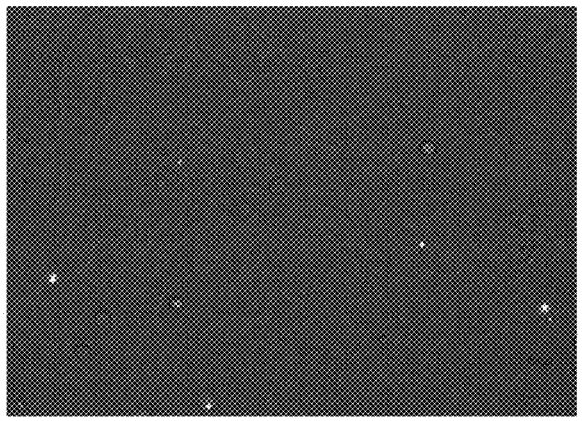
FIGS. 10A, 10B and 10C show fluorescence microscopy results for BPAEC cells were incubated for 2 days in complete media containing 5 μM CELLEVENT™ Green 3/7 (FIG. 10A), Compound 1 (FIG. 10B) or Compound 9 (FIG. 10C) and then treated with 1 μM staurosporine ("staurosporine") or DMSO ("DMSO Control).
Figure 10A:
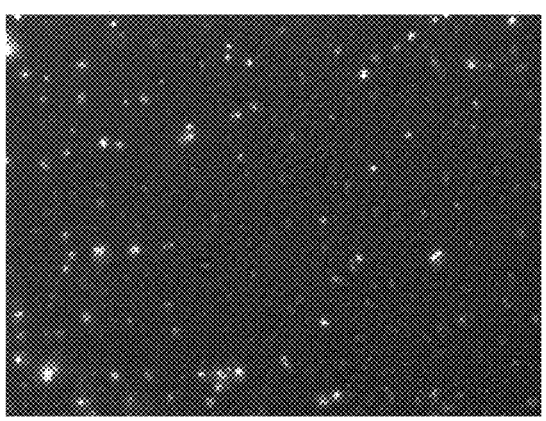
Figure 10B:
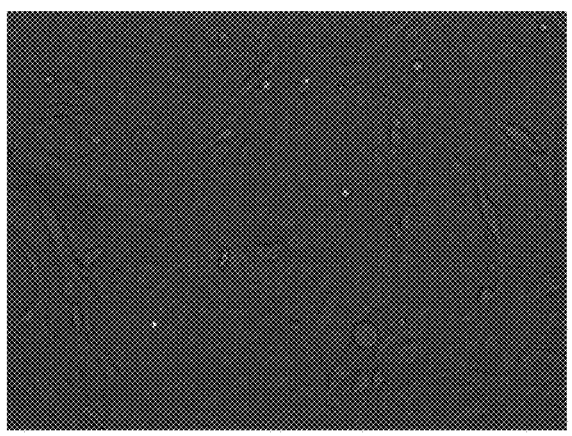
Figure 10B:
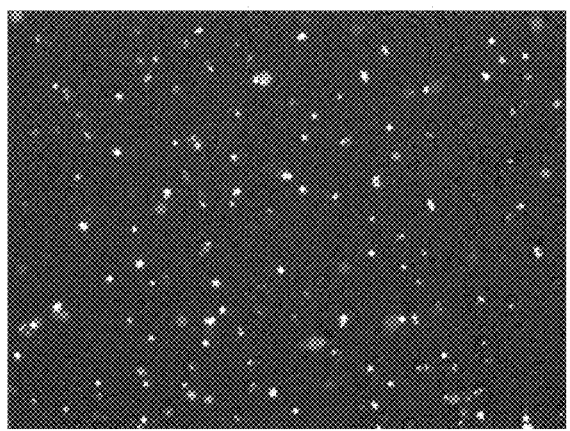
Figure 10C:
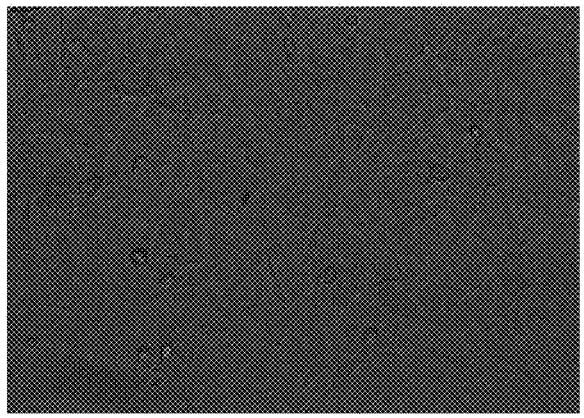
Figure 10C:
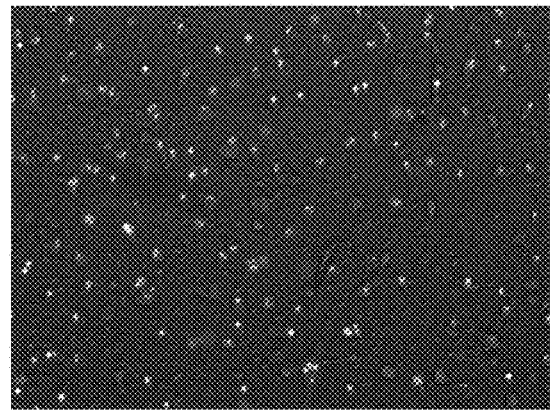

In another experiment to look at dye toxicity. BPAEC cells were incubated overnight in growth media (DMEM+ 10% FBS). The following day, Compound 1, Compound 9 or CELLEVENT™ Green 3/7 was added to cells at a final concentration of 5 μM and incubated for 48 hours at 37° C. After the 48 hour incubation, DMSO (control) or 1 μM staurosporine (final concentration) was added to a subset of the dye-treated cells and incubated overnight at 37° C. The cells were imaged on an EVOS™ FL Auto 2 Imaging System (Thermo Fisher Scientific, Waltham, Mass.), The results demonstrated that none of the dyes had a deleterious effect on cell health and were able to detect the staurosporine-induced apoptotic cells—FIG. 10A shows CELLEVENT Green 3/7, FIG. 10B shows Compound 1, FIG. 10C shows Compound 9.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 4

Description of Sequences

| SEQ ID NO | Description | Sequence |
| --- | --- | --- |
| 1 | Peptide with caspase recognition/cleavage sequence, e.g., for Caspase 3/7 | DEVD |
| 2 | Peptide with caspase recognition/cleavage sequence, e.g., for Caspase 9 | LEHD |
| 3 | Peptide with caspase recognition/cleavage sequence, e.g., for Caspase 3/7 | DEVDG |
| 4 | Peptide with caspase recognition/cleavage sequence, e.g., for Caspase 3/7 | GDEVDGIK |
| 5 | Peptide with caspase recognition/cleavage sequence | $X_2EX_1D$, wherein $X_2$ is W, Y, I, L, D, or V, and $X_1$ is any amino acid |
| 6 | Peptide with caspase recognition/cleavage sequence | $X_3DEX_1D$, wherein $X_3$ is V or L and $X_1$ is any amino acid |
| 7 | Peptide with caspase recognition/cleavage sequence | $DX_1VD$, wherein $X_1$ is any amino acid |
| 8 | Peptide with caspase recognition/cleavage sequence | $DX_2EX_1D$, wherein $X_2$ is W, Y, I, L, or V, and $X_1$ is any amino acid |
| 9 | Peptide with caspase recognition/cleavage sequence, e.g., for Caspase 1/5 | WEHD |
| 10 | Peptide with caspase recognition/cleavage sequence, e.g., for Caspase 1 | YVAD |
| 11 | Peptide with caspase recognition/cleavage sequence, e.g., for Caspase 1 | YVHD |
| 12 | Peptide with caspase recognition/cleavage sequence, e.g., for Caspase 2 | VDVAD |
| 13 | Peptide with caspase recognition/cleavage sequence, e.g., for Caspase 8 | IETD |
| 14 | Peptide with caspase recognition/cleavage sequence, e.g., for Caspase 6 | VEID |
| 15 | Peptide with caspase recognition/cleavage sequence, e.g., for Caspase 4/9 | LEVD |
| 16 | Peptide with caspase recognition/cleavage sequence, e.g., for Caspase 10 | AEVD |
| 17 | Peptide with caspase recognition/cleavage sequence, e.g., for Caspase 8 | DIETD |
| 18 | Peptide with caspase recognition/cleavage sequence, e.g., for Caspase 9 | DLEHD |
| 19 | Peptide with caspase recognition/cleavage sequence, e.g., for Caspase 1 | DYVAD |
| 20 | Peptide with caspase recognition/cleavage sequence | $DX_2VX_1D$, wherein $X_2$ is W, Y, I, L or V and $X_1$ is any amino acid. |
| 21 | Peptide with caspase recognition/cleavage sequence | $(AA)_n$-DEVDG-$(AA)_m$, wherein (AA) is any amino acid, m and n are each independently 0-100. |
| 22 | Cleaved peptide fragment after treatment with caspase | $(AA)_n$-DEVD, wherein (AA) is any amino acid and n is 0-100 |
| 23 | Cleaved peptide fragment after treatment with caspase | G-$(AA)_m$, wherein (AA) is any amino acid and m is 0-100 |
| 24 | Peptide with caspase recognition/cleavage sequence | DXXXD, wherein: first X is W, V, I, L, V or D second X is E or V third X is any amino acid |

What is claimed is:

1. A method for detecting the presence or absence of a caspase enzyme in a cell or mixture of cells, measuring the activity of a caspase enzyme in a cell or mixture of cells, or detecting the presence or absence of apoptosis in a cell or mixture of cells, the method comprising the steps of:

a) incubating the cell or mixture of cells with a compound of structural formula (I):

a compound of structural formula (II):

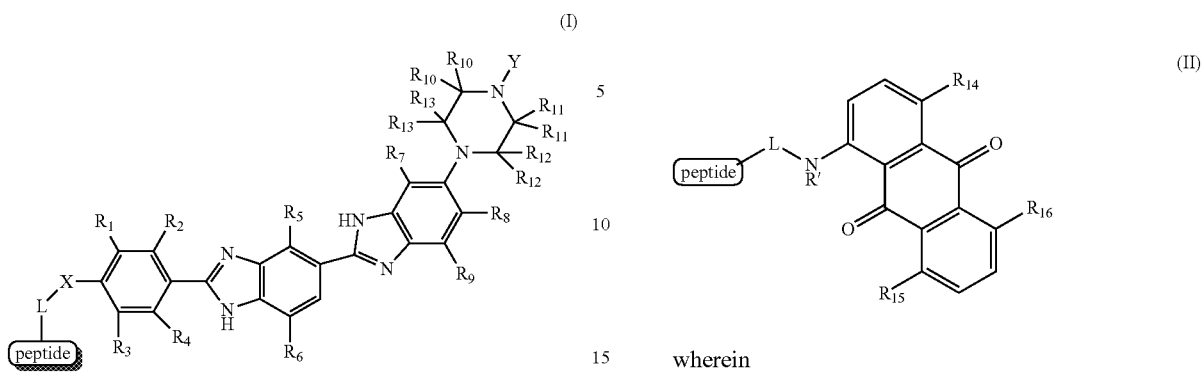

wherein
Y is alkyl or substituted alkyl;

X is —CH$_2$—, —O—, or —N(R)—, wherein R is H, halogen, alkyl or substituted alkyl;

L is a linker; and each R$_1$, R$_2$, R$_3$, R$_4$, R$_5$, R$_6$, R$_7$, R$_8$, R$_9$, R$_{10}$, R$_{11}$, R$_{12}$ and R$_{13}$ is independently H, halogen, alkyl or substituted alkyl; and wherein
R$_{14}$, R$_{15}$, and R$_{16}$ are each independently —OH or —NH$_2$;
R' is H, alkyl or substituted alkyl; and
L is a linker; and b) providing a stimulus to the cell or mixture of cells to elicit a fluorescent signal; and c) measuring the fluorescent signal, whereby the presence or absence of the caspase enzyme is detected, the activity of the caspase enzyme is measured, or the presence or absence of apoptosis is detected.

2. The method according to claim 1, wherein the compound is selected from the group consisting of:

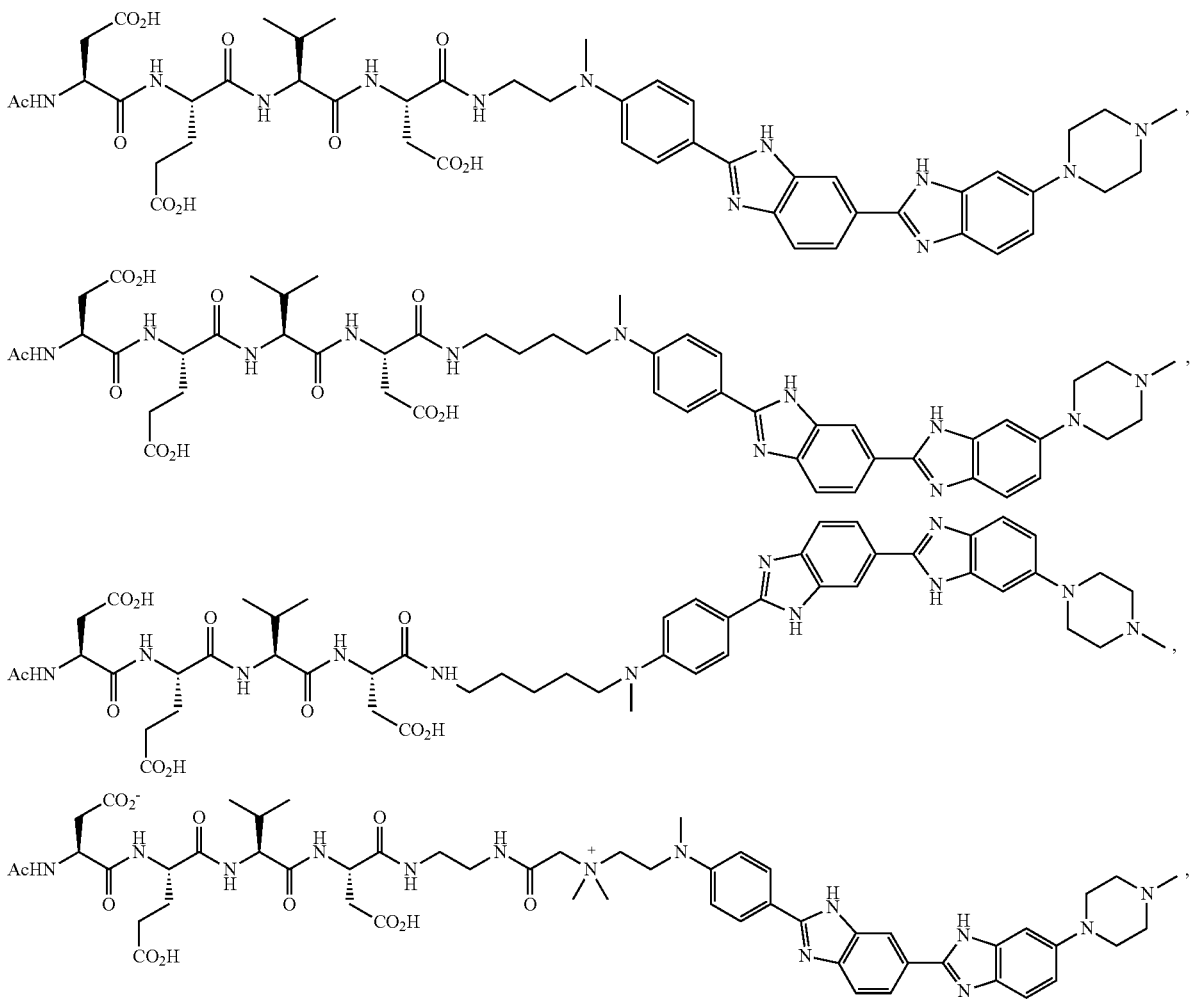

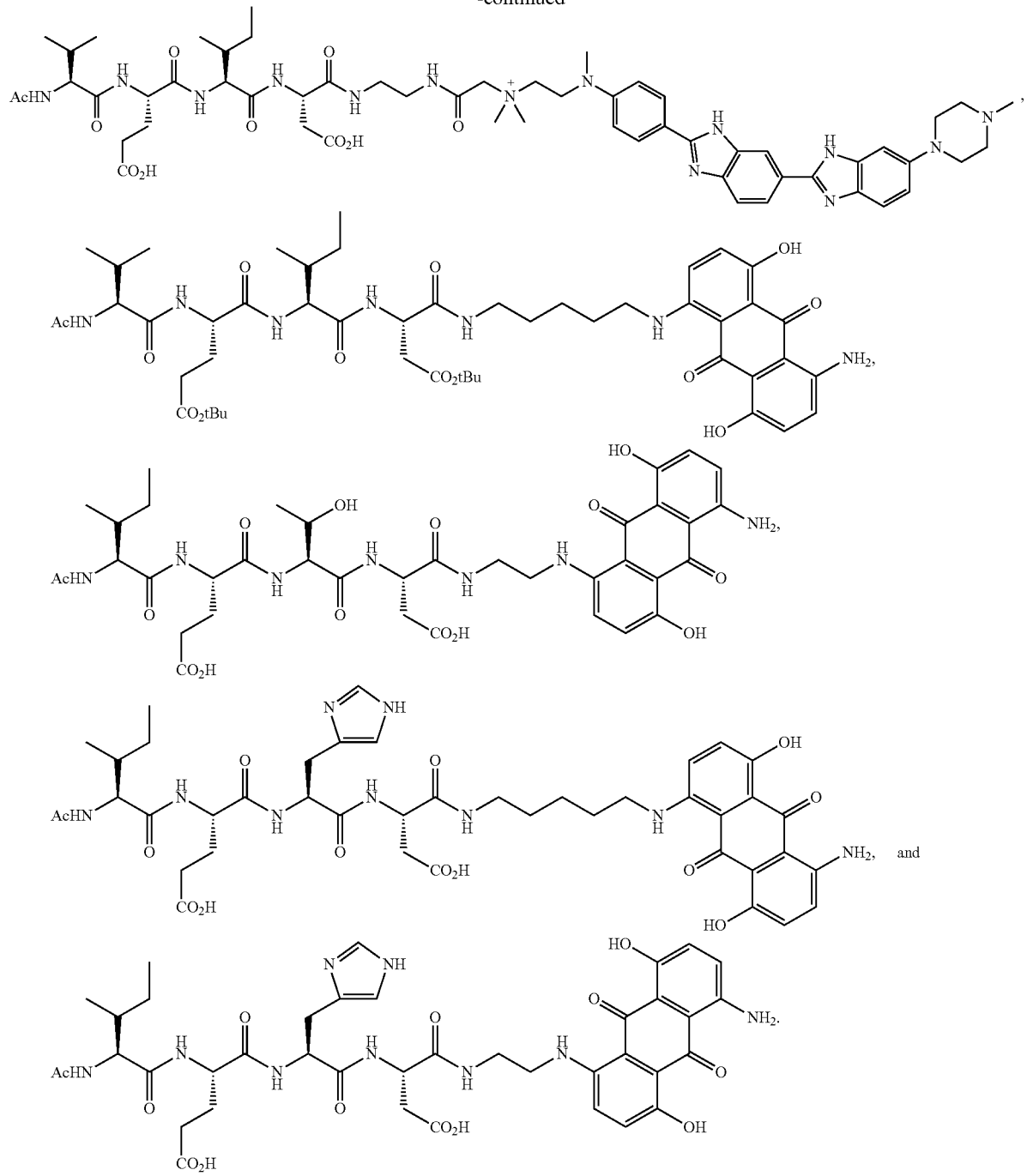

3. The method according to claim 1, wherein the compound is cleaved by a caspase enzyme.

4. The method according to claim 1, further comprising the step of incubating the cell or mixture of cells with an apoptosis inducer.

5. The method according to claim 1, further comprising the step of incubating the cell or mixture of cells with a caspase inhibitor.

6. The method according to claim 1, wherein the fluorescent signal is detected by flow cytometry.

7. The method according to claim 1, wherein the fluorescent signal is detected by fluorescence microscopy.

8. The method according to claim 1, wherein the peptide comprises an amino acid sequence of:
a) $X_2EX_1D$ (SEQ ID NO. 5), wherein $X_2$ is W, Y, I, L, D, or V, and $X_1$ is any amino acid;
b) $X_3DEX_1D$ (SEQ ID NO. 6), wherein $X_3$ is V or L and $X_1$ is any amino acid;
c) $DX_1VD$ (SEQ ID NO. 7), wherein $X_1$ is any amino acid;
d) $DX_2EX_1D$ (SEQ ID NO. 8), wherein $X_2$ is W, Y, I, L, or V, and $X_1$ is any amino acid; or
e) $DX_2VX_1D$ (SEQ ID NO. 20), wherein $X_2$ is W, Y, I, L, or V, and $X_1$ is any amino acid;

optionally wherein the amino acid sequence of a), b), c), d), or e) is the entire amino acid sequence of the peptide or the C-terminal amino acid sequence of the peptide.

9. The method according to claim 1, wherein the peptide comprises an amino acid sequence of WEHD (SEQ ID NO. 9), YVAD (SEQ ID NO. 10), YVHD (SEQ ID NO. 11), VDVAD (SEQ ID NO. 12), LEHD (SEQ ID NO. 2), IETD (SEQ ID NO. 13), VEID (SEQ ID NO. 14), DEVD (SEQ ID NO. 1), LEVD (SEQ ID NO. 15), or AEVD (SEQ ID NO. 16), optionally wherein the amino acid sequence is the entire amino acid sequence of the peptide or the C-terminal amino acid sequence of the peptide.

10. The method according to claim 1, wherein L is:
a) $-N(R_{N1})-[CH_2]_n-$, wherein n ranges from 1 to 10 and $R_{N1}$ is H or optionally substituted $C_{1-6}$ alkyl;
b) $-N(R_{N1})-L_a-$, wherein $L_a$ is a $C_{2-10}$ alkylene optionally interrupted by one or both of $-N(R_{N1})-C(O)-$ or $-N^+(R_{N2})_2-$, wherein each $R_{N1}$ is independently H or optionally substituted $C_{1-6}$ alkyl and each $R_{N2}$ is independently an optionally substituted $C_{1-6}$ alkyl;
c) $-C(O)-[CH_2]_n-$, wherein n ranges from 1 to 10;
d) $-N(R_{N1})-[CH_2]_n-C(O)-$, wherein n ranges from 1 to 10 and $R_{N1}$ is H or optionally substituted $C_{1-6}$ alkyl;
e) $-C(O)-[CH_2]_n-C(O)-$, wherein n ranges from 1 to 10;
f) $-[CH_2]_n-N^+(R_{N2})_2-[CH_2]_n-$, wherein each $R_{N2}$ is independently an optionally substituted $C_{1-6}$ alkyl;
g) $-NH-[CH_2]_2-$;
h) $-NH-[CH_2]_4-$;
i) $-NH-[CH_2]_5-$; or
j) $-NH-[CH_2]_2-NH-C(O)-CH_2-N(CH_3)_2-[CH_2]_2-$.

* * * * *

SEQUENCE LISTING

<160> NUMBER OF SEQ ID NOS: 24

<210> SEQ ID NO 1
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 3/7"

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 9"

<400> SEQUENCE: 2

Leu Glu His Asp
1

<210> SEQ ID NO 3
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 3/7"

<400> SEQUENCE: 3

Asp Glu Val Asp Gly
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 3/7"

<400> SEQUENCE: 4

Gly Asp Glu Val Asp Gly Ile Lys
1               5

<210> SEQ ID NO 5
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence"
<220> FEATURE:
<221> NAME/KEY: VARIANT
<222> LOCATION: (1)..(1)
<223> OTHER INFORMATION: /replace="Tyr" or "Ile" or "Leu" or "Asp" or

```
        "Val"
<220> FEATURE:
<221> NAME/KEY: MOD_RES
<222> LOCATION: (3)..(3)
<223> OTHER INFORMATION: Any amino acid
<220> FEATURE:
<221> NAME/KEY: MISC_FEATURE
<222> LOCATION: (1)..(4)
<223> OTHER INFORMATION: /note="Variant residues given in the sequence
      have no preference with respect to those in the annotations
      for variant positions"

<400> SEQUENCE: 5

Trp Glu Xaa Asp
1

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence"
<220> FEATURE:
<221> NAME/KEY: VARIANT
<222> LOCATION: (1)..(1)
<223> OTHER INFORMATION: /replace="Leu"
<220> FEATURE:
<221> NAME/KEY: MOD_RES
<222> LOCATION: (4)..(4)
<223> OTHER INFORMATION: Any amino acid
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 6

Val Asp Glu Xaa Asp
1               5

<210> SEQ ID NO 7
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence"
<220> FEATURE:
<221> NAME/KEY: MOD_RES
<222> LOCATION: (2)..(2)
<223> OTHER INFORMATION: Any amino acid

<400> SEQUENCE: 7

Asp Xaa Val Asp
1

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence"
<220> FEATURE:
<221> NAME/KEY: VARIANT
<222> LOCATION: (2)..(2)
<223> OTHER INFORMATION: /replace="Tyr" or "Ile" or "Leu" or "Val"
<220> FEATURE:
```

```
<221> NAME/KEY: MOD_RES
<222> LOCATION: (4)..(4)
<223> OTHER INFORMATION: Any amino acid
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 8

Asp Trp Glu Xaa Asp
1               5

<210> SEQ ID NO 9
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 1/5"

<400> SEQUENCE: 9

Trp Glu His Asp
1

<210> SEQ ID NO 10
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 1"

<400> SEQUENCE: 10

Tyr Val Ala Asp
1

<210> SEQ ID NO 11
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 1"

<400> SEQUENCE: 11

Tyr Val His Asp
1

<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 2"

<400> SEQUENCE: 12

Val Asp Val Ala Asp
1               5
```

```
<210> SEQ ID NO 13
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 8"

<400> SEQUENCE: 13

Ile Glu Thr Asp
1

<210> SEQ ID NO 14
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 6"

<400> SEQUENCE: 14

Val Glu Ile Asp
1

<210> SEQ ID NO 15
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 4/9"

<400> SEQUENCE: 15

Leu Glu Val Asp
1

<210> SEQ ID NO 16
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 10"

<400> SEQUENCE: 16

Ala Glu Val Asp
1

<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 8"

<400> SEQUENCE: 17

Asp Ile Glu Thr Asp
1               5
```

```
<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 9"

<400> SEQUENCE: 18

Asp Leu Glu His Asp
1               5

<210> SEQ ID NO 19
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence,
      e.g., for Caspase 1"

<400> SEQUENCE: 19

Asp Tyr Val Ala Asp
1               5

<210> SEQ ID NO 20
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence"
<220> FEATURE:
<221> NAME/KEY: VARIANT
<222> LOCATION: (2)..(2)
<223> OTHER INFORMATION: /replace="Tyr" or "Ile" or "Leu" or "Val"
<220> FEATURE:
<221> NAME/KEY: MOD_RES
<222> LOCATION: (4)..(4)
<223> OTHER INFORMATION: Any amino acid
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 20

Asp Trp Val Xaa Asp
1               5

<210> SEQ ID NO 21
<211> LENGTH: 205
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence"
<220> FEATURE:
<221> NAME/KEY: MOD_RES
<222> LOCATION: (1)..(100)
<223> OTHER INFORMATION: Any amino acid or not present
<220> FEATURE:
<221> NAME/KEY: MOD_RES
<222> LOCATION: (106)..(205)
<223> OTHER INFORMATION: Any amino acid or not present
```

<400> SEQUENCE: 21

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Asp Glu Val Asp Gly Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa
        195                 200                 205

<210> SEQ ID NO 22
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic cleaved peptide fragment after treatment with caspase"
<220> FEATURE:
<221> NAME/KEY: MOD_RES
<222> LOCATION: (1)..(100)
<223> OTHER INFORMATION: Any amino acid or not present

<400> SEQUENCE: 22

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Asp Glu Val Asp
            100
```

```
<210> SEQ ID NO 23
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic cleaved peptide fragment after treatment with caspase"
<220> FEATURE:
<221> NAME/KEY: MOD_RES
<222> LOCATION: (2)..(101)
<223> OTHER INFORMATION: Any amino acid or not present

<400> SEQUENCE: 23

Gly Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa
            100

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide with caspase recognition/cleavage sequence"
<220> FEATURE:
<221> NAME/KEY: VARIANT
<222> LOCATION: (2)..(2)
<223> OTHER INFORMATION: /replace="Tyr" or "Ile" or "Leu" or "Val" or
      "Asp"
<220> FEATURE:
<221> NAME/KEY: VARIANT
<222> LOCATION: (3)..(3)
<223> OTHER INFORMATION: /replace="Val"
<220> FEATURE:
<221> NAME/KEY: MOD_RES
<222> LOCATION: (4)..(4)
<223> OTHER INFORMATION: Any amino acid
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 24

Asp Trp Glu Xaa Asp
1               5
```